US010695438B2

(12) United States Patent
Durrant et al.

(10) Patent No.: US 10,695,438 B2
(45) Date of Patent: Jun. 30, 2020

(54) ANTI-TUMOUR IMMUNE RESPONSES TO MODIFIED SELF-EPITOPES

(71) Applicant: SCANCELL LIMITED, Nottingham, Nottinghamshire (GB)

(72) Inventors: Linda Gillian Durrant, Nottingham (GB); Victoria Anne Brentville, Nottingham (GB); Rachel Louise Metheringham, Nottingham (GB)

(73) Assignee: Scancell Limited, Nottingham, Nottinghams (GB)

( * ) Notice: Subject to any disclaimer, the term of this patent is extended or adjusted under 35 U.S.C. 154(b) by 37 days.

(21) Appl. No.: 15/746,077

(22) PCT Filed: Jul. 19, 2016

(86) PCT No.: PCT/GB2016/052181
§ 371 (c)(1),
(2) Date: Jan. 19, 2018

(87) PCT Pub. No.: WO2017/013425
PCT Pub. Date: Jan. 26, 2017

(65) Prior Publication Data
US 2018/0207291 A1  Jul. 26, 2018

(30) Foreign Application Priority Data
Jul. 20, 2015 (GB) .................................. 1512703.8

(51) Int. Cl.
| *C07K 7/08* | (2006.01) |
| *A61K 47/68* | (2017.01) |
| *C12N 9/88* | (2006.01) |
| *A61P 35/00* | (2006.01) |
| *A61K 39/395* | (2006.01) |
| *A61K 38/00* | (2006.01) |
| *A61K 39/00* | (2006.01) |

(52) U.S. Cl.
CPC .... *A61K 47/6811* (2017.08); *A61K 39/39558* (2013.01); *A61P 35/00* (2018.01); *C07K 7/08* (2013.01); *C12N 9/88* (2013.01); *C12Y 402/01011* (2013.01); *A61K 38/00* (2013.01); *A61K 2039/505* (2013.01)

(58) Field of Classification Search
CPC .............................. A61K 47/6811; C07K 7/08

USPC ....................................................... 424/134.1
See application file for complete search history.

(56) References Cited

U.S. PATENT DOCUMENTS

| 10,233,220 B2 | 3/2019 | Durrant et al. |
| 2006/0014225 A1 | 1/2006 | Georges et al. |
| 2006/0264378 A1 | 11/2006 | Fujii et al. |
| 2007/0248539 A1 | 10/2007 | Glassy et al. |
| 2007/0248628 A1 | 10/2007 | Keller et al. |
| 2009/0148400 A1 | 6/2009 | Singh et al. |
| 2010/0324270 A1 | 12/2010 | Hestir et al. |
| 2012/0295292 A1 | 11/2012 | Thompson et al. |
| 2013/0274125 A1 | 10/2013 | Binder et al. |
| 2018/0346537 A1 | 12/2018 | Durrant et al. |

FOREIGN PATENT DOCUMENTS

| CA | 2614103 A1 | 1/2007 | |
| EP | 1541585 A1 | 6/2005 | |
| WO | 2007000320 A2 | 1/2007 | |
| WO | 2010117694 A2 | 10/2010 | |
| WO | 2012095849 A1 | 7/2012 | |
| WO | 2012103365 A1 | 8/2012 | |
| WO | 2012138294 A1 | 10/2012 | |
| WO | WO 2012/138294 | * 10/2012 | ............... C07K 7/08 |
| WO | 2014023957 A2 | 2/2014 | |

OTHER PUBLICATIONS

Jiang, Z., et al., "Investigating Citrullinated Proteins in Tumour Cell Lines," World Journal of Surgical Oncology, 11:260, p. 260. (2013).
Lundberg, et al., "Antibodies to Citrullinated α-Enolase Peptide 1 are Specific for Rheumatoid Arthritis and Cross-React with Bacterial Enolase," Arthritis & Rheumatism, vol. 58, No. 10, pp. 3009-3019 (Oct. 2008).
Hsiao, K.C., et al., "Surface α-Enolase Promotes Extracelluar Matrix Degradation and Tumor Metastasis and Represents a New Therapeutic Target," PLOS One, vol. 8, No. 7, pp. 1-15 (Jul. 2013).

\* cited by examiner

*Primary Examiner* — Yan Xiao
(74) *Attorney, Agent, or Firm* — Elmore Patent Law Group, P.C.; Carolyn Elmore; Mahreen Hoda

(57) ABSTRACT

The present invention relates to modified citrullinated enolase peptides that can be used as targets for cancer immunotherapy. These peptides can be used as vaccines or as targets for monoclonal antibody (mAb) therapy. Such vaccines or mAbs may be used in the treatment of cancer.

Figure 2:
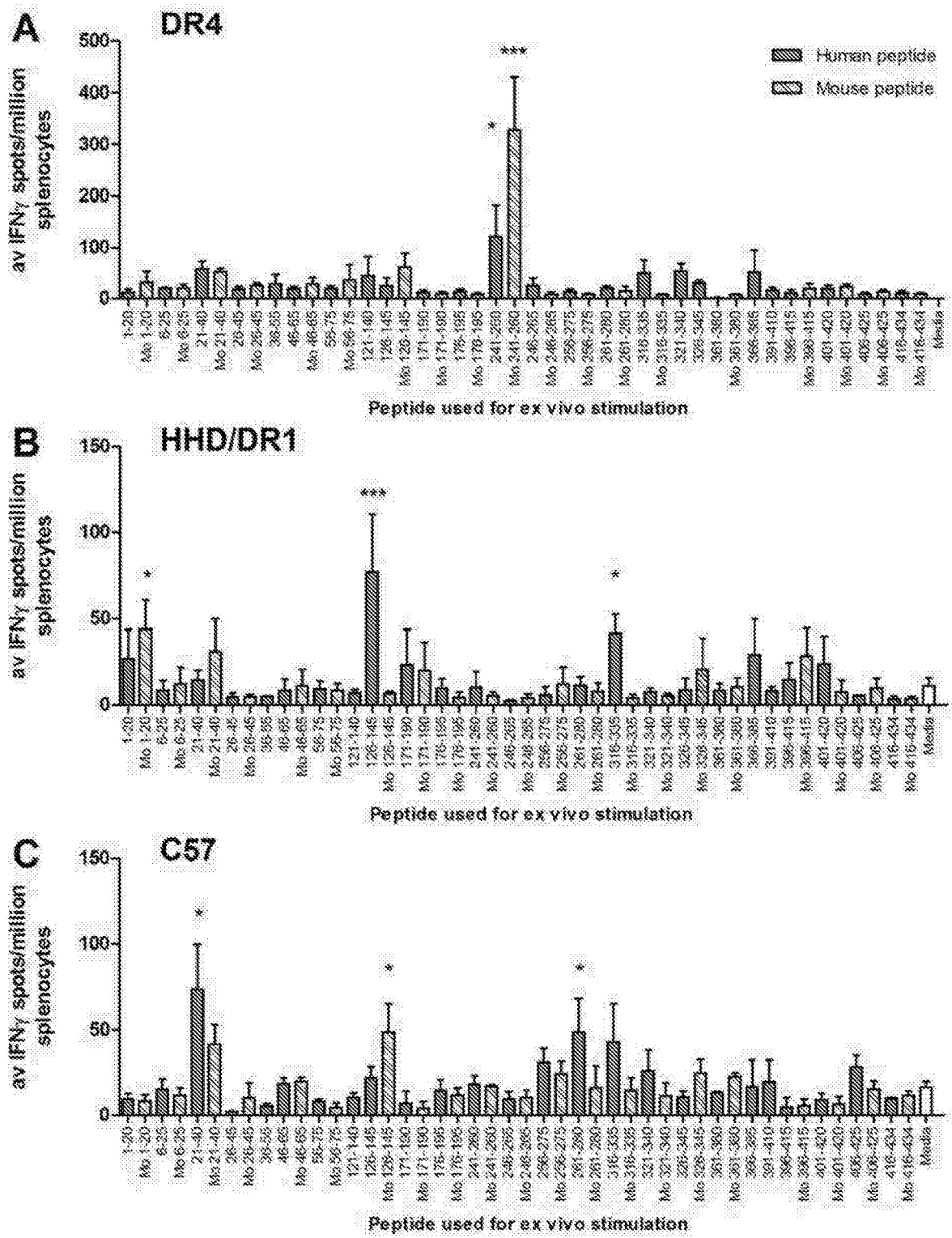

14 Claims, 31 Drawing Sheets
Specification includes a Sequence Listing.

FIG. 1

Homology of Human Alpha Enolase with other species

FIG. 12

Homology of Human Alpha Enolase with other species

FIG. 12 (cont)

Homology of Human Alpha Enolase with other species

FIG. 12 (cont).

Figure 13:
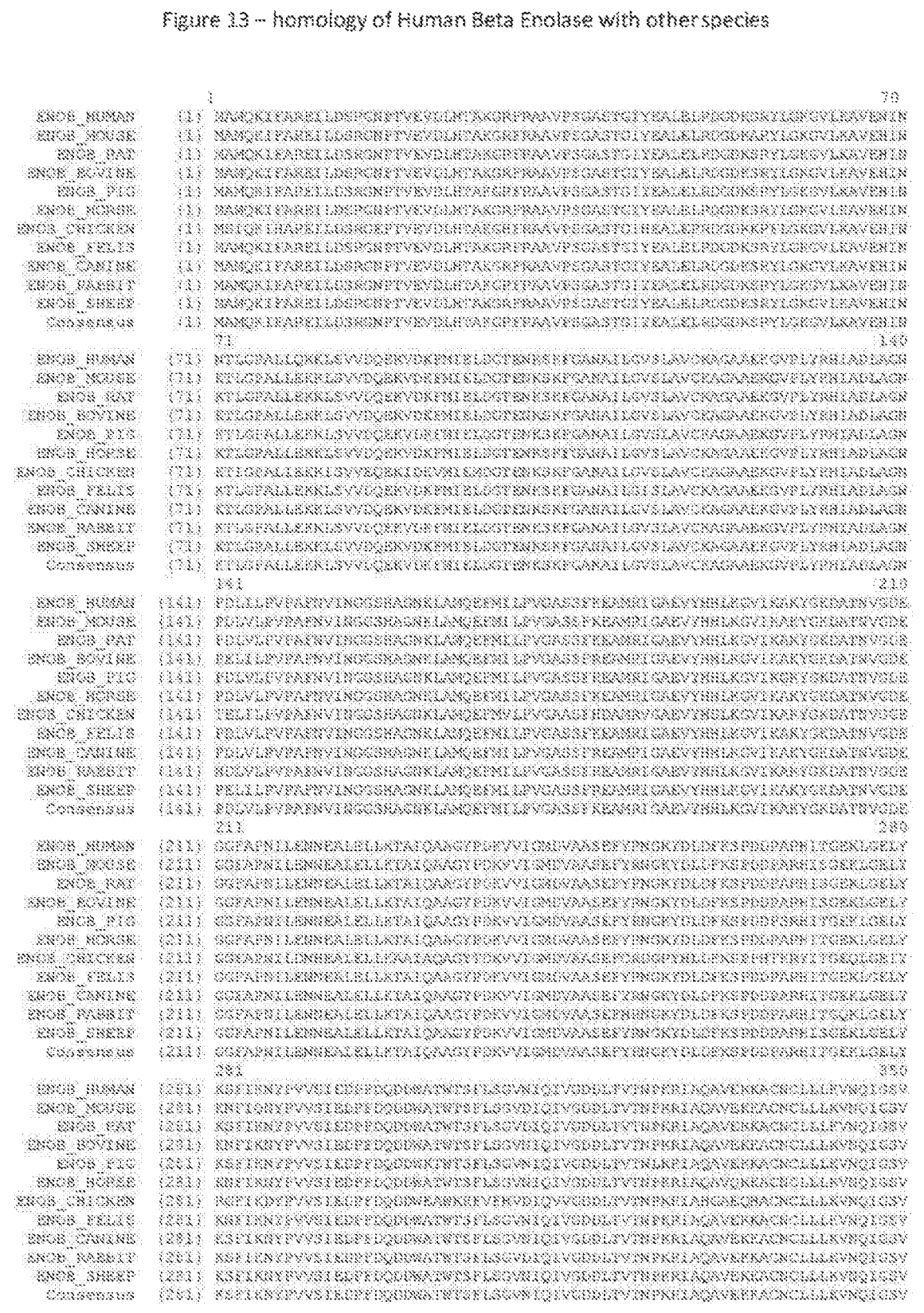

Figure 13 – homology of Human Beta Enolase with other species

Figure 13 contd – homology of Human Beta Enolase with other species

```
                    351                                                                          430
ENOB_HUMAN    (351) TESIQACKLAQSNGWGVMVSHRSGETEDTFIADLVVGLCTGQIKTGAPCRSERLAKYNQLMRIEEALGDK
ENOB_MOUSE    (351) TESIQACKLAQSNGWNVSHRSGETEDTFIADLVVGLCTGQIKTGAPCRSERLAKYNQLMRIEEALGDK
ENOB_RAT      (351) TESIQACKLAQSNGWNVSHRSGETEDTFIADLVVGLCTGQIKTGAPCRSERLAKYNQLMRIEEALGDK
ENOB_BOVINE   (351) TESIQACKLAQSNGWCVNVSHRSGETEDTFIADLVVGLCTGQIKTGAPCRSERLAKYNQLMRIEEALGDK
ENOB_PIG      (351) TESIQACKLAQSNGWCVNVSHRSGETEDTFIADLVVGLCTGQIKTGAPCRSERLAKYNQLMRIEEALGDK
ENOB_HORSE    (351) TESIQACKLAQSNGWCVNVSHRSGETEDTFIADLVVGLCTGQIKTGAPCRSERLAKYNQLMPIEEALGDK
ENOB_CHICKEN  (351) TESIQACKLAQSNGWCVNVSHRSGETEDTFIADLVVGLCTGQIKTGAPCRSERLAKYNQLMRIEEALGDK
ENOB_FELIS    (351) TESIQACKLAQSNGWCVNVSHRSGETEDTFIADLVVGLCTGQIKTGAPCRSERLAKYNQLMRIEEALGNK
ENOB_CANINE   (351) TESIQACKLAQSNGWCVNVSHRSGETEDTFIADLVVGLCTGQIKTGAPCRSERLAKYNQLMRIEEALGDK
ENOB_RABBIT   (351) TESIQACKLAQSNGWCVNVSHRSGETEDTFIADLVVGLCTGQIKTGAPCRSERLAKYNQLMRIEEALGDK
ENOB_SHEEP    (351) TESIQACKLAQSNGWCVNVSHRSGETEDTFIADLVVGLCTGQIKTGAPCRSERLAKYNQLMPIEEALGDK
Consensus     (351) TESIQACKLAQSNGWCVNVSHRSGETEDTFIADLVVGLCTGQIKTGAPCRSERLAKYNQLMRIEEALGDK
                    421       438
ENOB_HUMAN    (421) AIFAGRKFRNPKAK (SEQ ID NO. 66)
ENOB_MOUSE    (421) AVFAGRKFRNPKAK (SEQ ID NO. 80)
ENOB_RAT      (421) AVFAGRKFRNPKAK (SEQ ID NO. 81)
ENOB_BOVINE   (421) AVFAGRKFRNPKAK (SEQ ID NO. 82)
ENOB_PIG      (421) AVFAGRKFRNPKAK (SEQ ID NO. 83)
ENOB_HORSE    (421) AVFAGRKFRNPKAK (SEQ ID NO. 84)
ENOB_CHICKEN  (421) AKFAGRKFRNPKAK (SEQ ID NO. 85)
ENOB_FELIS    (421) AVFAGRKFRNPKAK (SEQ ID NO. 86)
ENOB_CANINE   (421) AVFAGRKFRNPKAK (SEQ ID NO. 87)
ENOB_RABBIT   (421) AVFAGRKFRNPKAK (SEQ ID NO. 88)
ENOB_SHEEP    (421) AVFAGRKFRNPKAK (SEQ ID NO. 89)
Consensus     (421) AVFAGRKFRNPKAK (SEQ ID NO. 90)
```

Figure 14:
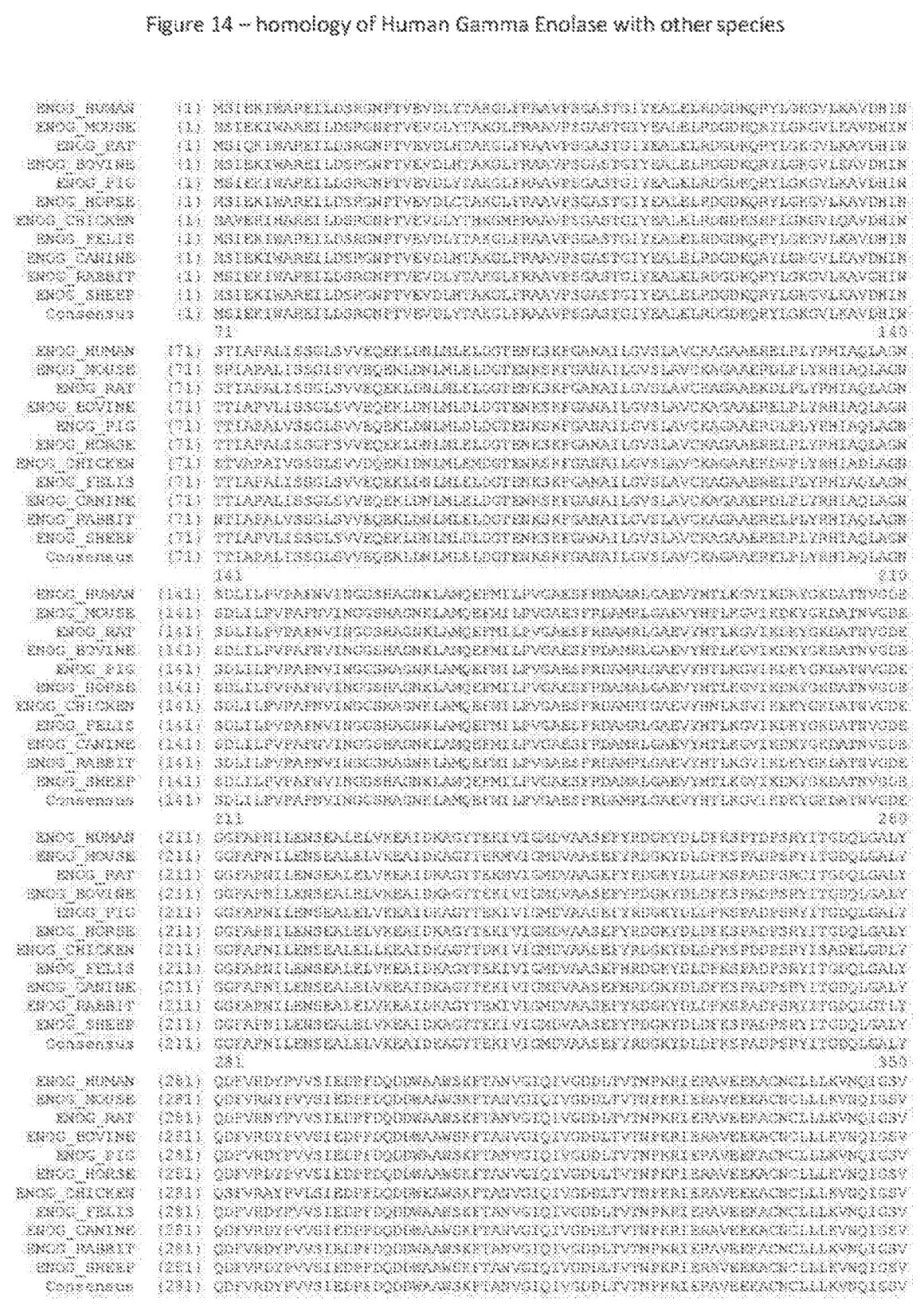

Figure 14 – homology of Human Gamma Enolase with other species

Figure 14 contd – homology of Human Gamma Enolase with other species

```
                  351                                                          420
ENO2_HUMAN    (351) TEAIQACKLAQENGWGVNVEHRSGETEDTFIADLVVGLCTGQIKTGAPCRSERLAKYNQLMRIEEELGDK
ENO2_MOUSE    (351) TEAIQACKLAQENGWGVNVEHRSGETEDTFIADLVVGLCTGQIKTGAPCRSERLAKYNQLMRIEEELGDK
ENO2_RAT      (351) TEAIQACKLAQENGWGVNVEHRSGETEDTFIADLVVGLCTGQIKTGAPCRSERLAKYNQLMRIEEELGDK
ENO2_BOVINE   (351) TEAIQACKLAQENGWGVNVEHRSGETEDTFIADLVVGLCTGQIKTGAPCRSERLAKYNQLMRIEEELGDK
ENO2_PIG      (351) SEAIQACKLAQENGWGVNVEHRSGETEDTFIADLVVGLCTGQIKTGAPCRSERLAKYNQLMRIEEELGDK
ENO2_HORSE    (351) TEAIQACKLAQENGWGVNVEHRSGETEDTFIADLVVGLCTGQIKTGAPCRSERLAKYNQLMRIEEELGDK
ENO2_CHICKEN  (351) TEAIQACKLAQENGWGVNVEHRSGETEDTFIADLVVGLCTGQIKTGAPCRSERLAKYNQLMRIEEELGDK
ENO2_FELIS    (351) TEAIQACKLAQENGWGVNVEHRSGETEDTFIADLVVGLCTGQIKTGAPCRSERLAKYNQLMRIEEELGDK
ENO2_CANINE   (351) TEAIQACKLAQENGWGVNVEHRSGETEDTFIADLVVGLCTGQIKTGAPCRSERLAKYNQLMRIEEELGDK
ENO2_RABBIT   (351) TEAIQACKLAQENGWGVNVEHRSGETEDTFIADLVVGLCTGQIKTGAPCRSERLAKYNQLMRIEEELGDK
ENO2_SHEEP    (351) TEAIQACKLAQENGWGVNVEHRSGETEDTFIADLVVGLCTGQIKTGAPCRSERLAKYNQLMRIEEELGDK
Consensus     (351) TEAIQACKLAQENGWGVNVEHRSGETEDTFIADLVVGLCTGQIKTGAPCRSERLAKYNQLMRIEEELGDK 421      438
ENO2_HUMAN    (421) APFAGRNFRNPSVL (SEQ ID NO. 67)
ENO2_MOUSE    (421) ARFAGRNFRNPSVL (SEQ ID NO. 91)
ENO2_RAT      (421) ARFAGRNFRNPSVL (SEQ ID NO. 92)
ENO2_BOVINE   (421) ARFAGRNFRNPSVL (SEQ ID NO. 93)
ENO2_PIG      (421) ARFAGRNFRNPSVL (SEQ ID NO. 94)
ENO2_HORSE    (421) APFAGRNFRNPSVL (SEQ ID NO. 95)
ENO2_CHICKEN  (421) ARFAGRNFRNPSVL (SEQ ID NO. 96)
ENO2_FELIS    (421) APFAGRNFRNPSVL (SEQ ID NO. 97)
ENO2_CANINE   (421) ARFAGRNFRNPSVL (SEQ ID NO. 98)
ENO2_RABBIT   (421) ARFAGRNFRNPSVL (SEQ ID NO. 99)
ENO2_SHEEP    (421) APFAGRNFRNPSVL (SEQ ID NO. 100)
Consensus     (421) ARFAGRNFRNPSVL (SEQ ID NO. 101)
```

Figure 15
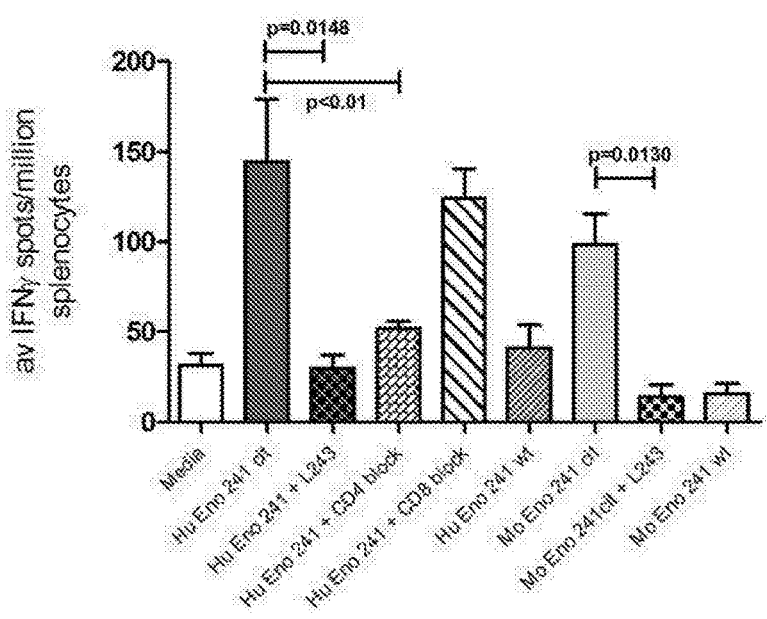
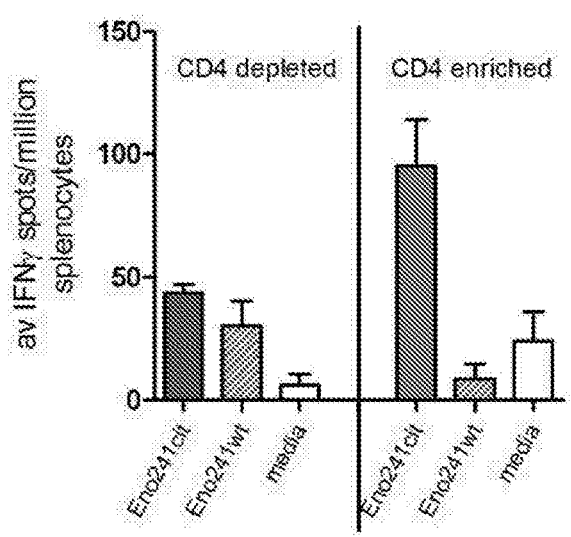
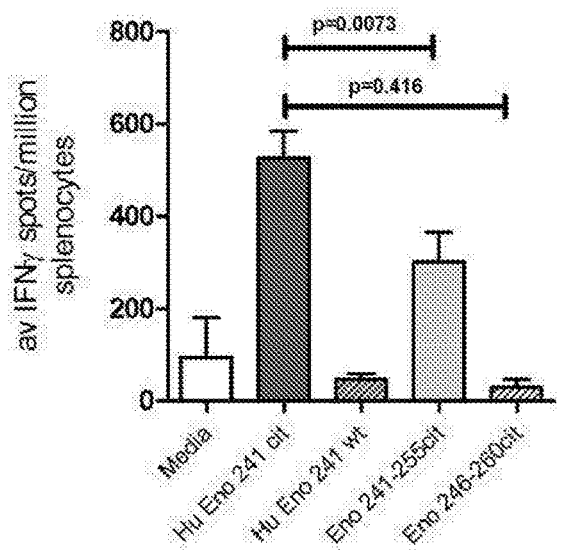

Figure 20A:
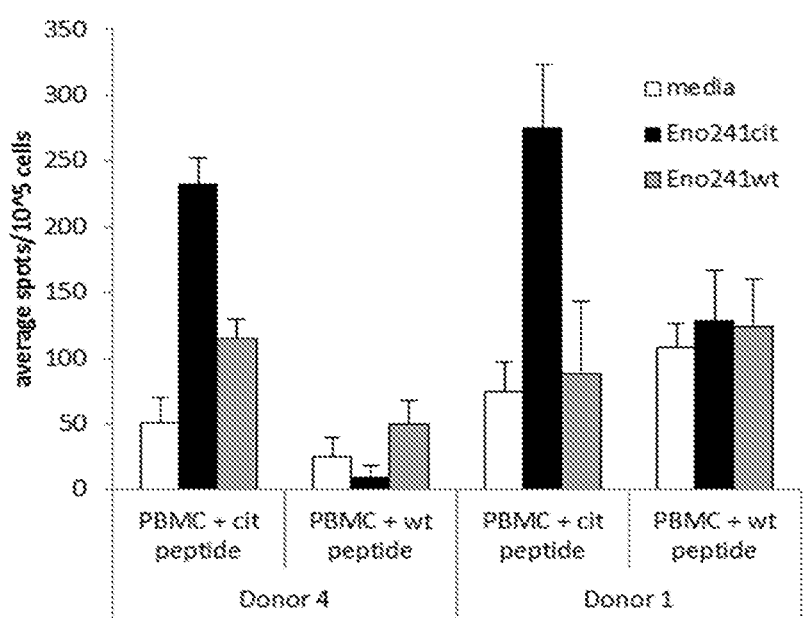
Figure 20B:
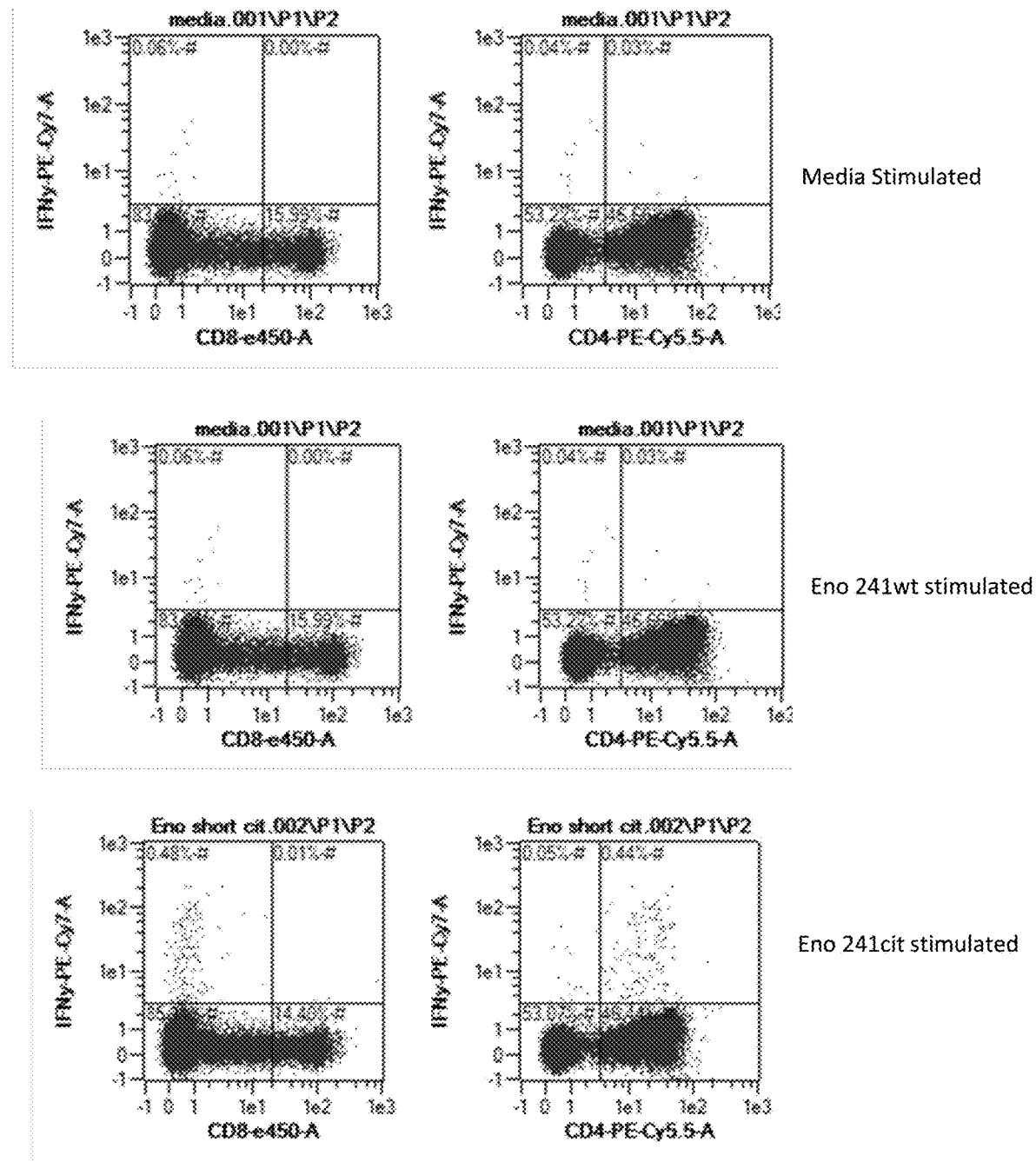
Figure 20C:
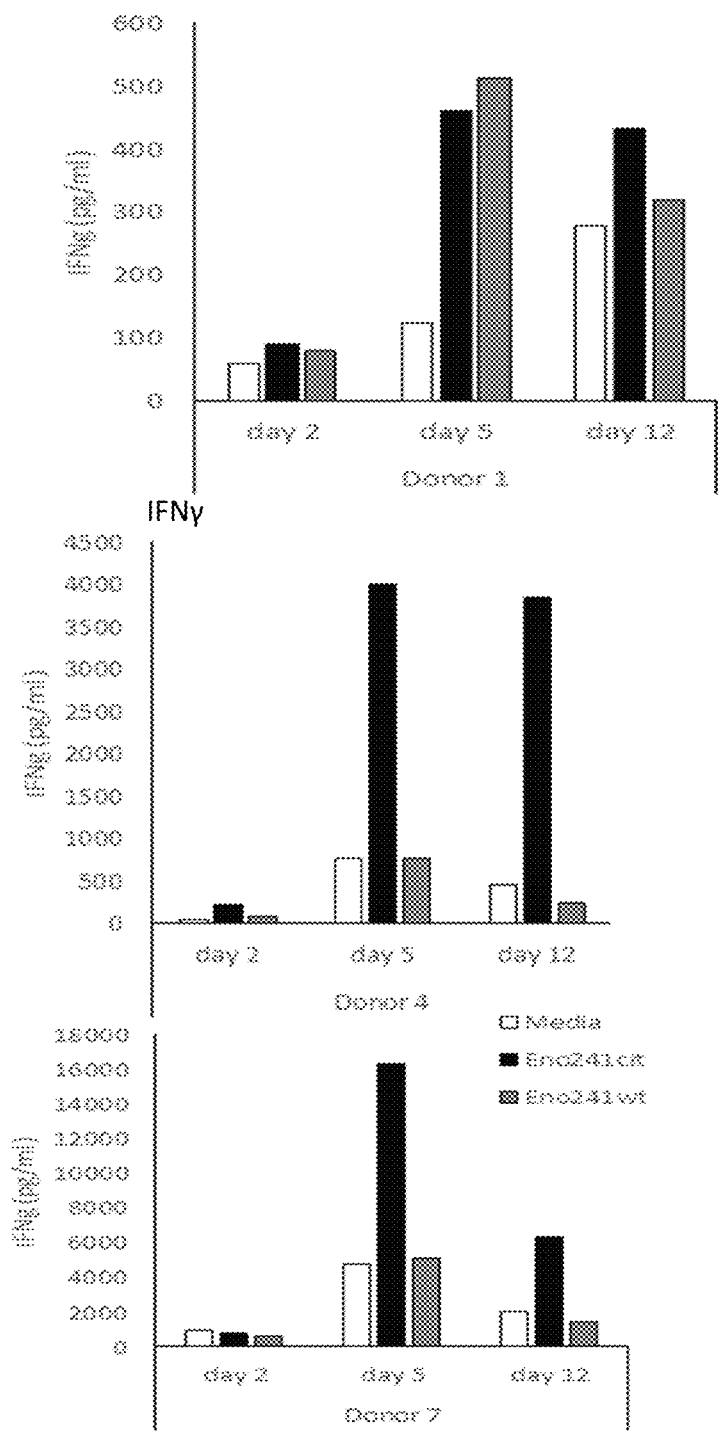

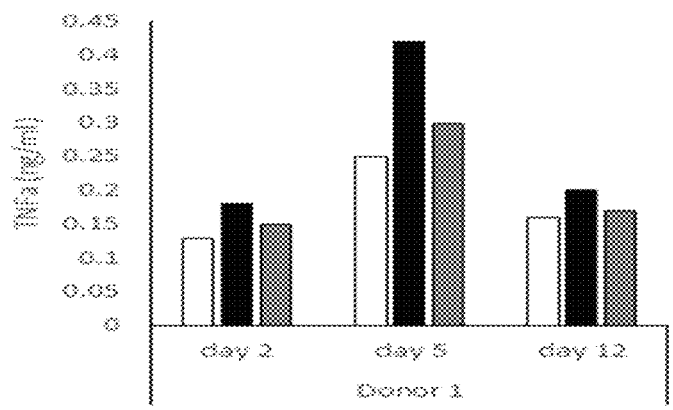
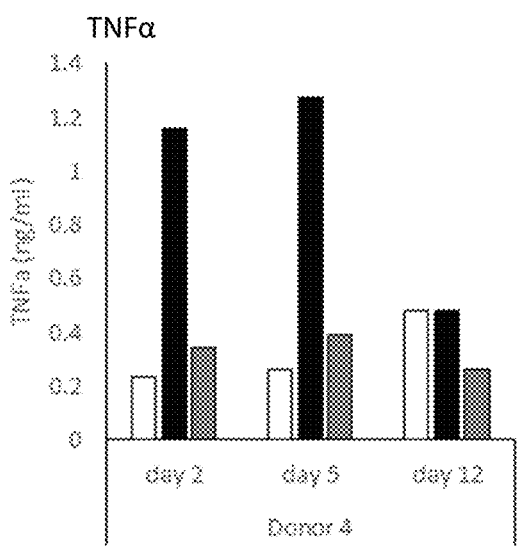
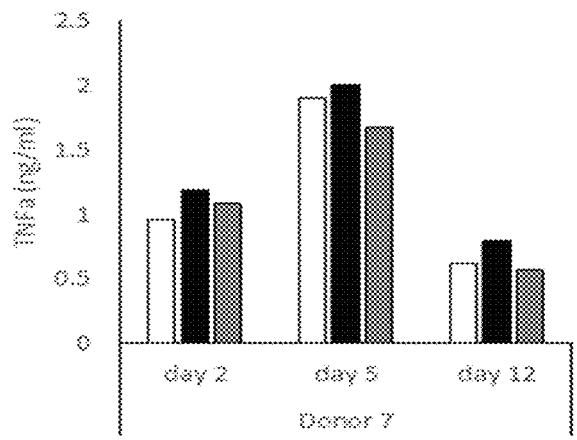
FIG. 20C (cont)

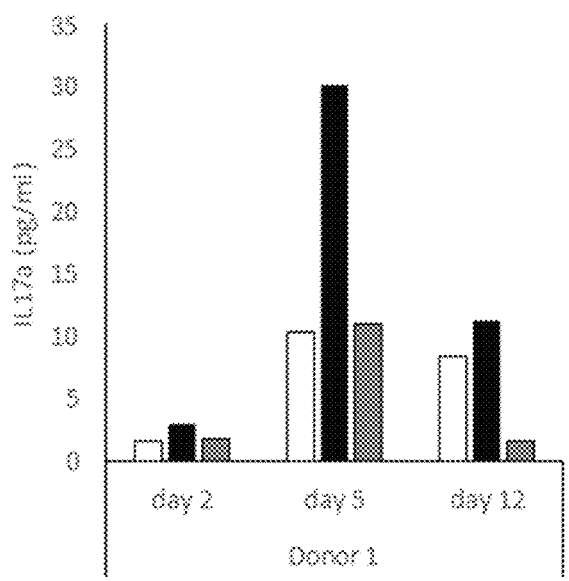
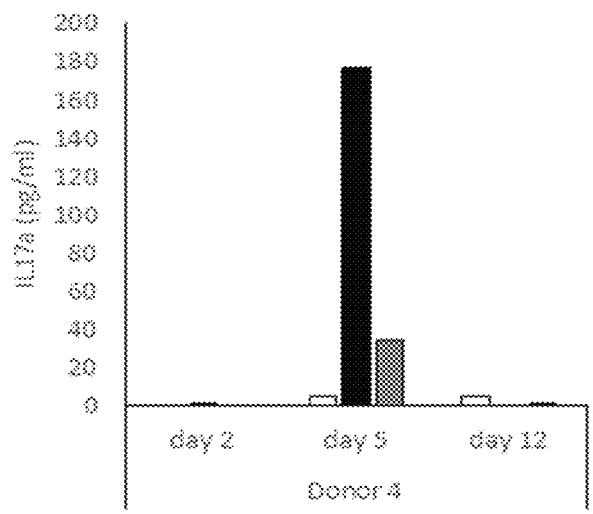
FIG. 20C (cont)

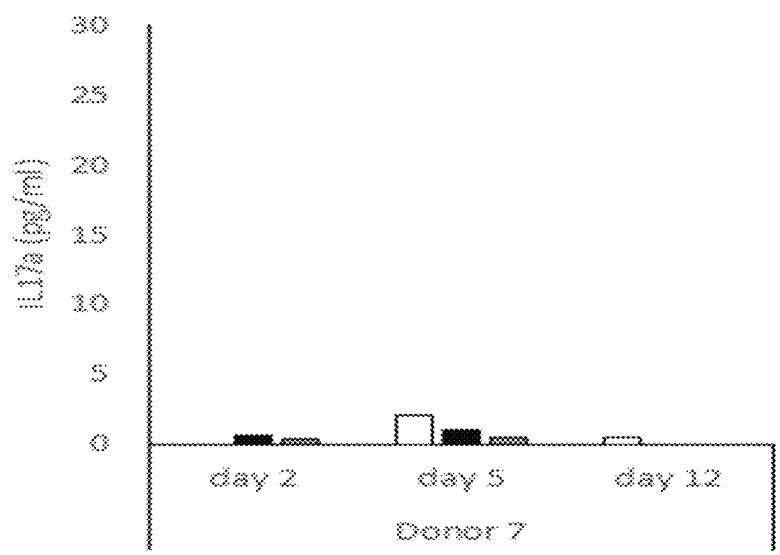
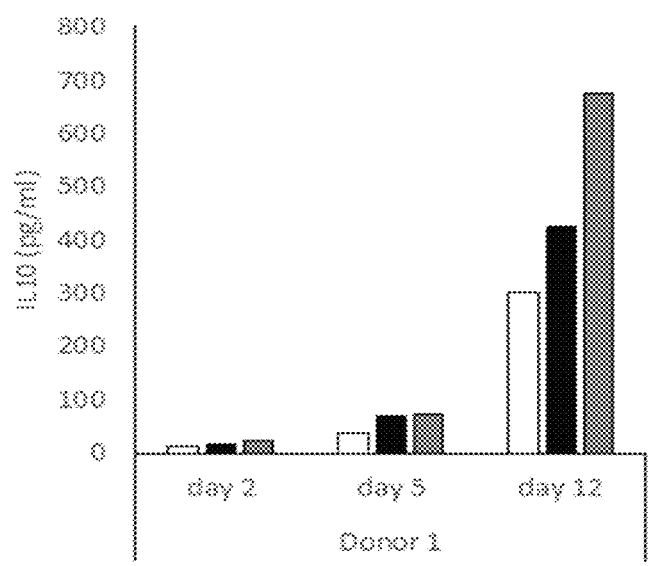
FIG. 20C (cont)

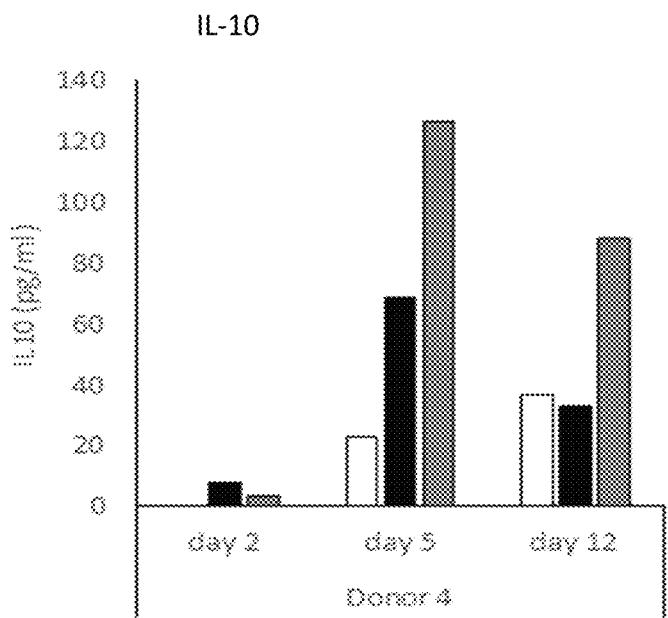
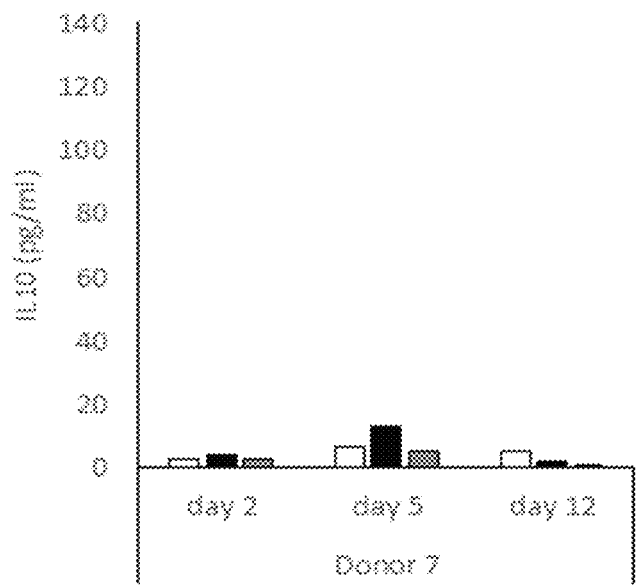
FIG. 20C (cont)

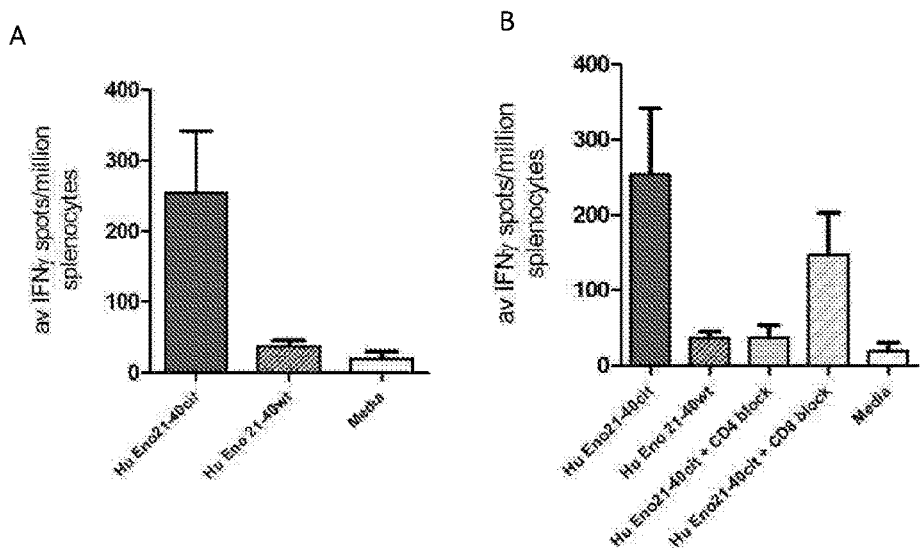
Figure 22
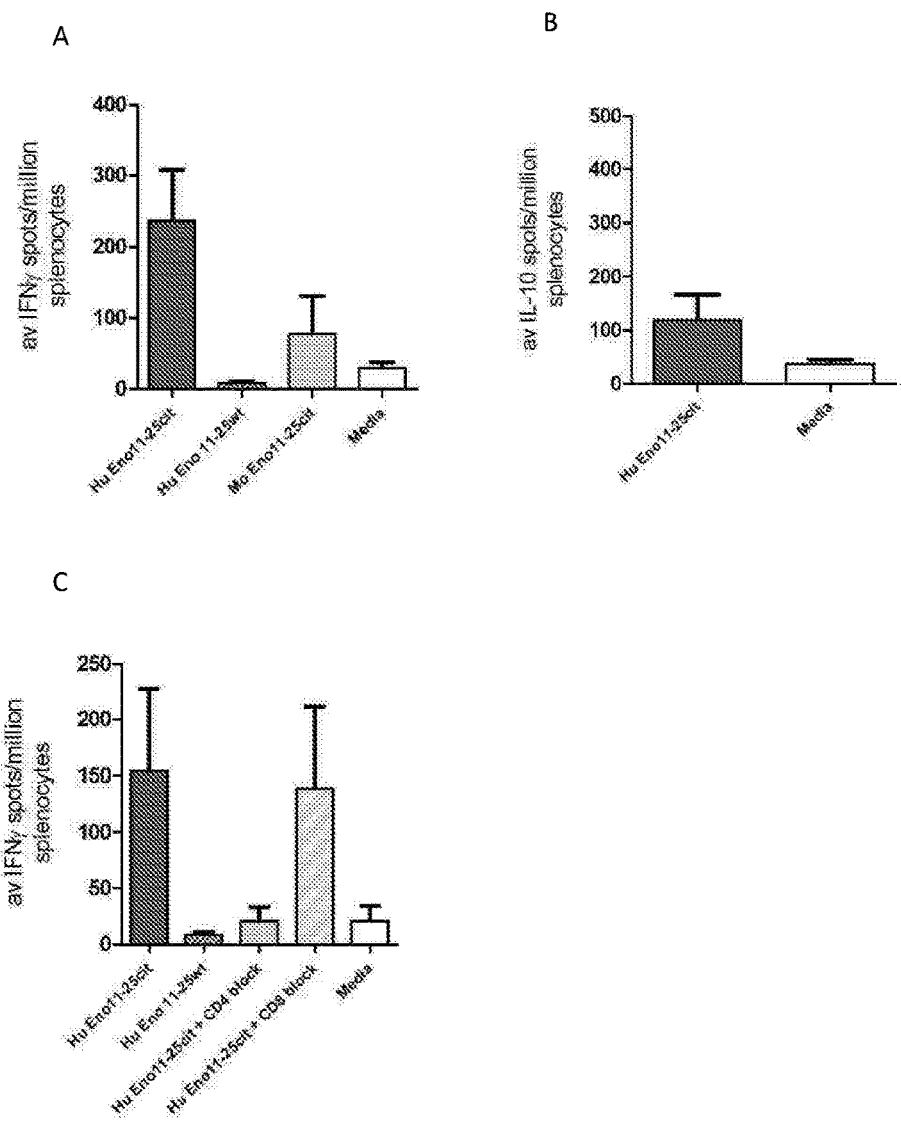

SEQUENCE LISTING

<160> NUMBER OF SEQ ID NOS: 101

<210> SEQ ID NO 1
<211> LENGTH: 20
<212> TYPE: PRT

```
<213> ORGANISM: Homo sapiens
<220> FEATURE:
<221> NAME/KEY: MISC_FEATURE
<222> LOCATION: (13)..(13)
<223> OTHER INFORMATION: where X is a citrulline

<400> SEQUENCE: 1

Val Ile Gly Met Asp Val Ala Ala Ser Glu Phe Phe Xaa Ser Gly Lys
1               5                   10                  15

Tyr Asp Leu Asp
            20

<210> SEQ ID NO 2
<211> LENGTH: 20
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: where X is a citrulline

<400> SEQUENCE: 2

Val Ile Gly Met Asp Val Ala Ala Ser Glu Phe Tyr Xaa Ser Gly Lys
1               5                   10                  15

Tyr Asp Leu Asp
            20

<210> SEQ ID NO 3
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 3

Glu Val Asp Leu Phe Thr Ser Lys Gly Leu Phe Xaa Ala Ala Val Pro
1               5                   10                  15

Ser Gly Ala Ser
            20

<210> SEQ ID NO 4
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 4

Glu Val Asp Leu Tyr Thr Ala Lys Gly Leu Phe Xaa Ala Ala Val Pro
1               5                   10                  15

Ser Gly Ala Ser
            20

<210> SEQ ID NO 5
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 5
```

```
Lys Gly Val Pro Leu Tyr Xaa His Ile Ala Asp Leu Ala Gly Asn Ser
1               5                   10                  15

Glu Val Ile Leu
            20

<210> SEQ ID NO 6
<211> LENGTH: 20
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: where X is a citrulline

<400> SEQUENCE: 6

Lys Gly Val Pro Leu Tyr Xaa His Ile Ala Asp Leu Ala Gly Asn Pro
1               5                   10                  15

Glu Val Ile Leu
            20

<210> SEQ ID NO 7
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 7

Val Gly Asp Asp Leu Thr Val Thr Asn Pro Lys Xaa Ile Ala Lys Ala
1               5                   10                  15

Val Asn Glu Lys
            20

<210> SEQ ID NO 8
<211> LENGTH: 20
<212> TYPE: PRT
<213> ORGANISM: Mouse
<220> FEATURE:
<221> NAME/KEY: MISC_FEATURE
<222> LOCATION: (12)..(12)
<223> OTHER INFORMATION: where X is a citrulline

<400> SEQUENCE: 8

Val Gly Asp Asp Leu Thr Val Thr Asn Pro Lys Xaa Ile Ala Lys Ala
1               5                   10                  15

Ala Ser Glu Lys
            20

<210> SEQ ID NO 9
<211> LENGTH: 15
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: where X is a citrulline

<400> SEQUENCE: 9

Ile Phe Asp Ser Xaa Gly Asn Pro Thr Val Glu Val Asp Leu Phe
1               5                   10                  15

<210> SEQ ID NO 10
<211> LENGTH: 15
```

```
<212> TYPE: PRT
<213> ORGANISM: Mouse
<220> FEATURE:
<221> NAME/KEY: MISC_FEATURE
<222> LOCATION: (5)..(5)
<223> OTHER INFORMATION: where X is a citrulline

<400> SEQUENCE: 10

Ile Phe Asp Ser Xaa Gly Asn Pro Thr Val Glu Val Asp Leu Tyr
1               5                   10                  15

<210> SEQ ID NO 11
<211> LENGTH: 20
<212> TYPE: PRT
<213> ORGANISM: Homo sapiens

<400> SEQUENCE: 11

Val Ala Ala Ser Glu Phe Phe Arg Ser Gly Lys Tyr Asp Leu Asp Phe
1               5                   10                  15

Lys Ser Pro Asp
            20

<210> SEQ ID NO 12
<211> LENGTH: 20
<212> TYPE: PRT
<213> ORGANISM: Homo sapiens

<400> SEQUENCE: 12

Val Ala Ala Ser Glu Phe Tyr Arg Ser Gly Lys Tyr Asp Leu Asp Phe
1               5                   10                  15

Lys Ser Pro Asp
            20

<210> SEQ ID NO 13
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 13

Thr Ser Lys Gly Leu Phe Xaa Ala Ala Val Pro Ser Gly Ala Ser Thr
1               5                   10                  15

Gly Ile Tyr Glu
            20

<210> SEQ ID NO 14
<211> LENGTH: 19
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: where X is a citrulline

<400> SEQUENCE: 14

Thr Ala Lys Gly Leu Xaa Ala Ala Val Pro Ser Gly Ala Ser Thr Gly
1               5                   10                  15

Ile Tyr Glu

<210> SEQ ID NO 15
<211> LENGTH: 20
<212> TYPE: PRT
```

```
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 15

Ala Gly Ala Val Glu Lys Gly Val Pro Leu Tyr Xaa His Ile Ala Asp
1               5                   10                  15

Leu Ala Gly Asn
            20

<210> SEQ ID NO 16
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 16

Thr Val Thr Asn Pro Lys Xaa Ile Ala Lys Ala Val Asn Glu Lys Ser
1               5                   10                  15

Cys Asn Cys Leu
            20

<210> SEQ ID NO 17
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 17

Thr Val Thr Asn Pro Lys Xaa Ile Ala Lys Ala Ala Ser Glu Lys Ser
1               5                   10                  15

Cys Asn Cys Leu
            20

<210> SEQ ID NO 18
<211> LENGTH: 20
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: where X is a citrulline

<400> SEQUENCE: 18

Met Ser Ile Leu Lys Ile His Ala Xaa Glu Ile Phe Asp Ser Arg Gly
1               5                   10                  15

Asn Pro Thr Val
            20

<210> SEQ ID NO 19
<211> LENGTH: 20
<212> TYPE: PRT
<213> ORGANISM: Mouse
<220> FEATURE:
<221> NAME/KEY: MISC_FEATURE
<222> LOCATION: (9)..(9)
<223> OTHER INFORMATION: where X is a citrulline

<400> SEQUENCE: 19
```

-continued

```
Met Ser Ile Leu Arg Ile His Ala Xaa Glu Ile Phe Asp Ser Arg Gly
1               5                   10                  15

Asn Pro Thr Val
            20

<210> SEQ ID NO 20
<211> LENGTH: 20
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: where X is a citrulline
<220> FEATURE:
<221> NAME/KEY: MISC_FEATURE
<222> LOCATION: (10)..(10)
<223> OTHER INFORMATION: where X is a citrulline

<400> SEQUENCE: 20

Ile His Ala Xaa Glu Ile Phe Asp Ser Xaa Gly Asn Pro Thr Val Glu
1               5                   10                  15

Val Asp Leu Phe
            20

<210> SEQ ID NO 21
<211> LENGTH: 20
<212> TYPE: PRT
<213> ORGANISM: Mouse
<220> FEATURE:
<221> NAME/KEY: MISC_FEATURE
<222> LOCATION: (4)..(4)
<223> OTHER INFORMATION: where X is a citrulline
<220> FEATURE:
<221> NAME/KEY: MISC_FEATURE
<222> LOCATION: (10)..(10)
<223> OTHER INFORMATION: where X is a citrulline

<400> SEQUENCE: 21

Ile His Ala Xaa Glu Ile Phe Asp Ser Xaa Gly Asn Pro Thr Val Glu
1               5                   10                  15

Val Asp Leu Tyr
            20

<210> SEQ ID NO 22
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 22

Glu Val Asp Leu Phe Thr Ser Lys Gly Leu Phe Xaa Ala Ala Val Pro
1               5                   10                  15

Ser Gly Ala Ser
            20

<210> SEQ ID NO 23
<211> LENGTH: 20
<212> TYPE: PRT
<213> ORGANISM: Mouse
<220> FEATURE:
<221> NAME/KEY: MISC_FEATURE
<222> LOCATION: (12)..(12)
<223> OTHER INFORMATION: where X is a citrulline
```

```
<400> SEQUENCE: 23

Glu Val Asp Leu Tyr Thr Ala Lys Gly Leu Phe Xaa Ala Ala Val Pro
1               5                   10                  15

Ser Gly Ala Ser
            20

<210> SEQ ID NO 24
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 24

Thr Ser Lys Gly Leu Phe Xaa Ala Ala Val Pro Ser Gly Ala Ser Thr
1               5                   10                  15

Gly Ile Tyr Glu
            20

<210> SEQ ID NO 25
<211> LENGTH: 20
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: where X is a citrulline

<400> SEQUENCE: 25

Thr Ala Lys Gly Leu Phe Xaa Ala Ala Val Pro Ser Gly Ala Ser Thr
1               5                   10                  15

Gly Ile Tyr Glu
            20

<210> SEQ ID NO 26
<211> LENGTH: 20
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: where X is a citrulline

<400> SEQUENCE: 26

Pro Ser Gly Ala Ser Thr Gly Ile Tyr Glu Ala Leu Glu Leu Xaa Asp
1               5                   10                  15

Asn Asp Lys Thr
            20

<210> SEQ ID NO 27
<211> LENGTH: 20
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: where X is a citrulline
<220> FEATURE:
<221> NAME/KEY: MISC_FEATURE
<222> LOCATION: (11)..(11)
<223> OTHER INFORMATION: where X is a citrulline

<400> SEQUENCE: 27

Ala Leu Glu Leu Xaa Asp Asn Asp Lys Thr Xaa Tyr Met Gly Lys Gly
```

```
-continued 1               5                    10                   15

Val Ser Lys Ala
            20

<210> SEQ ID NO 28
<211> LENGTH: 20
<212> TYPE: PRT
<213> ORGANISM: Mouse
<220> FEATURE:
<221> NAME/KEY: MISC_FEATURE
<222> LOCATION: (5)..(5)
<223> OTHER INFORMATION: where X is a citrulline
<220> FEATURE:
<221> NAME/KEY: MISC_FEATURE
<222> LOCATION: (11)..(11)
<223> OTHER INFORMATION: where X is a citrulline

<400> SEQUENCE: 28

Ala Leu Glu Leu Xaa Asp Asn Asp Lys Thr Xaa Phe Met Gly Lys Gly
1               5                   10                  15

Val Ser Gln Ala
            20

<210> SEQ ID NO 29
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: where X is a citrulline

<400> SEQUENCE: 29

Xaa Tyr Met Gly Lys Gly Val Ser Lys Ala Val Glu His Ile Asn Lys
1               5                   10                  15

Thr Ile Ala Pro
            20

<210> SEQ ID NO 30
<211> LENGTH: 20
<212> TYPE: PRT
<213> ORGANISM: Mouse
<220> FEATURE:
<221> NAME/KEY: MISC_FEATURE
<222> LOCATION: (1)..(1)
<223> OTHER INFORMATION: where X is a citrulline

<400> SEQUENCE: 30

Xaa Phe Met Gly Lys Gly Val Ser Gln Ala Val Glu His Ile Asn Lys
1               5                   10                  15

Thr Ile Ala Pro
            20

<210> SEQ ID NO 31
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 31

Ala Gly Ala Val Glu Lys Gly Val Pro Leu Tyr Xaa His Ile Ala Asp
1               5                   10                  15

Leu Ala Gly Asn
```

-continued

```
                20

<210> SEQ ID NO 32
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 32

Lys Gly Val Pro Leu Tyr Xaa His Ile Ala Asp Leu Ala Gly Asn Ser
1               5                   10                  15

Glu Val Ile Leu
            20

<210> SEQ ID NO 33
<211> LENGTH: 20
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: where X is a citrulline

<400> SEQUENCE: 33

Lys Gly Val Pro Leu Tyr Xaa His Ile Ala Asp Leu Ala Gly Asn Pro
1               5                   10                  15

Glu Val Ile Leu
            20

<210> SEQ ID NO 34
<211> LENGTH: 20
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: where X is a citrulline
<220> FEATURE:
<221> NAME/KEY: MISC_FEATURE
<222> LOCATION: (13)..(13)
<223> OTHER INFORMATION: where X is a citrulline

<400> SEQUENCE: 34

Leu Pro Val Gly Ala Ala Asn Phe Xaa Glu Ala Met Xaa Ile Gly Ala
1               5                   10                  15

Glu Val Tyr His
            20

<210> SEQ ID NO 35
<211> LENGTH: 20
<212> TYPE: PRT
<213> ORGANISM: Mouse
<220> FEATURE:
<221> NAME/KEY: MISC_FEATURE
<222> LOCATION: (9)..(9)
<223> OTHER INFORMATION: where X is a citrulline
<220> FEATURE:
<221> NAME/KEY: MISC_FEATURE
<222> LOCATION: (13)..(13)
<223> OTHER INFORMATION: where X is a citrulline

<400> SEQUENCE: 35

Leu Pro Val Gly Ala Ser Ser Phe Xaa Glu Ala Met Xaa Ile Gly Ala
1               5                   10                  15
```

```
Glu Val Tyr His
            20

<210> SEQ ID NO 36
<211> LENGTH: 20
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: where X is a citrulline
<220> FEATURE:
<221> NAME/KEY: MISC_FEATURE
<222> LOCATION: (8)..(8)
<223> OTHER INFORMATION: where X is a citrulline

<400> SEQUENCE: 36

Ala Asn Phe Xaa Glu Ala Met Xaa Ile Gly Ala Glu Val Tyr His Asn
1               5                  10                  15

Leu Lys Asn Val
            20

<210> SEQ ID NO 37
<211> LENGTH: 20
<212> TYPE: PRT
<213> ORGANISM: Mouse
<220> FEATURE:
<221> NAME/KEY: MISC_FEATURE
<222> LOCATION: (4)..(4)
<223> OTHER INFORMATION: where X is a citrulline
<220> FEATURE:
<221> NAME/KEY: MISC_FEATURE
<222> LOCATION: (8)..(8)
<223> OTHER INFORMATION: where X is a citrulline

<400> SEQUENCE: 37

Ser Ser Phe Xaa Glu Ala Met Xaa Ile Gly Ala Glu Val Tyr His Asn
1               5                  10                  15

Leu Lys Asn Val
            20

<210> SEQ ID NO 38
<211> LENGTH: 20
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: where X is a citrulline

<400> SEQUENCE: 38

Val Ile Gly Met Asp Val Ala Ala Ser Glu Phe Phe Xaa Ser Gly Lys
1               5                  10                  15

Tyr Asp Leu Asp
            20

<210> SEQ ID NO 39
<211> LENGTH: 20
<212> TYPE: PRT
<213> ORGANISM: Mouse
<220> FEATURE:
<221> NAME/KEY: MISC_FEATURE
<222> LOCATION: (13)..(13)
<223> OTHER INFORMATION: where X is a citrulline

<400> SEQUENCE: 39

Val Ile Gly Met Asp Val Ala Ala Ser Glu Phe Tyr Xaa Ser Gly Lys
1               5                  10                  15
```

Tyr Asp Leu Asp
            20

<210> SEQ ID NO 40
<211> LENGTH: 20
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: where X is a citrulline

<400> SEQUENCE: 40

Val Ala Ala Ser Glu Phe Phe Xaa Ser Gly Lys Tyr Asp Leu Asp Phe
1               5                   10                  15

Lys Ser Pro Asp
            20

<210> SEQ ID NO 41
<211> LENGTH: 20
<212> TYPE: PRT
<213> ORGANISM: Mouse
<220> FEATURE:
<221> NAME/KEY: MISC_FEATURE
<222> LOCATION: (8)..(8)
<223> OTHER INFORMATION: where X is a citrulline

<400> SEQUENCE: 41

Val Ala Ala Ser Glu Phe Tyr Xaa Ser Gly Lys Tyr Asp Leu Asp Phe
1               5                   10                  15

Lys Ser Pro Asp
            20

<210> SEQ ID NO 42
<211> LENGTH: 20
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: where X is a citrulline

<400> SEQUENCE: 42

Lys Tyr Asp Leu Asp Phe Lys Ser Pro Asp Pro Ser Xaa Tyr Ile
1               5                   10                  15

Ser Pro Asp Gln
            20

<210> SEQ ID NO 43
<211> LENGTH: 20
<212> TYPE: PRT
<213> ORGANISM: Mouse
<220> FEATURE:
<221> NAME/KEY: MISC_FEATURE
<222> LOCATION: (14)..(14)
<223> OTHER INFORMATION: where X is a citrulline

<400> SEQUENCE: 43

Lys Tyr Asp Leu Asp Phe Lys Ser Pro Asp Pro Ser Xaa Tyr Ile
1               5                   10                  15

Thr Pro Asp Gln
            20

<210> SEQ ID NO 44
<211> LENGTH: 20

```
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: where X is a citrulline

<400> SEQUENCE: 44

Phe Lys Ser Pro Asp Asp Pro Ser Xaa Tyr Ile Ser Pro Asp Gln Leu
1               5                   10                  15

Ala Asp Leu Tyr
            20

<210> SEQ ID NO 45
<211> LENGTH: 20
<212> TYPE: PRT
<213> ORGANISM: Mouse
<220> FEATURE:
<221> NAME/KEY: MISC_FEATURE
<222> LOCATION: (9)..(9)
<223> OTHER INFORMATION: where X is a citrulline

<400> SEQUENCE: 45

Phe Lys Ser Pro Asp Asp Pro Ser Xaa Tyr Ile Thr Pro Asp Gln Leu
1               5                   10                  15

Ala Asp Leu Tyr
            20

<210> SEQ ID NO 46
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 46

Val Gly Asp Asp Leu Thr Val Thr Asn Pro Lys Xaa Ile Ala Lys Ala
1               5                   10                  15

Val Asn Glu Lys
            20

<210> SEQ ID NO 47
<211> LENGTH: 20
<212> TYPE: PRT
<213> ORGANISM: Mouse
<220> FEATURE:
<221> NAME/KEY: MISC_FEATURE
<222> LOCATION: (12)..(12)
<223> OTHER INFORMATION: where X is a citrulline

<400> SEQUENCE: 47

Val Gly Asp Asp Leu Thr Val Thr Asn Pro Lys Xaa Ile Ala Lys Ala
1               5                   10                  15

Ala Ser Glu Lys
            20

<210> SEQ ID NO 48
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline
```

```
<400> SEQUENCE: 48

Thr Val Thr Asn Pro Lys Xaa Ile Ala Lys Ala Val Asn Glu Lys Ser
1               5                   10                  15

Cys Asn Cys Leu
            20

<210> SEQ ID NO 49
<211> LENGTH: 20
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: where X is a citrulline

<400> SEQUENCE: 49

Thr Val Thr Asn Pro Lys Xaa Ile Ala Lys Ala Ala Ser Glu Lys Ser
1               5                   10                  15

Cys Asn Cys Leu
            20

<210> SEQ ID NO 50
<211> LENGTH: 20
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: where X is a citrulline

<400> SEQUENCE: 50

Lys Xaa Ile Ala Lys Ala Val Asn Glu Lys Ser Cys Asn Cys Leu Leu
1               5                   10                  15

Leu Lys Val Asn
            20

<210> SEQ ID NO 51
<211> LENGTH: 20
<212> TYPE: PRT
<213> ORGANISM: Mouse
<220> FEATURE:
<221> NAME/KEY: MISC_FEATURE
<222> LOCATION: (2)..(2)
<223> OTHER INFORMATION: where X is a citrulline

<400> SEQUENCE: 51

Lys Xaa Ile Ala Lys Ala Ala Ser Glu Lys Ser Cys Asn Cys Leu Leu
1               5                   10                  15

Leu Lys Val Asn
            20

<210> SEQ ID NO 52
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: where X is a citrulline

<400> SEQUENCE: 52

Gln Ala Asn Gly Trp Gly Val Met Val Ser His Xaa Ser Gly Glu Thr
1               5                   10                  15

Glu Asp Thr Phe
            20
```

```
<210> SEQ ID NO 53
<211> LENGTH: 20
<212> TYPE: PRT
<213> ORGANISM: Mouse
<220> FEATURE:
<221> NAME/KEY: MISC_FEATURE
<222> LOCATION: (12)..(12)
<223> OTHER INFORMATION: where X is a citrulline

<400> SEQUENCE: 53

Gln Ser Asn Gly Trp Gly Val Met Val Ser His Xaa Ser Gly Glu Thr
1               5                   10                  15

Glu Asp Thr Phe
        20

<210> SEQ ID NO 54
<211> LENGTH: 20
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 54

Gly Val Met Val Ser His Xaa Ser Gly Glu Thr Glu Asp Thr Phe Ile
1               5                   10                  15

Ala Asp Leu Val
        20

<210> SEQ ID NO 55
<211> LENGTH: 20
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: where X is a citrulline
<220> FEATURE:
<221> NAME/KEY: MISC_FEATURE
<222> LOCATION: (13)..(13)
<223> OTHER INFORMATION: where X is a citrulline

<400> SEQUENCE: 55

Gly Gln Ile Lys Thr Gly Ala Pro Cys Xaa Ser Glu Xaa Leu Ala Lys
1               5                   10                  15

Tyr Asn Gln Leu
        20

<210> SEQ ID NO 56
<211> LENGTH: 20
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: where X is a citrulline
<220> FEATURE:
<221> NAME/KEY: MISC_FEATURE
<222> LOCATION: (8)..(8)
<223> OTHER INFORMATION: where X is a citrulline
<220> FEATURE:
<221> NAME/KEY: MISC_FEATURE
<222> LOCATION: (17)..(17)
<223> OTHER INFORMATION: where X is a citrulline

<400> SEQUENCE: 56
```

Gly Ala Pro Cys Xaa Ser Glu Xaa Leu Ala Lys Tyr Asn Gln Leu Leu
1               5                   10                  15

Xaa Ile Glu Glu
         20

<210> SEQ ID NO 57
<211> LENGTH: 20
<212> TYPE: PRT
<213> ORGANISM: Mouse
<220> FEATURE:
<221> NAME/KEY: MISC_FEATURE
<222> LOCATION: (5)..(5)
<223> OTHER INFORMATION: where X is a citrulline
<220> FEATURE:
<221> NAME/KEY: MISC_FEATURE
<222> LOCATION: (8)..(8)
<223> OTHER INFORMATION: where X is a citrulline
<220> FEATURE:
<221> NAME/KEY: MISC_FEATURE
<222> LOCATION: (17)..(17)
<223> OTHER INFORMATION: where X is a citrulline

<400> SEQUENCE: 57

Gly Ala Pro Cys Xaa Ser Glu Xaa Leu Ala Lys Tyr Asn Gln Ile Leu
1               5                   10                  15

Xaa Ile Glu Glu
         20

<210> SEQ ID NO 58
<211> LENGTH: 20
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: where X is a citrulline
<220> FEATURE:
<221> NAME/KEY: MISC_FEATURE
<222> LOCATION: (12)..(12)
<223> OTHER INFORMATION: where X is a citrulline

<400> SEQUENCE: 58

Ser Glu Xaa Leu Ala Lys Tyr Asn Gln Leu Leu Xaa Ile Glu Glu Glu
1               5                   10                  15

Leu Gly Ser Lys
         20

<210> SEQ ID NO 59
<211> LENGTH: 20
<212> TYPE: PRT
<213> ORGANISM: Mouse
<220> FEATURE:
<221> NAME/KEY: MISC_FEATURE
<222> LOCATION: (3)..(3)
<223> OTHER INFORMATION: where X is a citrulline
<220> FEATURE:
<221> NAME/KEY: MISC_FEATURE
<222> LOCATION: (12)..(12)
<223> OTHER INFORMATION: where X is a citrulline

<400> SEQUENCE: 59

Ser Glu Xaa Leu Ala Lys Tyr Asn Gln Ile Leu Xaa Ile Glu Glu Glu
1               5                   10                  15

Leu Gly Ser Lys
         20

<210> SEQ ID NO 60
<211> LENGTH: 20

```
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: where X is a citrulline

<400> SEQUENCE: 60

Lys Tyr Asn Gln Leu Leu Xaa Ile Glu Glu Glu Leu Gly Ser Lys Ala
1               5                   10                  15

Lys Phe Ala Gly
            20

<210> SEQ ID NO 61
<211> LENGTH: 20
<212> TYPE: PRT
<213> ORGANISM: Mouse
<220> FEATURE:
<221> NAME/KEY: MISC_FEATURE
<222> LOCATION: (7)..(7)
<223> OTHER INFORMATION: where X is a citrulline

<400> SEQUENCE: 61

Lys Tyr Asn Gln Ile Leu Xaa Ile Glu Glu Glu Leu Gly Ser Lys Ala
1               5                   10                  15

Lys Phe Ala Gly
            20

<210> SEQ ID NO 62
<211> LENGTH: 19
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: where X is a citrulline
<220> FEATURE:
<221> NAME/KEY: MISC_FEATURE
<222> LOCATION: (14)..(14)
<223> OTHER INFORMATION: where X is a citrulline

<400> SEQUENCE: 62

Glu Leu Gly Ser Lys Ala Lys Phe Ala Gly Xaa Asn Phe Xaa Asn Pro
1               5                   10                  15

Leu Ala Lys

<210> SEQ ID NO 63
<211> LENGTH: 19
<212> TYPE: PRT
<213> ORGANISM: Mouse
<220> FEATURE:
<221> NAME/KEY: MISC_FEATURE
<222> LOCATION: (11)..(11)
<223> OTHER INFORMATION: where X is a citrulline
<220> FEATURE:
<221> NAME/KEY: MISC_FEATURE
<222> LOCATION: (14)..(14)
<223> OTHER INFORMATION: where X is a citrulline

<400> SEQUENCE: 63

Glu Leu Gly Ser Lys Ala Lys Phe Ala Gly Xaa Ser Phe Xaa Asn Pro
1               5                   10                  15

Leu Ala Lys

<210> SEQ ID NO 64
<211> LENGTH: 628
<212> TYPE: PRT
```

<213> ORGANISM: Homo sapiens

<400> SEQUENCE: 64

Met Glu Glu Glu Gly Gly Arg Ser Cys Gly Thr Thr Arg Glu Leu
1               5                   10                  15

Gln Lys Leu Lys Gln Gln Ala Met Glu Tyr Tyr Arg Glu Asn Asp Val
            20                  25                  30

Pro Arg Arg Leu Glu Glu Leu Leu Asn Ser Thr Phe Tyr Leu Gln Pro
        35                  40                  45

Ala Asp Val Tyr Gly His Leu Lys Ala Asn Cys Phe Ser Lys Leu Ala
    50                  55                  60

Lys Pro Pro Thr Ile Cys Lys Ile Val Gly Lys Asp Val Leu Asp Gly
65                  70                  75                  80

Leu Gly Leu Pro Thr Leu Gln Val Asp Ile Phe Cys Thr Ile Gln Asn
                85                  90                  95

Phe Pro Lys Asn Val Cys Ser Val Val Ile Ser Thr His Phe Glu Val
            100                 105                 110

His Glu Asn Ala Leu Pro Glu Leu Ala Lys Ala Glu Ala Glu Arg
        115                 120                 125

Ala Ser Ala Val Ser Thr Ala Val Gln Trp Val Asn Ser Thr Ile Thr
    130                 135                 140

His Glu Leu Gln Gly Met Ala Pro Ser Asp Gln Ala Glu Val Asp His
145                 150                 155                 160

Leu Leu Arg Ile Phe Phe Ala Ser Lys Val Gln Glu Asp Lys Gly Arg
                165                 170                 175

Lys Glu Leu Glu Lys Ser Leu Glu Tyr Ser Thr Val Pro Thr Pro Leu
            180                 185                 190

Pro Pro Val Pro Pro Pro Pro Pro Pro Pro Thr Lys Lys Lys
        195                 200                 205

Gly Gln Lys Pro Gly Arg Lys Asp Thr Ile Thr Glu Lys Pro Ile Ala
    210                 215                 220

Pro Ala Glu Pro Val Glu Pro Val Leu Ser Gly Ser Met Ala Ile Gly
225                 230                 235                 240

Ala Val Ser Leu Ala Val Ala Lys Ala Cys Ala Met Leu Leu Asn Lys
                245                 250                 255

Pro Leu Tyr Leu Asn Ile Ala Leu Leu Lys His Asn Gln Glu Gln Pro
            260                 265                 270

Thr Thr Leu Ser Met Pro Leu Leu Met Val Ser Leu Ser Cys Gly
        275                 280                 285

Lys Ser Ser Ser Gly Lys Leu Asn Leu Met Lys Glu Val Ile Cys Ile
    290                 295                 300

Pro His Pro Glu Leu Thr Thr Lys Gln Gly Val Glu Met Leu Met Glu
305                 310                 315                 320

Met Gln Lys His Ile Asn Lys Ile Ile Glu Met Met Pro Pro Ser Pro
                325                 330                 335

Pro Lys Ala Glu Thr Lys Lys Gly His Asp Gly Ser Lys Arg Gly Gln
            340                 345                 350

Gln Gln Ile Thr Gly Lys Met Ser His Leu Gly Cys Leu Thr Ile Asn
        355                 360                 365

Cys Asp Ser Ile Glu Gln Pro Leu Leu Ile Gln Glu Ile Cys Ala
    370                 375                 380

Asn Leu Gly Leu Glu Leu Gly Thr Asn Leu His Leu Ala Ile Asn Cys
385                 390                 395                 400

```
Ala Gly His Glu Leu Met Asp Tyr Asn Lys Gly Lys Tyr Glu Val Ile
            405                 410                 415

Met Gly Thr Tyr Lys Asn Ala Ala Glu Met Val Asp Leu Tyr Val Asp
        420                 425                 430

Leu Ile Asn Lys Tyr Pro Ser Ile Ile Ala Leu Ile Asp Pro Phe Arg
        435                 440                 445

Lys Glu Asp Ser Glu Gln Trp Asp Ser Ile Tyr His Ala Leu Gly Ser
    450                 455                 460

Arg Cys Tyr Ile Ile Ala Gly Thr Ala Ser Lys Ser Ile Ser Lys Leu
465                 470                 475                 480

Leu Glu Gln Gly Asn Ile Ser Ile Pro Lys Ser Asn Gly Leu Ile Ile
                485                 490                 495

Lys His Thr Asn Gln Thr Thr Met Ser Asp Leu Val Glu Ile Thr Asn
                500                 505                 510

Leu Ile Asp Ser Lys Lys His Ile Thr Val Phe Gly Ser Thr Glu Gly
            515                 520                 525

Glu Ser Ser Asp Asp Ser Leu Val Asp Leu Ala Val Gly Leu Gly Val
    530                 535                 540

Arg Phe Ile Lys Leu Gly Gly Leu Ser Arg Gly Glu Arg Val Thr Lys
545                 550                 555                 560

Tyr Asn Arg Leu Leu Thr Ile Glu Glu Glu Leu Val Gln Asn Gly Thr
                565                 570                 575

Leu Gly Phe Lys Glu Glu His Thr Phe Phe Tyr Phe Asn Glu Glu Ala
            580                 585                 590

Glu Lys Ala Ala Glu Ala Leu Glu Ala Ala Ala Arg Glu Pro Leu
    595                 600                 605

Val Pro Thr Phe Pro Thr Gln Gly Val Glu Glu Ser Ala Glu Thr Gly
    610                 615                 620

Ala Ser Ser Gly
625

<210> SEQ ID NO 65
<211> LENGTH: 434
<212> TYPE: PRT
<213> ORGANISM: Homo sapiens

<400> SEQUENCE: 65

Met Ser Ile Leu Lys Ile His Ala Arg Glu Ile Phe Asp Ser Arg Gly
1               5                  10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140
```

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
            165                 170                 175

Asn Phe Arg Glu Ala Met Arg Ile Gly Ala Glu Val Tyr His Asn Leu
        180                 185                 190

Lys Asn Val Ile Lys Glu Lys Tyr Gly Lys Asp Ala Thr Asn Val Gly
    195                 200                 205

Asp Glu Gly Gly Phe Ala Pro Asn Ile Leu Glu Asn Lys Glu Gly Leu
210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys

<210> SEQ ID NO 66
<211> LENGTH: 434
<212> TYPE: PRT
<213> ORGANISM: Homo sapiens

<400> SEQUENCE: 66

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gly Arg Tyr Leu Gly Lys Gly Val Leu Lys
    50                  55                  60

Ala Val Glu Asn Ile Asn Asn Thr Leu Gly Pro Ala Leu Leu Gln Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Glu Lys Gly Val
        115                 120                 125

Pro Leu Tyr Arg His Ile Ala Asp Leu Ala Gly Asn Pro Asp Leu Ile
        130                 135                 140

Leu Pro Val Pro Ala Phe Asn Val Ile Asn Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Pro Ala Arg His Ile Thr
            260                 265                 270

Gly Glu Lys Leu Gly Glu Leu Tyr Lys Ser Phe Ile Lys Asn Tyr Pro
        275                 280                 285

Val Val Ser Ile Glu Asp Pro Phe Asp Gln Asp Asp Trp Ala Thr Trp
    290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Ile Phe Ala Gly Arg Lys Phe Arg Asn Pro Lys
            420                 425                 430

Ala Lys

<210> SEQ ID NO 67
<211> LENGTH: 434
<212> TYPE: PRT
<213> ORGANISM: Homo sapiens

<400> SEQUENCE: 67

Met Ser Ile Glu Lys Ile Trp Ala Arg Glu Ile Leu Asp Ser Arg Gly
1               5                   10                  15

```
Asn Pro Thr Val Glu Val Asp Leu Tyr Thr Ala Lys Gly Leu Phe Arg
             20                  25                  30

Ala Ala Val Pro Ser Gly Ala Ser Thr Gly Ile Tyr Glu Ala Leu Glu
         35                  40                  45

Leu Arg Asp Gly Asp Lys Gln Arg Tyr Leu Gly Lys Gly Val Leu Lys
     50                  55                  60

Ala Val Asp His Ile Asn Ser Thr Ile Ala Pro Ala Leu Ile Ser Ser
 65                  70                  75                  80

Gly Leu Ser Val Val Glu Gln Glu Lys Leu Asp Asn Leu Met Leu Glu
                 85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Thr Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430
```

Val Leu

<210> SEQ ID NO 68
<211> LENGTH: 430
<212> TYPE: PRT
<213> ORGANISM: Artificial Sequence
<220> FEATURE:
<223> OTHER INFORMATION: ENO Consensus sequence

<400> SEQUENCE: 68

Met Ser Ile Lys Ile Phe Ala Arg Glu Ile Leu Asp Ser Arg Gly Asn
1               5                   10                  15

Pro Thr Val Glu Val Asp Leu Phe Thr Ala Lys Gly Leu Phe Arg Ala
            20                  25                  30

Ala Val Pro Ser Gly Ala Ser Thr Gly Ile Tyr Glu Ala Leu Glu Leu
        35                  40                  45

Arg Asp Gly Asp Lys Ala Arg Tyr Leu Gly Lys Gly Val Ser Lys Ala
    50                  55                  60

Val Glu His Ile Asn Ser Thr Ile Ala Pro Ala Leu Ile Ser Lys Lys
65                  70                  75                  80

Leu Ser Val Val Glu Gln Glu Lys Leu Asp Lys Leu Met Ile Glu Leu
                85                  90                  95

Asp Gly Thr Glu Asn Lys Ser Lys Phe Gly Ala Asn Ala Ile Leu Gly
            100                 105                 110

Val Ser Leu Ala Val Cys Lys Ala Gly Ala Ala Glu Lys Gly Val Pro
        115                 120                 125

Leu Tyr Arg His Ile Ala Asp Leu Ala Gly Asn Ser Asp Leu Ile Leu
    130                 135                 140

Pro Val Pro Ala Phe Asn Val Ile Asn Gly Gly Ser His Ala Gly Asn
145                 150                 155                 160

Lys Leu Ala Met Gln Glu Phe Met Ile Leu Pro Val Gly Ala Ala Ser
                165                 170                 175

Phe Lys Glu Ala Met Arg Ile Gly Ala Glu Val Tyr His His Leu Lys
            180                 185                 190

Gly Val Ile Lys Asp Lys Tyr Gly Lys Asp Ala Thr Asn Val Gly Asp
        195                 200                 205

Glu Gly Gly Phe Ala Pro Asn Ile Leu Glu Asn Glu Ala Leu Glu Leu
    210                 215                 220

Leu Lys Thr Ala Ile Asn Lys Ala Gly Tyr Thr Asp Lys Val Val Ile
225                 230                 235                 240

Gly Met Asp Val Ala Ala Ser Glu Phe Tyr Arg Gly Lys Tyr Asp Leu
                245                 250                 255

Asp Phe Lys Ser Pro Asp Asp Pro Ser Arg Tyr Ile Thr Gly Asp Gln
            260                 265                 270

Leu Gly Asp Leu Tyr Lys Ser Phe Ile Lys Asp Tyr Pro Val Val Ser
        275                 280                 285

Ile Glu Asp Pro Phe Asp Gln Asp Asp Trp Ala Ala Trp Ser Ser Phe
    290                 295                 300

Thr Ala Ala Val Gly Ile Gln Ile Val Gly Asp Asp Leu Thr Val Thr
305                 310                 315                 320

Asn Pro Lys Arg Ile Ala Lys Ala Val Glu Glu Lys Ala Cys Asn Cys
                325                 330                 335

Leu Leu Leu Lys Val Asn Gln Ile Gly Ser Val Thr Glu Ser Ile Gln
            340                 345                 350

Ala Cys Lys Leu Ala Gln Ser Asn Gly Trp Gly Val Met Val Ser His

```
                355                 360                 365
Arg Ser Gly Glu Thr Glu Asp Thr Phe Ile Ala Asp Leu Val Val Gly
370                 375                 380

Leu Cys Thr Gly Gln Ile Lys Thr Gly Ala Pro Cys Arg Ser Glu Arg
385                 390                 395                 400

Leu Ala Lys Tyr Asn Gln Leu Leu Arg Ile Glu Glu Leu Gly Asp
                405                 410                 415

Lys Ala Lys Phe Ala Gly Arg Asn Phe Arg Asn Pro Ala Lys
                420                 425                 430

<210> SEQ ID NO 69
<211> LENGTH: 434
<212> TYPE: PRT
<213> ORGANISM: Mouse

<400> SEQUENCE: 69

Met Ser Ile Leu Arg Ile His Ala Arg Glu Ile Phe Asp Ser Arg Gly
1               5                   10                  15

Asn Pro Thr Val Glu Val Asp Leu Tyr Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Phe Met Gly Lys Gly Val Ser Gln
        50                  55                  60

Ala Val Glu His Ile Asn Lys Thr Ile Ala Pro Ala Leu Val Ser Lys
65              70                  75                  80

Lys Val Asn Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
                100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Pro Glu Val Ile
        130                 135                 140

Leu Pro Val Pro Ala Phe Asn Val Ile Asn Gly Gly Ser His Ala Gly
145             150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
210                 215                 220

Glu Leu Leu Lys Thr Ala Ile Ala Lys Ala Gly Tyr Thr Asp Gln Val
225                 230                 235                 240

Val Ile Gly Met Asp Val Ala Ala Ser Glu Phe Tyr Arg Ser Gly Lys
                245                 250                 255

Tyr Asp Leu Asp Phe Lys Ser Pro Asp Asp Pro Ser Arg Tyr Ile Thr
            260                 265                 270

Pro Asp Gln Leu Ala Asp Leu Tyr Lys Ser Phe Val Gln Asn Tyr Pro
        275                 280                 285

Val Val Ser Ile Glu Asp Pro Phe Asp Gln Asp Asp Trp Gly Ala Trp
    290                 295                 300
```

```
Gln Lys Phe Thr Ala Ser Ala Gly Ile Gln Val Gly Asp Asp Leu
305                 310                 315                 320

Thr Val Thr Asn Pro Lys Arg Ile Ala Lys Ala Ser Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Ile Leu Arg Ile Glu Glu Glu
            405                 410                 415

Leu Gly Ser Lys Ala Lys Phe Ala Gly Arg Ser Phe Arg Asn Pro Leu
        420                 425                 430

Ala Lys

<210> SEQ ID NO 70
<211> LENGTH: 434
<212> TYPE: PRT
<213> ORGANISM: Rat

<400> SEQUENCE: 70

Met Ser Ile Leu Lys Ile His Ala Arg Glu Ile Phe Asp Ser Arg Gly
1               5                   10                  15

Asn Pro Thr Val Glu Val Asp Leu Tyr Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Phe Met Gly Lys Gly Val Ser Lys
50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Gln Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Pro Glu Val Ile
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
210                 215                 220

Glu Leu Leu Lys Ser Ala Ile Ala Lys Ala Gly Tyr Thr Asp Gln Val
225                 230                 235                 240
```

```
Val Ile Gly Met Asp Val Ala Ala Ser Glu Phe Tyr Arg Ala Gly Lys
                245                 250                 255

Tyr Asp Leu Asp Phe Lys Ser Pro Asp Ala Ser Arg Tyr Ile Thr
        260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Trp Asp Ala Trp
290                 295                 300

Gln Lys Phe Thr Ala Thr Ala Gly Ile Gln Val Val Gly Asp Asp Leu
305                 310                 315                 320

Thr Val Thr Asn Pro Lys Arg Ile Ala Lys Ala Gly Glu Lys Ser
                325                 330                 335

Cys Asn Cys Leu Leu Leu Lys Val Asn Gln Ile Gly Ser Val Thr Glu
                340                 345                 350

Ser Leu Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Ile Leu Arg Ile Glu Glu Glu
                405                 410                 415

Leu Gly Ser Lys Ala Lys Phe Ala Gly Arg Ser Phe Arg Asn Pro Leu
                420                 425                 430

Ala Lys

<210> SEQ ID NO 71
<211> LENGTH: 434
<212> TYPE: PRT
<213> ORGANISM: Bovin

<400> SEQUENCE: 71

Met Ser Ile Leu Lys Val His Ala Arg Glu Ile Phe Asp Ser Arg Gly
1               5                   10                  15

Asn Pro Thr Val Glu Val Asp Leu Phe Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ala Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175
```

```
Asn Phe Arg Glu Ala Met Arg Ile Gly Ala Glu Val Tyr His Asn Leu
                180                 185                 190

Lys Asn Val Ile Lys Glu Lys Tyr Gly Lys Asp Ala Thr Asn Val Gly
            195                 200                 205

Asp Glu Gly Gly Phe Ala Pro Asn Ile Leu Glu Asn Lys Glu Ala Leu
        210                 215                 220

Glu Leu Leu Lys Asn Ala Ile Gly Lys Ala Gly Tyr Ser Asp Lys Val
225                 230                 235                 240

Val Ile Gly Met Asp Val Ala Ala Ser Glu Phe Tyr Arg Ser Gly Lys
                245                 250                 255

Tyr Asp Leu Asp Phe Lys Ser Pro Asp Asp Pro Ser Arg Tyr Ile Thr
                260                 265                 270

Pro Asp Glu Leu Ala Asn Leu Tyr Lys Ser Phe Ile Arg Asp Tyr Pro
            275                 280                 285

Val Val Ser Ile Glu Asp Pro Phe Asp Gln Asp Asp Trp Glu Ala Trp
        290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Ser Glu Lys Ser
                325                 330                 335

Cys Asn Cys Leu Leu Leu Lys Val Asn Gln Ile Gly Ser Val Thr Glu
                340                 345                 350

Ser Leu Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Val Ala Pro Cys Arg
385                 390                 395                 400

Ser Glu Arg Leu Ala Lys Tyr Asn Gln Ile Leu Arg Ile Glu Glu Glu
                405                 410                 415

Leu Gly Ser Lys Ala Lys Phe Ala Gly Arg Ser Phe Arg Asn Pro Leu
            420                 425                 430

Ala Lys

<210> SEQ ID NO 72
<211> LENGTH: 434
<212> TYPE: PRT
<213> ORGANISM: Pig

<400> SEQUENCE: 72

Met Ser Ile Leu Lys Ile His Ala Arg Glu Ile Phe Asp Ser Arg Gly
1               5                   10                  15

Asn Pro Thr Val Glu Val Asp Leu His Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
        50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
                100                 105                 110
```

Gly Val Ser Leu Ala Val Cys Lys Ala Gly Ala Val Glu Lys Gly Val
                115                 120                 125

Pro Leu Tyr Arg His Ile Ala Asp Leu Ala Gly Asn Ala Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Thr Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
                195                 200                 205

Asp Glu Gly Gly Phe Ala Pro Asn Ile Leu Glu Asn Lys Glu Ala Leu
    210                 215                 220

Glu Leu Leu Lys Asn Ala Ile Gly Lys Ala Gly Tyr Thr Asp Lys Val
225                 230                 235                 240

Val Ile Gly Met Asp Val Ala Ala Ser Glu Phe Tyr Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Arg Asp Tyr Pro
    275                 280                 285

Val Val Ser Ile Glu Asp Pro Phe Asp Gln Asp Asp Trp Glu Ala Trp
290                 295                 300

Gln Lys Phe Thr Gly Ser Ala Gly Ile Gln Val Val Gly Asp Asp Leu
305                 310                 315                 320

Thr Val Thr Asn Pro Lys Arg Ile Ser Lys Ala Val Ala Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ser Asn Gly Trp Gly Val Met
    355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Ile Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys

<210> SEQ ID NO 73
<211> LENGTH: 434
<212> TYPE: PRT
<213> ORGANISM: Horse

<400> SEQUENCE: 73

Met Ser Ile Leu Lys Ile His Ala Arg Glu Ile Phe Asp Ser Arg Gly
1               5                   10                  15

Asn Pro Thr Val Glu Val Asp Leu Cys Thr Ser Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
        50                  55                  60
Ala Val Glu His Ile Asn Lys Thr Ile Ala Pro Ala Leu Ile Ser Lys
 65                  70                  75                  80
Lys Leu Ser Val Val Glu Gln Glu Lys Ile Asp Lys Leu Met Ile Glu
                 85                  90                  95
Met Asp Gly Thr Glu Asn Lys Ser Lys Phe Gly Ala Asn Ala Ile Leu
            100                 105                 110
Gly Val Ser Leu Ala Val Cys Lys Ala Gly Ala Val Glu Lys Gly Val
            115                 120                 125
Pro Leu Tyr Arg His Ile Ala Asp Leu Ala Gly Asn Ser Glu Val Ile
        130                 135                 140
Leu Pro Val Pro Ala Phe Asn Val Ile Asn Gly Gly Ser His Ala Gly
145                 150                 155                 160
Asn Lys Leu Ala Met Gln Glu Phe Met Ile Leu Pro Val Gly Ala Ala
                165                 170                 175
Asn Phe Ser Glu Ala Met Arg Ile Gly Ala Glu Val Tyr His Asn Leu
            180                 185                 190
Lys Asn Val Ile Lys Glu Lys Tyr Gly Lys Asp Ala Thr Asn Val Gly
            195                 200                 205
Asp Glu Gly Gly Phe Ala Pro Asn Ile Leu Glu Asn Lys Glu Ala Leu
        210                 215                 220
Glu Leu Leu Lys Asn Ala Ile Gly Lys Ala Gly Tyr Thr Asp Lys Val
225                 230                 235                 240
Val Ile Gly Met Asp Val Ala Ala Ser Glu Phe Phe Arg Ser Gly Lys
                245                 250                 255
Tyr Asp Leu Asp Phe Lys Ser Pro Asp Asp Pro Asn Arg Tyr Ile Thr
            260                 265                 270
Pro Asp Glu Leu Ala Asn Leu Tyr Lys Ser Phe Ile Lys Asp Tyr Pro
        275                 280                 285
Val Val Ser Ile Glu Asp Pro Phe Asp Gln Asp Asp Trp Glu Ala Trp
        290                 295                 300
Gln Lys Phe Thr Ala Ser Ala Gly Ile Gln Val Val Gly Asp Asp Leu
305                 310                 315                 320
Thr Val Thr Asn Pro Lys Arg Ile Ala Lys Ala Val Gly Glu Lys Ser
                325                 330                 335
Cys Asn Cys Leu Leu Leu Lys Val Asn Gln Ile Gly Ser Val Thr Glu
            340                 345                 350
Ser Leu Gln Ala Cys Lys Leu Ala Gln Ser Asn Gly Trp Gly Val Met
        355                 360                 365
Val Ser His Arg Ser Gly Glu Thr Glu Asp Thr Phe Ile Ala Asp Leu
        370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Ile Leu Arg Ile Glu Glu Glu
                405                 410                 415
Leu Gly Ser Lys Ala Lys Phe Ala Gly Arg Asn Phe Arg Asn Pro Leu
            420                 425                 430

Ala Lys

<210> SEQ ID NO 74
<211> LENGTH: 434
<212> TYPE: PRT
<213> ORGANISM: Chicken

<400> SEQUENCE: 74

```
Met Ser Ile Leu Lys Ile His Ala Arg Glu Ile Phe Asp Ser Arg Gly
1               5                   10                  15

Asn Pro Thr Val Glu Val Asp Leu Tyr Thr Asn Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Leu Gly Lys Gly Val Ser Lys
    50                  55                  60

Ala Val Glu His Val Asn Lys Thr Ile Ala Pro Ala Leu Ile Ser Lys
65                  70                  75                  80

Asn Val Asn Val Val Glu Gln Glu Lys Ile Asp Lys Leu Met Leu Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Asp
                165                 170                 175

Thr Phe Lys Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
    210                 215                 220

Glu Leu Leu Lys Thr Ala Ile Gly Lys Ala Gly Tyr Ser Asp Lys Val
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Leu Gly Phe Val Lys Asn Tyr Pro
        275                 280                 285

Val Val Ser Ile Glu Asp Pro Phe Asp Gln Asp Asp Trp Ala Ala Trp
    290                 295                 300

Lys Lys Phe Thr Ala Ser Val Gly Ile Gln Val Val Gly Asp Asp Leu
305                 310                 315                 320

Thr Val Thr Asn Pro Lys Arg Ile Ala Lys Ala Val Glu Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
```

-continued

```
                405                 410                 415
Leu Gly Ser Lys Ala Arg Phe Ala Gly Arg Asn Phe Arg Asn Pro Arg
            420                 425                 430

Ile Asn

<210> SEQ ID NO 75
<211> LENGTH: 434
<212> TYPE: PRT
<213> ORGANISM: Felis

<400> SEQUENCE: 75

Met Ser Ile Leu Lys Val His Ala Arg Glu Ile Phe Asp Ser Arg Gly
1               5                   10                  15

Asn Pro Thr Val Glu Val Asp Leu Tyr Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Ile Ser Lys
65                  70                  75                  80

Lys Leu Ser Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ala Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
    210                 215                 220

Glu Leu Leu Lys Asn Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Pro Ser Arg Tyr Ile Thr
            260                 265                 270

Pro Asp Glu Leu Ala Asn Leu Tyr Lys Ser Phe Ile Arg Asp Tyr Pro
        275                 280                 285

Val Val Ser Ile Glu Asp Pro Phe Asp Gln Asp Asp Trp Glu Ala Trp
    290                 295                 300

Gln Lys Phe Thr Ala Ser Ala Gly Ile Gln Val Gly Asp Asp Leu
305                 310                 315                 320

Thr Val Thr Asn Pro Lys Arg Ile Ser Lys Ala Val Asn Glu Arg Ser
                325                 330                 335

Cys Asn Cys Leu Leu Leu Lys Val Asn Gln Ile Gly Ser Val Thr Glu
```

```
                    340                 345                 350
Ser Leu Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Ile Leu Arg Ile Glu Glu Glu
                405                 410                 415

Leu Gly Ser Lys Ala Lys Phe Ala Gly Arg Ser Phe Arg Asn Pro Leu
            420                 425                 430

Ala Lys

<210> SEQ ID NO 76
<211> LENGTH: 447
<212> TYPE: PRT
<213> ORGANISM: Canine
<220> FEATURE:
<221> NAME/KEY: MISC_FEATURE
<222> LOCATION: (197)..(197)
<223> OTHER INFORMATION: Xaa can be any naturally occurring amino acid

<400> SEQUENCE: 76

Met Ser Ile Leu Lys Ile His Ala Arg Glu Ile Phe Asp Ser Arg Gly
1               5                   10                  15

Asn Pro Thr Val Glu Val Asp Leu Tyr Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Ile Ser Lys
65                  70                  75                  80

Lys Val Asn Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Val Ile His Pro Leu Gln Gly Cys Ser His Thr Arg
145                 150                 155                 160

Asn Ser Leu Arg Gly Glu Thr Lys Phe Ser Ile Trp Pro Ser Ala Gly
                165                 170                 175

Gly Arg Phe Gln Gln Val Leu Ala Pro Met Arg Lys Glu Val Leu Asp
            180                 185                 190

Ser Ser Lys Arg Xaa Leu Gly Ser Glu Tyr Leu Val Ile Leu Leu
            195                 200                 205

Glu Leu Pro Ile Trp Gln Leu Leu Lys Gly Thr Phe Phe Ser Thr Cys
    210                 215                 220

Leu Val Ser Asn Pro Val Ala Asn Leu Phe Pro Ala Leu Glu Leu Leu
225                 230                 235                 240

Lys Asn Ala Ile Gly Lys Ala Gly Tyr Thr Asp Lys Val Val Ile Gly
                245                 250                 255
```

Met Asp Val Ala Ala Ser Glu Phe Phe Arg Ser Gly Lys Tyr Asp Leu
                260                 265                 270

Asp Phe Lys Ser Pro Asp Pro Ser Arg Tyr Ile Thr Pro Asp Gln
            275                 280                 285

Leu Ala Asp Leu Tyr Lys Ser Phe Ile Arg Asp Tyr Pro Val Val Ser
            290                 295                 300

Ile Glu Asp Pro Phe Asp Gln Asp Asp Trp Glu Ala Trp Gln Lys Phe
305                 310                 315                 320

Thr Ala Ser Ala Gly Ile Gln Val Val Gly Asp Asp Leu Thr Val Thr
                325                 330                 335

Asn Pro Lys Arg Ile Ser Lys Ala Val Gly Glu Lys Ser Cys Asn Cys
            340                 345                 350

Leu Leu Leu Lys Val Asn Gln Ile Gly Ser Val Thr Glu Ser Leu Gln
            355                 360                 365

Ala Cys Lys Leu Ala Gln Ser Asn Gly Trp Gly Val Met Val Ser His
            370                 375                 380

Arg Ser Gly Glu Thr Glu Asp Thr Phe Ile Ala Asp Leu Val Val Gly
385                 390                 395                 400

Leu Cys Thr Gly Gln Ile Lys Thr Gly Ala Pro Cys Arg Ser Glu Arg
            405                 410                 415

Leu Ala Lys Tyr Asn Gln Ile Leu Arg Ile Glu Glu Glu Leu Gly Ser
            420                 425                 430

Lys Ala Lys Phe Ala Gly Arg Ser Phe Arg Asn Pro Leu Ala Lys
            435                 440                 445

<210> SEQ ID NO 77
<211> LENGTH: 434
<212> TYPE: PRT
<213> ORGANISM: Rabbit

<400> SEQUENCE: 77

Met Ser Val Leu Lys Val His Ala Arg Glu Ile Phe Asp Ser Arg Gly
1               5                   10                  15

Asn Pro Thr Val Glu Val Asp Leu Tyr Thr Ser Lys Gly Leu Phe Arg
            20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
            50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Lys Leu Met Ile Glu
            85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Ser Glu Val Ile
            130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Ile Gly Ala Ala
            165                 170                 175

Ser Phe Arg Glu Ala Met Arg Ile Gly Ala Glu Val Tyr His Asn Leu
            180                 185                 190

-continued

Lys Asn Val Ile Lys Glu Lys Tyr Gly Lys Asp Ala Thr Asn Val Gly
            195                 200                 205

Asp Glu Gly Gly Phe Ala Pro Asn Ile Leu Glu Asn Lys Glu Ala Leu
210                 215                 220

Glu Leu Leu Lys Asn Ala Ile Ala Lys Ala Gly Tyr Thr Asp Lys Val
225                 230                 235                 240

Val Ile Gly Met Asp Val Ala Ala Ser Glu Phe Phe Arg Ser Gly Lys
            245                 250                 255

Tyr Asp Leu Asp Phe Lys Ser Pro Asp Asp Ala Ser Arg Tyr Ile Thr
            260                 265                 270

Pro Asp Gln Leu Ala Asp Leu Tyr Lys Ser Phe Val Arg Asp Tyr Pro
            275                 280                 285

Val Val Ser Ile Glu Asp Pro Phe Asp Gln Asp Trp Glu Ala Trp
            290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asp Gln Lys Ser
            325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
            370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
            405                 410                 415

Leu Gly Ser Lys Ala Lys Phe Ala Gly Arg Asn Phe Arg Asn Pro Leu
            420                 425                 430

Ala Lys

<210> SEQ ID NO 78
<211> LENGTH: 443
<212> TYPE: PRT
<213> ORGANISM: Sheep

<400> SEQUENCE: 78

Met Ser Ile Leu Lys Val His Ala Arg Glu Ile Phe Asp Ser Arg Gly
1               5                   10                  15

Asn Pro Thr Val Glu Val Asp Leu Phe Thr Ala Lys Gly Leu Phe Arg
            20                  25                  30

Ala Ala Val Pro Ser Gly Ala Ser Thr Gly Ile Tyr Glu Ala Leu Glu
            35                  40                  45

Leu Arg Asp Asn Asp Lys Thr Arg Tyr Met Gly Lys Gly Val Ser Lys
        50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Lys Leu Met Ile Glu
            85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Ala Glu Val Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
    210                 215                 220

Glu Leu Leu Lys Asn Ala Ile Gly Lys Ala Gly Tyr Ser Asp Lys Val
225                 230                 235                 240

Val Ile Gly Met Asp Val Ala Ala Ser Glu Phe Tyr Arg Ser Gly Lys
                245                 250                 255

Tyr Asp Leu Asp Phe Lys Ser Pro Asp Pro Asn Arg Tyr Ile Thr
            260                 265                 270

Pro Asp Glu Leu Ala Asp Leu Tyr Lys Ser Phe Ile Arg Asp Tyr Pro
        275                 280                 285

Val Val Ser Ile Glu Asp Pro Phe Asp Gln Asp Asp Trp Glu Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Ser Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Ile Leu Arg Ile Glu Glu Glu
                405                 410                 415

Leu Gly Ser Lys Ala Lys Phe Ala Gly Arg Ser Phe Arg Ser Gly Arg
            420                 425                 430

Arg Ala Ser Pro Cys Ser His Ser Leu Ala Pro
        435                 440

<210> SEQ ID NO 79
<211> LENGTH: 432
<212> TYPE: PRT
<213> ORGANISM: Artificial Sequence
<220> FEATURE:
<223> OTHER INFORMATION: ENOA Consensus sequence

<400> SEQUENCE: 79

Met Ser Ile Leu Lys Ile His Ala Arg Glu Ile Phe Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
50                  55                  60

Ala Val Glu His Ile Asn Lys Thr Ile Ala Pro Ala Leu Val Ser Lys
65                  70                  75                  80

Lys Leu Asn Val Val Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
            115                 120                 125

Pro Leu Tyr Arg His Ile Ala Asp Leu Ala Gly Asn Ala Glu Val Ile
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Phe Arg Glu Ala Met Arg Ile Gly Ala Glu Val Tyr His Asn Leu Lys
            180                 185                 190

Asn Val Ile Lys Glu Lys Tyr Gly Lys Asp Ala Thr Asn Val Gly Asp
            195                 200                 205

Glu Gly Gly Phe Ala Pro Asn Ile Leu Glu Asn Lys Glu Ala Leu Glu
210                 215                 220

Leu Leu Lys Asn Ala Ile Gly Lys Ala Gly Tyr Thr Asp Lys Val Val
225                 230                 235                 240

Ile Gly Met Asp Val Ala Ala Ser Glu Phe Tyr Arg Ser Gly Lys Tyr
                245                 250                 255

Asp Leu Asp Phe Lys Ser Pro Asp Asp Pro Ser Arg Tyr Ile Thr Pro
            260                 265                 270

Asp Gln Leu Ala Asp Leu Tyr Lys Ser Phe Ile Arg Asp Tyr Pro Val
            275                 280                 285

Val Ser Ile Glu Asp Pro Phe Asp Gln Asp Asp Trp Glu Ala Trp Gln
290                 295                 300

Lys Phe Thr Ala Ser Ala Gly Ile Gln Val Val Gly Asp Asp Leu Thr
305                 310                 315                 320

Val Thr Asn Pro Lys Arg Ile Ala Lys Ala Val Glu Lys Ser Cys Asn
                325                 330                 335

Cys Leu Leu Leu Lys Val Asn Gln Ile Gly Ser Val Thr Glu Ser Leu
            340                 345                 350

Gln Ala Cys Lys Leu Ala Gln Ser Asn Gly Trp Gly Val Met Val Ser
            355                 360                 365

His Arg Ser Gly Glu Thr Glu Asp Thr Phe Ile Ala Asp Leu Val Val
370                 375                 380

Gly Leu Cys Thr Gly Gln Ile Lys Thr Gly Ala Pro Cys Arg Ser Glu
385                 390                 395                 400

Arg Leu Ala Lys Tyr Asn Gln Ile Leu Arg Ile Glu Glu Glu Leu Gly
                405                 410                 415

Ser Lys Ala Lys Phe Ala Gly Arg Ser Phe Arg Asn Pro Leu Ala Lys
            420                 425                 430

<210> SEQ ID NO 80
<211> LENGTH: 434
<212> TYPE: PRT
<213> ORGANISM: Mouse

<400> SEQUENCE: 80

```
Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Ala Arg Tyr Leu Gly Lys Gly Val Leu Lys
    50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Asp Leu Val
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Pro Ala Arg His Ile Ser
            260                 265                 270

Gly Glu Lys Leu Gly Glu Leu Tyr Lys Asn Phe Ile Gln Asn Tyr Pro
        275                 280                 285

Val Val Ser Ile Glu Asp Pro Phe Asp Gln Asp Asp Trp Ala Thr Trp
    290                 295                 300

Thr Ser Phe Leu Ser Gly Val Asp Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415
```

Leu Gly Asp Lys Ala Val Phe Ala Gly Arg Lys Phe Arg Asn Pro Lys
            420                 425                 430

Ala Lys

<210> SEQ ID NO 81
<211> LENGTH: 434
<212> TYPE: PRT
<213> ORGANISM: Rat

<400> SEQUENCE: 81

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Ser Arg Tyr Leu Gly Lys Gly Val Leu Lys
    50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Asp Leu Val
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Pro Ala Arg His Ile Ser
            260                 265                 270

Gly Glu Lys Leu Gly Glu Leu Tyr Lys Ser Phe Ile Lys Asn Tyr Pro
        275                 280                 285

Val Val Ser Ile Glu Asp Pro Phe Asp Gln Asp Asp Trp Ala Thr Trp
    290                 295                 300

Thr Ser Phe Leu Ser Gly Val Asp Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
            340                 345                 350

```
Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Ala
        405                 410                 415

Leu Gly Asp Lys Ala Val Phe Ala Gly Arg Lys Phe Arg Asn Pro Lys
        420                 425                 430

Ala Lys

<210> SEQ ID NO 82
<211> LENGTH: 434
<212> TYPE: PRT
<213> ORGANISM: Bovine

<400> SEQUENCE: 82

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Ser Arg Tyr Leu Gly Lys Gly Val Leu Lys
        50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Glu Leu Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
        210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Asp Pro Ala Arg His Ile Ser
            260                 265                 270

Gly Glu Lys Leu Gly Glu Leu Tyr Lys Asn Phe Ile Lys Asn Tyr Pro
        275                 280                 285
```

```
Val Val Ser Ile Glu Asp Pro Phe Asp Gln Asp Trp Ala Thr Trp
    290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
                340                 345                 350

Ser Ile Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Val Phe Ala Gly Arg Lys Phe Arg Asn Pro Lys
                420                 425                 430

Ala Lys

<210> SEQ ID NO 83
<211> LENGTH: 434
<212> TYPE: PRT
<213> ORGANISM: Pig

<400> SEQUENCE: 83

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Ser Arg Tyr Leu Gly Lys Gly Val Leu Lys
        50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Lys Gly Val
            115                 120                 125

Pro Leu Tyr Arg His Ile Ala Asp Leu Ala Gly Asn Pro Asp Leu Val
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His His Leu
                180                 185                 190

Lys Gly Val Ile Lys Gly Lys Tyr Gly Lys Asp Ala Thr Asn Val Gly
            195                 200                 205

Asp Glu Gly Gly Phe Ala Pro Asn Ile Leu Glu Asn Asn Glu Ala Leu
        210                 215                 220
```

```
Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
            245                 250                 255

Tyr Asp Leu Asp Phe Lys Ser Pro Asp Pro Ser Arg His Ile Thr
        260                 265                 270

Gly Glu Lys Leu Gly Glu Leu Tyr Lys Ser Phe Ile Lys Asn Tyr Pro
            275                 280                 285

Val Val Ser Ile Glu Asp Pro Phe Asp Gln Asp Trp Lys Thr Trp
290                 295                 300

Thr Ser Phe Leu Ser Gly Val Asn Ile Gln Ile Val Gly Asp Asp Leu
305                 310                 315                 320

Thr Val Thr Asn Leu Lys Arg Ile Ala Gln Ala Val Glu Lys Lys Ala
            325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
            370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Val Phe Ala Gly Arg Lys Phe Arg Asn Pro Lys
            420                 425                 430

Ala Lys

<210> SEQ ID NO 84
<211> LENGTH: 434
<212> TYPE: PRT
<213> ORGANISM: Horse

<400> SEQUENCE: 84

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Ser Arg Tyr Leu Gly Lys Gly Val Leu Lys
50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Asp Leu Val
    130                 135                 140

Leu Pro Val Pro Ala Phe Asn Val Ile Asn Gly Gly Ser His Ala Gly
145                 150                 155                 160
```

Asn Lys Leu Ala Met Gln Glu Phe Met Ile Leu Pro Val Gly Ala Ser
              165                 170                 175

Ser Phe Lys Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Pro Ala Arg His Ile Thr
            260                 265                 270

Gly Glu Lys Leu Gly Glu Leu Tyr Lys Asn Phe Ile Lys Asn Tyr Pro
        275                 280                 285

Val Val Ser Ile Glu Asp Pro Phe Asp Gln Asp Asp Trp Ala Thr Trp
    290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Gln Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Val Phe Ala Gly Arg Lys Phe Arg Asn Pro Lys
            420                 425                 430

Ala Lys

<210> SEQ ID NO 85
<211> LENGTH: 434
<212> TYPE: PRT
<213> ORGANISM: Chicken

<400> SEQUENCE: 85

Met Ser Ile Gln Lys Ile His Ala Arg Glu Ile Leu Asp Ser Arg Gly
1               5                   10                  15

Glu Pro Thr Val Glu Val Asp Leu His Thr Ala Lys Gly His Phe Arg
            20                  25                  30

Ala Ala Val Pro Ser Gly Ala Ser Thr Gly Ile His Glu Ala Leu Glu
        35                  40                  45

Pro Arg Asp Gly Asp Lys Lys Arg Phe Leu Gly Lys Gly Val Leu Lys
    50                  55                  60

Ala Val Glu His Ile Asn Lys Thr Ile Gly Pro Ala Leu Ile Glu Lys
65                  70                  75                  80

Lys Ile Ser Val Val Glu Gln Glu Lys Ile Asp Lys Val Met Ile Glu
                85                  90                  95

```
Met Asp Gly Thr Glu Asn Lys Ser Lys Phe Gly Ala Asn Ala Ile Leu
              100                 105                 110

Gly Val Ser Leu Ala Val Cys Lys Ala Gly Ala Ala Glu Lys Gly Val
              115                 120                 125

Pro Leu Tyr Arg His Ile Ala Asp Leu Ala Gly Asn Thr Glu Leu Ile
              130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Val Leu Pro Val Gly Ala Ala
              165                 170                 175

Ser Phe His Asp Ala Met Arg Val Gly Ala Glu Val Tyr His Ser Leu
              180                 185                 190

Lys Gly Val Ile Lys Ala Lys Tyr Gly Lys Asp Ala Thr Asn Val Gly
              195                 200                 205

Gly Glu Gly Gly Phe Ala Pro Asn Ile Leu Asp Asn His Glu Ala Leu
              210                 215                 220

Glu Leu Leu Lys Ala Ala Ile Ala Gln Ala Gly Tyr Thr Asp Lys Val
225                 230                 235                 240

Val Ile Gly Met Asp Val Ala Ala Ser Glu Phe Cys Arg Asp Gly Arg
              245                 250                 255

Tyr His Leu Asp Phe Lys Ser Pro Pro His Thr Lys Arg Tyr Ile Thr
              260                 265                 270

Gly Glu Gln Leu Gly Glu Ile Tyr Arg Gly Phe Ile Lys Asp Tyr Pro
              275                 280                 285

Val Val Ser Ile Glu Asp Pro Phe Asp Gln Asp Asp Trp Glu Ala Trp
              290                 295                 300

Lys Arg Phe Val Phe His Val Asp Ile Gln Val Val Gly Asp Asp Leu
305                 310                 315                 320

Thr Val Thr Asn Pro Lys Arg Ile Ala His Gly Ala Glu Gln His Ala
              325                 330                 335

Cys Asn Cys Leu Leu Leu Lys Val Asn Gln Ile Gly Ser Val Thr Glu
              340                 345                 350

Ser Ile Gln Ala Cys Lys Leu Ala Gln Ser His Gly Trp Gly Val Met
              355                 360                 365

Val Ser His Arg Ser Gly Glu Thr Glu Asp Thr Phe Ile Ala Asp Leu
              370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
              405                 410                 415

Leu Gly Asp Lys Ala Lys Phe Ala Gly Arg Lys Phe Arg Asn Pro Lys
              420                 425                 430

Ala Lys

<210> SEQ ID NO 86
<211> LENGTH: 434
<212> TYPE: PRT
<213> ORGANISM: Felis

<400> SEQUENCE: 86

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
              20                  25                  30
```

```
Ala Ala Val Pro Ser Gly Ala Ser Thr Gly Ile Tyr Glu Ala Leu Glu
        35                  40                  45

Leu Arg Asp Gly Asp Lys Ser Arg Tyr Leu Gly Lys Gly Val Leu Lys
 50                  55                  60

Ala Val Glu His Ile Asn Lys Thr Leu Gly Pro Ala Leu Leu Glu Lys
 65                  70                  75                  80

Lys Leu Ser Val Val Asp Gln Glu Lys Val Asp Lys Phe Met Ile Glu
                 85                  90                  95

Leu Asp Gly Thr Glu Asn Lys Ser Lys Phe Gly Ala Asn Ala Ile Leu
            100                 105                 110

Gly Ile Ser Leu Ala Val Cys Lys Ala Gly Ala Ala Glu Lys Gly Val
            115                 120                 125

Pro Leu Tyr Arg His Ile Ala Asp Leu Ala Gly Asn Pro Asp Leu Val
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
            195                 200                 205

Asp Glu Gly Gly Phe Ala Pro Asn Ile Leu Glu Asn Asn Glu Ala Leu
        210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Asp Pro Ala Arg His Ile Thr
            260                 265                 270

Gly Glu Lys Leu Gly Glu Leu Tyr Lys Asn Phe Ile Lys Asn Tyr Pro
            275                 280                 285

Val Val Ser Ile Glu Asp Pro Phe Asp Gln Asp Asp Trp Ala Thr Trp
        290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
            355                 360                 365

Val Ser His Arg Ser Gly Glu Thr Glu Asp Thr Phe Ile Ala Asp Leu
        370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asn Lys Ala Val Phe Ala Gly Arg Lys Phe Arg Asn Pro Lys
            420                 425                 430

Ala Lys
```

<210> SEQ ID NO 87
<211> LENGTH: 434
<212> TYPE: PRT
<213> ORGANISM: Canine

<400> SEQUENCE: 87

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Ser Arg Tyr Leu Gly Lys Gly Val Leu Lys
    50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Asp Leu Val
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe Tyr Arg Asn Gly Lys
                245                 250                 255

Tyr Asp Leu Asp Phe Lys Ser Pro Asp Pro Ala Arg His Ile Thr
            260                 265                 270

Gly Glu Lys Leu Gly Glu Leu Tyr Lys Ser Phe Ile Lys Asn Tyr Pro
        275                 280                 285

Val Val Ser Ile Glu Asp Pro Phe Asp Gln Asp Trp Ala Thr Trp
    290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

```
Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
            405                 410                 415

Leu Gly Asp Lys Ala Val Phe Ala Gly Arg Lys Phe Arg Asn Pro Lys
            420                 425                 430

Ala Lys

<210> SEQ ID NO 88
<211> LENGTH: 434
<212> TYPE: PRT
<213> ORGANISM: Rabbit

<400> SEQUENCE: 88

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
            35                  40                  45

Leu Arg Asp Gly Asp Lys Ser Arg Tyr Leu Gly Lys Gly Val Leu Lys
50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
            115                 120                 125

Pro Leu Tyr Arg His Ile Ala Asp Leu Ala Gly Asn His Asp Leu Val
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Arg Glu Ala Met Arg Ile Gly Ala Glu Val Tyr His His Leu
            180                 185                 190

Lys Gly Val Ile Lys Ala Lys Tyr Gly Lys Asp Ala Thr Asn Val Gly
            195                 200                 205

Asp Glu Gly Gly Phe Ala Pro Asn Ile Leu Glu Asn Asn Glu Ala Leu
210                 215                 220

Glu Leu Leu Lys Thr Ala Ile Gln Ala Ala Gly Tyr Pro Asp Lys Val
225                 230                 235                 240

Val Ile Gly Met Asp Val Ala Ala Ser Glu Phe His Arg Asn Gly Lys
                245                 250                 255

Tyr Asp Leu Asp Phe Lys Ser Pro Asp Pro Ala Arg His Ile Thr
            260                 265                 270

Gly Gln Lys Leu Gly Glu Leu Tyr Lys Ser Phe Ile Lys Asn Tyr Pro
            275                 280                 285

Val Val Ser Ile Glu Asp Pro Phe Asp Gln Asp Asp Trp Ala Thr Trp
290                 295                 300

Thr Ser Phe Leu Ser Gly Val Asp Ile Gln Ile Val Gly Asp Asp Leu
305                 310                 315                 320
```

Thr Val Thr Asn Pro Lys Arg Ile Ala Gln Ala Val Glu Lys Lys Ala
              325                 330                 335
Cys Asn Cys Leu Leu Leu Lys Val Asn Gln Ile Gly Ser Val Thr Glu
              340                 345                 350
Ser Ile Gln Ala Cys Lys Leu Ala Gln Ser Asn Gly Trp Gly Val Met
              355                 360                 365
Val Ser His Arg Ser Gly Glu Thr Glu Asp Thr Phe Ile Ala Asp Leu
              370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Met Arg Ile Glu Glu Ala
              405                 410                 415
Leu Gly Asp Lys Ala Val Phe Ala Gly Arg Lys Phe Arg Asn Pro Lys
              420                 425                 430
Ala Lys

<210> SEQ ID NO 89
<211> LENGTH: 434
<212> TYPE: PRT
<213> ORGANISM: Sheep

<400> SEQUENCE: 89

Met Ala Met Gln Lys Ile Phe Ala Arg Glu Ile Leu Asp Ser Arg Gly
1               5                   10                  15
Asn Pro Thr Val Glu Val Asp Leu His Thr Ala Lys Gly Arg Phe Arg
              20                  25                  30
Ala Ala Val Pro Ser Gly Ala Ser Thr Gly Ile Tyr Glu Ala Leu Glu
              35                  40                  45
Leu Arg Asp Gly Asp Lys Ser Arg Tyr Leu Gly Lys Gly Val Leu Lys
        50                  55                  60
Ala Val Glu His Ile Asn Lys Thr Leu Gly Pro Ala Leu Leu Glu Lys
65                  70                  75                  80
Lys Leu Ser Val Val Asp Gln Glu Lys Val Asp Lys Phe Met Ile Glu
              85                  90                  95
Leu Asp Gly Thr Glu Asn Lys Ser Lys Phe Gly Ala Asn Ala Ile Leu
              100                 105                 110
Gly Val Ser Leu Ala Val Cys Lys Ala Gly Ala Ala Glu Lys Gly Val
              115                 120                 125
Pro Leu Tyr Arg His Ile Ala Asp Leu Ala Gly Asn Pro Glu Leu Ile
        130                 135                 140
Leu Pro Val Pro Ala Phe Asn Val Ile Asn Gly Gly Ser His Ala Gly
145                 150                 155                 160
Asn Lys Leu Ala Met Gln Glu Phe Met Ile Leu Pro Val Gly Ala Ser
              165                 170                 175
Ser Phe Arg Glu Ala Met Arg Ile Gly Ala Glu Val Tyr His His Leu
              180                 185                 190
Lys Gly Val Ile Lys Ala Lys Tyr Gly Lys Asp Ala Thr Asn Val Gly
              195                 200                 205
Asp Glu Gly Gly Phe Ala Pro Asn Ile Leu Glu Asn Asn Glu Ala Leu
        210                 215                 220
Glu Leu Leu Lys Thr Ala Ile Gln Ala Ala Gly Tyr Pro Asp Lys Val
225                 230                 235                 240
Val Ile Gly Met Asp Val Ala Ala Ser Glu Phe Tyr Arg Asn Gly Lys
              245                 250                 255

```
Tyr Asp Leu Asp Phe Lys Ser Pro Asp Pro Ala Arg His Ile Ser
            260                 265                 270

Gly Glu Lys Leu Gly Glu Leu Tyr Lys Ser Phe Ile Lys Asn Tyr Pro
            275                 280                 285

Val Val Ser Ile Glu Asp Pro Phe Asp Gln Asp Trp Ala Thr Trp
            290                 295                 300

Thr Ser Phe Leu Ser Gly Val Asn Ile Gln Ile Val Gly Asp Asp Leu
305                 310                 315                 320

Thr Val Thr Asn Pro Lys Arg Ile Ala Gln Ala Val Glu Lys Lys Ala
                325                 330                 335

Cys Asn Cys Leu Leu Leu Lys Val Asn Gln Ile Gly Ser Val Thr Glu
                340                 345                 350

Ser Ile Gln Ala Cys Lys Leu Ala Gln Ser Asn Gly Trp Gly Val Met
                355                 360                 365

Val Ser His Arg Ser Gly Glu Thr Glu Asp Thr Phe Ile Ala Asp Leu
            370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Ala
                405                 410                 415

Leu Gly Asp Lys Ala Val Phe Ala Gly Arg Lys Phe Arg Asn Pro Lys
                420                 425                 430

Ala Lys

<210> SEQ ID NO 90
<211> LENGTH: 434
<212> TYPE: PRT
<213> ORGANISM: Artificial Sequence
<220> FEATURE:
<223> OTHER INFORMATION: ENOB Consensus sequence

<400> SEQUENCE: 90

Met Ala Met Gln Lys Ile Phe Ala Arg Glu Ile Leu Asp Ser Arg Gly
1               5                   10                  15

Asn Pro Thr Val Glu Val Asp Leu His Thr Ala Lys Gly Arg Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Ser Arg Tyr Leu Gly Lys Gly Val Leu Lys
    50                  55                  60

Ala Val Glu His Ile Asn Lys Thr Leu Gly Pro Ala Leu Leu Glu Lys
65                  70                  75                  80

Lys Leu Ser Val Val Asp Gln Glu Lys Val Asp Lys Phe Met Ile Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Asp Leu Val
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ser
                165                 170                 175

Ser Phe Lys Glu Ala Met Arg Ile Gly Ala Glu Val Tyr His His Leu
```

```
            180                 185                 190
Lys Gly Val Ile Lys Ala Lys Tyr Gly Lys Asp Ala Thr Asn Val Gly
            195                 200                 205
Asp Glu Gly Gly Phe Ala Pro Asn Ile Leu Glu Asn Asn Glu Ala Leu
            210                 215                 220
Glu Leu Leu Lys Thr Ala Ile Gln Ala Ala Gly Tyr Pro Asp Lys Val
225                 230                 235                 240
Val Ile Gly Met Asp Val Ala Ala Ser Glu Phe Tyr Arg Asn Gly Lys
            245                 250                 255
Tyr Asp Leu Asp Phe Lys Ser Pro Asp Pro Ala Arg His Ile Thr
            260                 265                 270
Gly Glu Lys Leu Gly Glu Leu Tyr Lys Ser Phe Ile Lys Asn Tyr Pro
            275                 280                 285
Val Val Ser Ile Glu Asp Pro Phe Asp Gln Asp Asp Trp Ala Thr Trp
            290                 295                 300
Thr Ser Phe Leu Ser Gly Val Asn Ile Gln Ile Val Gly Asp Asp Leu
305                 310                 315                 320
Thr Val Thr Asn Pro Lys Arg Ile Ala Gln Ala Val Glu Lys Lys Ala
            325                 330                 335
Cys Asn Cys Leu Leu Leu Lys Val Asn Gln Ile Gly Ser Val Thr Glu
            340                 345                 350
Ser Ile Gln Ala Cys Lys Leu Ala Gln Ser Asn Gly Trp Gly Val Met
            355                 360                 365
Val Ser His Arg Ser Gly Glu Thr Glu Asp Thr Phe Ile Ala Asp Leu
            370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Met Arg Ile Glu Glu Ala
            405                 410                 415
Leu Gly Asp Lys Ala Val Phe Ala Gly Arg Lys Phe Arg Asn Pro Lys
            420                 425                 430
Ala Lys

<210> SEQ ID NO 91
<211> LENGTH: 434
<212> TYPE: PRT
<213> ORGANISM: Mouse

<400> SEQUENCE: 91

Met Ser Ile Glu Lys Ile Trp Ala Arg Glu Ile Leu Asp Ser Arg Gly
1               5                   10                  15
Asn Pro Thr Val Glu Val Asp Leu Tyr Thr Ala Lys Gly Leu Phe Arg
            20                  25                  30
Ala Ala Val Pro Ser Gly Ala Ser Thr Gly Ile Tyr Glu Ala Leu Glu
            35                  40                  45
Leu Arg Asp Gly Asp Lys Gln Arg Tyr Leu Gly Lys Gly Val Leu Lys
            50                  55                  60
Ala Val Asp His Ile Asn Ser Arg Ile Ala Pro Ala Leu Ile Ser Ser
65                  70                  75                  80
Gly Ile Ser Val Val Glu Gln Glu Lys Leu Asp Asn Leu Met Leu Glu
            85                  90                  95
Leu Asp Gly Thr Glu Asn Lys Ser Lys Phe Gly Ala Asn Ala Ile Leu
            100                 105                 110
Gly Val Ser Leu Ala Val Cys Lys Ala Gly Ala Ala Glu Arg Asp Leu
```

```
            115                 120                 125
Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Met
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asn Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 92
<211> LENGTH: 434
<212> TYPE: PRT
<213> ORGANISM: Rat

<400> SEQUENCE: 92

Met Ser Ile Gln Lys Ile Trp Ala Arg Glu Ile Leu Asp Ser Arg Gly
1               5                   10                  15

Asn Pro Thr Val Glu Val Asp Leu His Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Gln Arg Tyr Leu Gly Lys Gly Val Leu Lys
```

```
                    50                  55                  60
Ala Val Asp His Ile Asn Ser Thr Ile Ala Pro Ala Leu Ile Ser Ser
 65                  70                  75                  80
Gly Leu Ser Val Val Glu Gln Glu Lys Leu Asp Asn Leu Met Leu Glu
                     85                  90                  95
Leu Asp Gly Thr Glu Asn Lys Ser Lys Phe Gly Ala Asn Ala Ile Leu
                100                 105                 110
Gly Val Ser Leu Ala Val Cys Lys Ala Gly Ala Glu Lys Asp Leu
                115                 120                 125
Pro Leu Tyr Arg His Ile Ala Gln Leu Ala Gly Asn Ser Asp Leu Ile
                130                 135                 140
Leu Pro Val Pro Ala Phe Asn Val Ile Asn Gly Gly Ser His Ala Gly
145                 150                 155                 160
Asn Lys Leu Ala Met Gln Glu Phe Met Ile Leu Pro Val Gly Ala Glu
                165                 170                 175
Ser Phe Arg Asp Ala Met Arg Leu Gly Ala Glu Val Tyr His Thr Leu
                180                 185                 190
Lys Gly Val Ile Lys Asp Lys Tyr Gly Lys Asp Ala Thr Asn Val Gly
                195                 200                 205
Asp Glu Gly Gly Phe Ala Pro Asn Ile Leu Glu Asn Ser Glu Ala Leu
210                 215                 220
Glu Leu Val Lys Glu Ala Ile Asp Lys Ala Gly Tyr Thr Glu Lys Met
225                 230                 235                 240
Val Ile Gly Met Asp Val Ala Ala Ser Glu Phe Tyr Arg Asp Gly Lys
                245                 250                 255
Tyr Asp Leu Asp Phe Lys Ser Pro Ala Asp Pro Ser Arg Cys Ile Thr
                260                 265                 270
Gly Asp Gln Leu Gly Ala Leu Tyr Gln Asp Phe Val Arg Asn Tyr Pro
                275                 280                 285
Val Val Ser Ile Glu Asp Pro Phe Asp Gln Asp Asp Trp Ala Ala Trp
                290                 295                 300
Ser Lys Phe Thr Ala Asn Val Gly Ile Gln Ile Val Gly Asp Asp Leu
305                 310                 315                 320
Thr Val Thr Asn Pro Lys Arg Ile Glu Arg Ala Val Glu Glu Lys Ala
                325                 330                 335
Cys Asn Cys Leu Leu Leu Lys Val Asn Gln Ile Gly Ser Val Thr Glu
                340                 345                 350
Ala Ile Gln Ala Cys Lys Leu Ala Gln Glu Asn Gly Trp Gly Val Met
                355                 360                 365
Val Ser His Arg Ser Gly Glu Thr Glu Asp Thr Phe Ile Ala Asp Leu
                370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Met Arg Ile Glu Glu Glu
                405                 410                 415
Leu Gly Glu Glu Ala Arg Phe Ala Gly His Asn Phe Arg Asn Pro Ser
                420                 425                 430
Val Leu

<210> SEQ ID NO 93
<211> LENGTH: 434
<212> TYPE: PRT
<213> ORGANISM: Bovine
```

<400> SEQUENCE: 93

Met Ser Ile Glu Lys Ile Trp Ala Arg Glu Ile Leu Asp Ser Arg Gly
1               5                   10                  15

Asn Pro Thr Val Glu Val Asp Leu His Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Thr Thr Ile Ala Pro Val Leu Ile Ser Ser
65                  70                  75                  80

Gly Leu Ser Val Val Glu Gln Glu Lys Leu Asp Asn Leu Met Leu Asp
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Arg Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 94
<211> LENGTH: 434
<212> TYPE: PRT
<213> ORGANISM: Pig

<400> SEQUENCE: 94

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Thr Thr Ile Ala Pro Ala Leu Val Ser Ser
65                  70                  75                  80

Gly Leu Ser Val Val Glu Gln Glu Lys Leu Asp Asn Leu Met Leu Asp
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Asp Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Ser Glu
            340                 345                 350

```
Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu
                405                 410                 415

Leu Gly Asp Glu Ala Arg Phe Ala Gly His Asn Phe Arg Asn Pro Ser
                420                 425                 430

Val Leu

<210> SEQ ID NO 95
<211> LENGTH: 434
<212> TYPE: PRT
<213> ORGANISM: Horse

<400> SEQUENCE: 95

Met Ser Ile Glu Lys Ile Trp Ala Arg Glu Ile Leu Asp Ser Arg Gly
1               5                   10                  15

Asn Pro Thr Val Glu Val Asp Leu Cys Thr Ala Lys Gly Leu Phe Arg
                20                  25                  30

Ala Ala Val Pro Ser Gly Ala Ser Thr Gly Ile Tyr Glu Ala Leu Glu
            35                  40                  45

Leu Arg Asp Gly Asp Lys Gln Arg Tyr Leu Gly Lys Gly Val Leu Lys
        50                  55                  60

Ala Val Asp His Ile Asn Thr Thr Ile Ala Pro Ala Leu Ile Ser Ser
65                  70                  75                  80

Gly Phe Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285
```

```
Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
                340                 345                 350

Ala Ile Gln Ala Cys Lys Leu Ala Gln Glu Asn Gly Trp Gly Val Met
                355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu
                405                 410                 415

Leu Gly Asp Glu Ala Arg Phe Ala Gly His Asn Phe Arg Asn Pro Ser
                420                 425                 430

Val Leu

<210> SEQ ID NO 96
<211> LENGTH: 434
<212> TYPE: PRT
<213> ORGANISM: Chicken

<400> SEQUENCE: 96

Met Ala Val Glu Arg Ile His Ala Arg Glu Ile Leu Asp Ser Arg Gly
1               5                   10                  15

Asn Pro Thr Val Glu Val Asp Leu Tyr Thr His Lys Gly Met Phe Arg
                20                  25                  30

Ala Ala Val Pro Ser Gly Ala Ser Thr Gly Ile Tyr Glu Ala Leu Glu
            35                  40                  45

Leu Arg Asp Asn Asp Lys Ser Arg Phe Leu Gly Lys Gly Val Leu Gln
    50                  55                  60

Ala Val Asp His Ile Asn Ser Thr Val Ala Pro Ala Ile Val Gly Ser
65                  70                  75                  80

Gly Leu Ser Val Val Asp Gln Glu Lys Ile Asp Asn Leu Met Leu Glu
                85                  90                  95

Met Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Lys Asp Val
            115                 120                 125

Pro Leu Tyr Arg His Ile Ala Asp Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Ile Gly Ala Glu Val Tyr His Asn Leu
            180                 185                 190

Lys Ser Val Ile Lys Glu Lys Tyr Gly Lys Asp Ala Thr Asn Val Gly
    195                 200                 205

Asp Glu Gly Gly Phe Ala Pro Asn Ile Leu Glu Asn Ser Glu Ala Leu
    210                 215                 220
```

```
Glu Leu Leu Lys Glu Ala Ile Asp Lys Ala Gly Tyr Thr Asp Lys Ile
225                 230                 235                 240

Val Ile Gly Met Asp Val Ala Ala Ser Glu Phe Tyr Arg Asp Gly Lys
            245                 250                 255

Tyr Asp Leu Asp Phe Lys Ser Pro Asp Pro Ser Arg Tyr Ile Ser
        260                 265                 270

Ala Asp Glu Leu Gly Asp Leu Tyr Gln Ser Phe Val Arg Ala Tyr Pro
        275                 280                 285

Val Leu Ser Ile Glu Asp Pro Phe Asp Gln Asp Trp Glu Ala Trp
290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
            325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
370                 375                 380

Val Val Ala Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
            405                 410                 415

Leu Gly Asp Glu Ala Arg Phe Ala Gly His Asn Phe Arg Asn Pro Ser
            420                 425                 430

Val Leu

<210> SEQ ID NO 97
<211> LENGTH: 434
<212> TYPE: PRT
<213> ORGANISM: Felis

<400> SEQUENCE: 97

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Thr Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160
```

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe His Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 98
<211> LENGTH: 434
<212> TYPE: PRT
<213> ORGANISM: Canine

<400> SEQUENCE: 98

Met Ser Ile Glu Lys Ile Trp Ala Arg Glu Ile Leu Asp Ser Arg Gly
1               5                   10                  15

Asn Pro Thr Val Glu Val Asp Leu His Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Thr Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

```
Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Arg Asp Leu
            115                 120                 125

Pro Leu Tyr Arg His Ile Ala Gln Leu Ala Gly Asn Ser Asp Leu Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe His Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 99
<211> LENGTH: 434
<212> TYPE: PRT
<213> ORGANISM: Rabbit

<400> SEQUENCE: 99

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
                20                  25                  30
```

```
Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Gly His Ile Asn Asn Thr Ile Ala Pro Ala Leu Val Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Thr Leu Tyr Gln Asp Phe Val Arg Asp Tyr Pro
        275                 280                 285

Val Val Ser Ile Glu Asp Pro Phe Asp Gln Asp Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu
```

```
<210> SEQ ID NO 100
<211> LENGTH: 434
<212> TYPE: PRT
<213> ORGANISM: Sheep

<400> SEQUENCE: 100

Met Ser Ile Glu Lys Ile Trp Ala Arg Glu Ile Leu Asp Ser Arg Gly
1               5                   10                  15

Asn Pro Thr Val Glu Val Asp Leu His Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
    50                  55                  60

Ala Val Asp His Ile Asn Thr Thr Ile Ala Pro Val Leu Ile Ser Ser
65                  70                  75                  80

Gly Leu Ser Val Val Glu Gln Glu Lys Leu Asp Asn Leu Met Leu Asp
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
    210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Trp Ala Ala Trp
    290                 295                 300

Ser Lys Phe Thr Ala Asn Val Gly Ile Gln Ile Val Gly Asp Asp Leu
305                 310                 315                 320

Thr Val Thr Asn Pro Lys Arg Ile Glu Arg Ala Val Glu Glu Lys Ala
                325                 330                 335

Cys Asn Cys Leu Leu Leu Lys Val Asn Gln Ile Gly Ser Val Thr Glu
            340                 345                 350

Ala Ile Gln Ala Cys Lys Leu Ala Gln Glu Asn Gly Trp Gly Val Met
        355                 360                 365

Val Ser His Arg Ser Gly Glu Thr Glu Asp Thr Phe Ile Ala Asp Leu
    370                 375                 380
```

```
Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Glu Ala Arg Phe Ala Gly His Asn Phe Arg Asn Pro Ser
            420                 425                 430

Val Leu

<210> SEQ ID NO 101
<211> LENGTH: 434
<212> TYPE: PRT
<213> ORGANISM: Artificial Sequence
<220> FEATURE:
<223> OTHER INFORMATION: ENOG Consensus sequence

<400> SEQUENCE: 101

Met Ser Ile Glu Lys Ile Trp Ala Arg Glu Ile Leu Asp Ser Arg Gly
1               5                   10                  15

Asn Pro Thr Val Glu Val Asp Leu Tyr Thr Ala Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Gly Asp Lys Gln Arg Tyr Leu Gly Lys Gly Val Leu Lys
50                  55                  60

Ala Val Asp His Ile Asn Thr Thr Ile Ala Pro Ala Leu Ile Ser Ser
65                  70                  75                  80

Gly Leu Ser Val Val Glu Gln Glu Lys Leu Asp Asn Leu Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Arg Glu Leu
        115                 120                 125

Pro Leu Tyr Arg His Ile Ala Gln Leu Ala Gly Asn Ser Asp Leu Ile
130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Glu
                165                 170                 175

Ser Phe Arg Asp Ala Met Arg Leu Gly Ala Glu Val Tyr His Thr Leu
            180                 185                 190

Lys Gly Val Ile Lys Asp Lys Tyr Gly Lys Asp Ala Thr Asn Val Gly
        195                 200                 205

Asp Glu Gly Gly Phe Ala Pro Asn Ile Leu Glu Asn Ser Glu Ala Leu
210                 215                 220

Glu Leu Val Lys Glu Ala Ile Asp Lys Ala Gly Tyr Thr Glu Lys Ile
225                 230                 235                 240

Val Ile Gly Met Asp Val Ala Ala Ser Glu Phe Tyr Arg Asp Gly Lys
                245                 250                 255

Tyr Asp Leu Asp Phe Lys Ser Pro Ala Asp Pro Ser Arg Tyr Ile Thr
            260                 265                 270

Gly Asp Gln Leu Gly Ala Leu Tyr Gln Asp Phe Val Arg Asp Tyr Pro
        275                 280                 285

Val Val Ser Ile Glu Asp Pro Phe Asp Gln Asp Asp Trp Ala Ala Trp
290                 295                 300

Ser Lys Phe Thr Ala Asn Val Gly Ile Gln Ile Val Gly Asp Asp Leu
```

```
305                 310                 315                 320
Thr Val Thr Asn Pro Lys Arg Ile Glu Arg Ala Val Glu Glu Lys Ala
                325                 330                 335
Cys Asn Cys Leu Leu Leu Lys Val Asn Gln Ile Gly Ser Val Thr Glu
                340                 345                 350
Ala Ile Gln Ala Cys Lys Leu Ala Gln Glu Asn Gly Trp Gly Val Met
                355                 360                 365
Val Ser His Arg Ser Gly Glu Thr Glu Asp Thr Phe Ile Ala Asp Leu
            370                 375                 380
Val Val Gly Leu Cys Thr Gly Gln Ile Lys Thr Gly Ala Pro Cys Arg
385                 390                 395                 400
Ser Glu Arg Leu Ala Lys Tyr Asn Gln Leu Met Arg Ile Glu Glu Glu
                405                 410                 415
Leu Gly Asp Glu Ala Arg Phe Ala Gly His Asn Phe Arg Asn Pro Ser
                420                 425                 430
Val Leu
```

ANTI-TUMOUR IMMUNE RESPONSES TO MODIFIED SELF-EPITOPES

The present invention relates generally to modified peptides that can be used as targets for cancer immunotherapy. The modified peptides may be citrullinated enolase peptides. These modified peptides can be used as vaccines or as targets for monoclonal antibody (mAb) therapy. Such vaccines or mAbs may be used in the treatment of cancer.

In order to be effective, cancer vaccines need to induce a potent immune response which is able to break the tolerance and overcome the immunosuppressive tumour environment. The importance of CD4 T cells in mediating tumour destruction has been recently highlighted however the induction of self-specific CD4 responses has proved more difficult. In contrast, CD4 T cells recognizing modified self-epitopes have been shown to play a role in the pathophysiology of several autoimmune diseases such as rheumatoid arthritis (RA), collagen II-induced arthritis, sarcoidosis, celiac disease and psoriasis (Choy, 2012, Grunewald and Eklund, 2007, Coimbra et al., 2012, Holmdahl et al., 1985). One of these common modifications is citrullination of arginine which involves the conversion of the positively charge aldimine group (=NH) of arginine to the neutrally charged ketone group (=O) of citrulline. Citrullination is mediated by Peptidylarginine deiminases (PADs), which are a family of calcium dependent enzymes found in a variety of tissues. A recent report by Ireland et al. 2011, demonstrates that the presentation of citrullinated T cell epitopes on APCs is also dependent upon autophagy and PAD activity. This process has also been demonstrated to be an efficient mechanism to enable processing of endogenous antigens for presentation on MHC class II molecules in professional APCs as well as epithelial cells (Munz, 2012, Schmid et al., 2007). Autophagy is constitutive in APCs but is only induced by stress in other cells (Green and Levine, 2014). Thus T cells recognizing citrullinated epitopes have no target on normal healthy cells. Autophagy is triggered by stress such as hypoxia and nutrient starvation and is upregulated to promote tumour survival (Green and Levine, 2014).

One protein which is citrullinated is enolase, which is a glycolytic enzyme found in the cytoplasm. It is also expressed on the cell surface where it acts as a plasminogen receptor (Miles et al., 1991). In mammals there are four isoforms of the enolase enzyme which are encoded by four distinct genes (Diaz-Ramos et al., 2012). The ENO1 gene encodes the alpha-enolase which is expressed in almost all adult tissue. ENO2 (beta-enolase) is expressed in muscle tissue and ENO3 (gamma-enolase) is found in neurons (Marangos et al., 1978). More recently a fourth variant ENO4 has been identified which is expressed exclusively in sperm (Nakamura et al., 2013). Enzymatically active enolase is formed of two subunits which can be homo- or heterodimeric (Pancholi, 2001).

ENO1 and ENO3 were identified as citrullinated proteins in the CNS (Jang et al., 2008, Jang et al., 2010) and as autoantigen in rheumatoid arthritis (Kinloch et al., 2005, Kinloch et al., 2008, Lundberg et al., 2008, Mandi et al., 2009). More recently monoclonal antibodies recognising citrullination of Arg9 in ENO1, Citrullination of Arg9 in ENO1 and ENO3 and citrullination of Arg9 in ENO3 have been described (Jang et al., 2012) and have shown that citrullinated enolase lost its enzymatic activity and was more rapidly degraded by calpain-1 but citrullination increased ENO1 and ENO3 plasminogen binding activity. A number of citrullinated enolase peptides have been described which bind to human MHC II (WO2012138294 A1) and can activate T cells in patients with rheumatoid arthritis to produce IL-17.

The role of enolase in anaerobic glycolysis and in localisation of plasminogen on the cell surface have highlighted it as a possible target for anti-tumour therapies. Firstly, hypoxia in the tumour microenvironment is a major factor during growth of solid tumour. Therefore, upregulation of glycolytic enzymes is necessary for tumour survival. The ENO1 promoter contains a hypoxia responsive element which is unregulated in cells in response to hypoxic stress (Semenza et al., 1996). Secondly, cell surface enolase acts as a plasminogen binding molecule allowing the cleavage of plasminogen to plasmin by plasminogen activator. This process is important for cell invasion with elevated levels of plasminogen activator linked to malignancy (Andreasen et al., 2000). Together these functions mean that enolase plays an active role in tumour growth and metastasis. Multiple approaches have been developed for targeting enolase therapeutically. ENO1 silencing reduced endometrial cell glycolysis, proliferation and migration in vitro and significantly inhibited cell growth in vivo (Zhou et al., 2010). Similarly, administration of anti-ENO1 mAb has been shown to reduce the in vivo growth and metastasis of the human pancreatic cell line CFPAC-1 (Principe et al., 2015). ENO1 has been shown to be overexpressed in a number of cancer tissues including endometrial carcinoma, pancreatic ductal adenocarcinoma and non-small cell lung cancer (Zhao et al., 2015, Cappello et al., 2009, Fu et al., 2015). In addition, high enolase expression has been correlated with poor clinical outcome for a number of tumours including breast, hepatocellular and gastric (Reviewed by Capello et al., 2011). In lung cancer, up-regulation of ENO1 expression in tumour cells was observed in 11 out of 17 patients. Higher ENO1 expression was correlated with disease recurrence and advanced tumour stage (Chang et al., 2006).

In many patients including pancreatic, leukaemia, melanoma, head and neck, breast and lung ENO1 has been shown to be an autoantigen (Capello et al., 2011). In pancreatic cancer ENO1 elicits a CD4 and a CD8 T cell response both in vitro and in vivo (Cappello et al., 2009) which inhibited the growth of pancreatic ductal adenocarcinoma cells but no specific T epitopes were identified. In Head and Neck cancer an HLA-DR8 restricted peptide (aa 321-336) stimulated cytotoxic CD4 T cells responses (Kondo et al., 2002). In a genetic model of pancreatic adenocarcinoma vaccination with ENO1 DNA elicited humoral and cellular immune responses against tumours delays tumour progression and significantly extended survival (Cappello et al., 2013). The use of wild type Enolase antigen as a diagnostic and therapeutic agent in cancer has been described (U.S. Pat. No. 7,645,453 B2). In addition, agents targeting alpha-enolase have been described as a way of increasing the sensitivity of neoplastic cells to chemotherapeutic agents (WO 2007072219 A2). We have previously shown that citrullinated Vimentin peptides can induce CD4-mediated immune responses which result in tumour rejection and long-term survival (WO2014023957 A2). However, all of the immune responses measured against enolase recognised wild type or phosphorylated enolase but not citrullinated enolase suggesting that this enzyme was not citrullinated in cancer.

The inventors have shown that, in normal donors and HLA transgenic mice, there is a repertoire of T cells which recognise citrullinated enolase peptides and produce IFNγ. They have also shown that certain citrullinated enolase peptides generate a T cell response in vivo and, as such, can be used as a vaccine target for cancer therapy.

According to a first aspect of the invention, there is provided a peptide comprising, consisting essentially of or consisting of:
an amino acid sequence selected from:

```
(Eno1 241-259)                           (SEQ ID NO: 1)
VIGMDVAASEFFcitSGKYDLD, (Eno2/3 241-259)                         (SEQ ID NO: 2)
VIGMDVAASEFYcitSGKYDLD, (Eno1 21-40)                             (SEQ ID NO: 3)
EVDLFTSKGLFcitAAVPSGAS, (Eno3 21-40)                             (SEQ ID NO: 4)
EVDLYTAKGLFcitAAVPSGAS, (Eno1 126-145)                           (SEQ ID NO: 5)
KGVPLYcitHIADLAGNSEVIL, (mouse Eno1 126-145)                     (SEQ ID NO: 6)
KGVPLYcitHIADLAGNPEVIL, (Eno1 316-335)                           (SEQ ID NO: 7)
VGDDLTVTNPKcitIAKAVNEK
or (mouse Eno1 316-335)                     (SEQ ID NO: 8)
VGDDLTVTNPKcitIAKAASEK (Eno1 11-25)                             (SEQ ID NO: 9)
IFDScitGNPTVEVDLF (Eno3/mouse Eno1 11-25)                  (SEQ ID NO: 10)
IFDScitGNPTVEVDLY
``` wherein "cit" represents citrulline, or
iii) the amino acid sequence of i), with the exception of 1, 2 or 3 amino acid substitutions, and/or 1, 2 or 3 amino acid insertions, and/or 1, 2 or 3 amino acid deletions in a non-citrulline position.

The inventors have unexpectedly found that these citrullinated peptides derived from enolase can be used to raise an immune response against tumours including, but not restricted to, pancreatic, leukaemia, melanoma, head and neck, breast and lung tumours. The inventors have shown that only two peptides
VIGMDVAASEFFcitSGKYDLD (SEQ ID NO: 1)/VIGMDVAASEFYcitSGKYDLD (SEQ ID NO: 2)-enolase 241-260 citrullinated at position 253 and EVDLFTSKGLFcitAAVPSGAS (SEQ ID NO: 3)/EVDLYTAKGLFcitAAVPSGAS (SEQ ID NO: 4)-enolase 21-40 citrullinated at position 32
generated a T cell response in vivo to a citrullinated self enolase epitope. Three peptides
KGVPLYcitHIADLAGNSEVIL (SEQ ID NO: 5)/KGVPLYcitHIADLAGNPEVIL (SEQ ID NO: 6)-enolase 126-145 citrullinated at position 132, VGDDLTVTNPKcitIAKAVNEK (SEQ ID NO: 7)/VGDDLTVTNPKcitIAKAASEK (SEQ ID NO: 8)-enolase 316-335 citrullinated at position 328 and IFDScitGNPTVEVDLF (SEQ ID NO: 9)/IFDScitGNPTVEVDLY (SEQ ID NO: 10)-enolase 11-25 citrullinated at position 15 generated a T cell response in vivo to citrullinated human epitopes which were not homologous to mouse and therefore were recognised as foreign antigens.

Citrullinated peptides are known to stimulate T cell responses in autoimmune patients with the shared HLA DR4DR4 motif. In contrast, the inventors are the first to show that enolase 241-260 citrullinated at position 253 can stimulate potent T cell responses in HLA-DP4 transgenic mice. As HLA-DP4 is expressed by 70% of the population, this makes it a promising vaccine for the treatment of solid tumours. All normal donors showing responses to enolase 241-260 citrullinated at position 253 expressed HLA-DP4. The response to enolase 241-260 citrullinated at position 253 was the strongest and showed minimal reactivity to the unmodified sequence. T cells specific for this citrullinated peptide epitope can target tumour cells to elicit strong anti-tumour effects in vivo, thus providing the first evidence for the use of citrullinated enolase 241-260 as a vaccine target for cancer therapy.

ENO1, ENO2 and ENO3 are highly conserved and all express one or the other of the two enolase 241-260 citrullinated at position 253 peptides. In contrast ENO4 has a large inversion at this point in the gene sequence. Accordingly, enolase 241-260 citrullinated at position 253, as well as nucleic acids encoding it, can be used for targeting ENO1, ENO2 or ENO3.

Previous studies had shown that enolase 241-260 citrullinated at position 253 can stimulate T cells responses in RA patients (WO2012138294). As described in detail in the Examples herein, to test whether the enolase epitopes within a DNA construct were stimulating immune responses against citrullinated enolase, mice were immunised with DNA encoding the enolase epitopes and screened for responses against the unmodified and citrullinated epitopes. The mice immunised with DNA encoding the whole enolase sequence responded only to enolase 241-260 citrullinated at position 253. This suggests that, when the DNA is translated, the enolase 241-260 peptide is preferentially citrullinated, the citrullinated peptide binds with higher affinity to MHC or that the T cells stimulated with unmodified enolase epitope recognise the citrullinated peptides more avidly.

In addition to showing that that encoding epitope within DNA gave a citrullinated T cell responses, enolase 241-260 citrullinated at position 253 peptide alone stimulated a Th1 responses which only recognised modified epitopes and there was no cross reaction against wild type peptide. When normal donors were stimulated with enolase 241-260 citrullinated at position 253 peptide, 4/6 donors showed a response to Enolase 241-260 citrullinated at position 253 but not wild type peptides. This response was shown to be CD4 Th1 response. In marked contrast to the RA patients, no IL-17 was produced.

Enolase 241-260 citrullinated at position 253 peptide was immunised with a variety of adjuvants. Immunostimulatory adjuvants such as CpG/MPLA, Poly I:C and Immiquimod stimulated Th1 responses and were required, as there was no response in the absence of adjuvant. Inert adjuvants such as Incomplete Freund's adjuvant caused induction of predominantly IL-10 responses, suggesting the induction of an iTreg response.

Inserted amino acids and replacement amino acids may be naturally occurring amino acids or may be non-naturally occurring amino acids and, for example, may contain a non-natural side chain. If more than one amino acid residue is substituted and/or inserted, the replacement/inserted amino acid residues may be the same as each other or different from one another. Each replacement amino acid may have a different side chain to the amino acid being replaced.

Enolase is highly conserved between those species in which the gene has been cloned (chicken, mouse, dog, sheep, cow, horse, pig and human). Accordingly, a peptide of the invention, optionally in combination with a nucleic acid comprising a sequence that encodes such a peptide it, can be used for treating cancer in non-human mammals.

The invention also includes within its scope peptides having the amino acid sequence as set out above and sequences having substantial identity thereto, for example, 70%, 80%, 85%, 90%, 95% or 99% identity thereto, as well as their use in medicine and in particular in a method for treating cancer. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul modified as in (Karlin and Altschul, 1993).(Karlin and Altschul, 1993). The NBLAST and XBLAST programs of Altschul, et al. have incorporated such an algorithm (Altschul et al., 1990). BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in (Altschul et al., 1997). Alternatively, PSI-Blast can be used to perform an iterated search that detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller (Myers and Miller, 1989). The ALIGN program (version 2.0) which is part of the GCG sequence alignment software package has incorporated such an algorithm. Other algorithms for sequence analysis known in the art include ADVANCE and ADAM as described in (Torelli and Robotti, 1994) and FASTA described in (Pearson and Lipman, 1988). Within FASTA, ktup is a control option that sets the sensitivity and speed of the search.

Peptides of the invention may be synthesised using Fmoc chemistry or other standard techniques known to those skilled in the art.

Another convenient way of producing a peptide according to the present invention is to express the nucleic acid encoding it, by use of nucleic acid in an expression system.

The inventors have shown that that immunisation with nucleic acids encoding the peptides of the invention gives immune responses to citrullinated peptides but not to wild type non-citrullinated peptides. Accordingly, the present invention further provides an isolated nucleic acid encoding a peptide of the present invention. In a preferred aspect, the present invention provides a nucleic acid which codes for a peptide of the invention as defined above.

The inventors have also found that administration of nucleic acid, such as DNA or RNA, encoding full length enolase gives rise to strong immune responses to only enolase 241-260 citrullinated at position 253. This forms a further aspect of the invention. Examples of the amino acid sequence of full length enolase are provided in the Examples and drawings herein and it is within the skill of a person skilled in the art to provide nucleic acid sequences that encode such amino acid sequences.

The skilled person will be able to determine substitutions, deletions and/or additions to such nucleic acids which will still provide a peptide of the present invention. The nucleic acid may be DNA, cDNA, or RNA such as mRNA obtained by cloning or produced by chemical synthesis. For therapeutic use, the nucleic acid is preferably in a form capable of being expressed in the subject to be treated. The peptide of the present invention or the nucleic acid of the present invention may be provided as an isolate, in isolated and/or purified form, or free or substantially free of material with which it is naturally associated. In the case of a nucleic acid, it may be free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a peptide of the present invention can be readily prepared by the skilled person, for example using the information and references contained herein and techniques known in the art (for example, see (Sambrook, 1989, Ausubel, 1992)), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding the polypeptide may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially-available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a peptide of the invention forms an aspect of the present invention, as does a method of production of the composition which method comprises expression from encoding nucleic acid. Expression may conveniently be achieved by culturing under appropriate conditions recombinant host cells containing the nucleic acid. Following production by expression, a composition may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. Expression in eukaryotic cells in culture is also available to those skilled in the art as an option for production of a specific binding member, see for recent review, for example (Reff, 1993, Trill et al., 1995). For a review, see for example (Pluckthun, 1991). Expression in eukaryotic cells in culture is also available to those skilled in the art as an option for production of a specific binding member, see for recent review, for example (Reff, 1993, Trill et al., 1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: A Laboratory Manual (Sambrook, 1989). Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology (Ausubel, 1992).

Thus, a further aspect of the present invention provides a host cell, which may be isolated, containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a polypeptide as described above.

Polypeptides of the invention can be used to identify and/or isolate binding moieties that bind specifically to the polypeptide of the invention. Such binding moieties may be used as immunotherapeutic reagents and may include antibodies. Therefore, in a further aspect, the invention provides a binding moiety that binds the polypeptide of the invention.

The binding moiety of the invention may be an antibody. The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term "antibody" includes antibody fragments, derivatives, functional equivalents and homologues of antibodies, humanised antibodies, including any polypeptide comprising an immunoglobulin binding domain, whether natural or wholly or partially synthetic and any polypeptide or protein having a binding domain which is, or is homologous to, an antibody binding domain. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to herein as "mab".

It is possible to take an antibody, for example a monoclonal antibody, and use recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin (see, for instance, EP-A-184187, GB 2188638A or EP-A-239400). A hybridoma (or other cell that produces antibodies) may be subject to genetic mutation or other changes, which may or may not alter the binding specificity of antibodies produced.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., *Nature* 341:544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., *Science* 242:423-426 (1988); Huston et al., *PNAS USA* 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., *Proc. Natl. Acad. Sci. USA* 90: 6444-6448 (1993)). Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). Where bispecific antibodies are to be used, these may be conventional bispecific antibodies, which can be manufactured in a variety of ways (Hollinger & Winter, *Current Opinion Biotechnol.* 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., *EMBO Journal* 10:3655-3659 (1991). Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

Also encompassed within the present invention are binding moieties based on engineered protein scaffolds. Protein scaffolds are derived from stable, soluble, natural protein structures which have been modified to provide a binding site for a target molecule of interest. Examples of engineered protein scaffolds include, but are not limited to, affibodies, which are based on the Z-domain of staphylococcal protein A that provides a binding interface on two of its a-helices (Nygren, P. A. (2008). FEBS J 275(11): 2668-76); anticalins, derived from lipocalins, that incorporate binding sites for small ligands at the open end of a beta-barrel fold (Skerra, A. (2008) FEBS J 275(11): 2677-83), nanobodies, and DARPins. Engineered protein scaffolds are typically targeted to bind the same antigenic proteins as antibodies, and are potential therapeutic agents. They may act as inhibitors or antagonists, or as delivery vehicles to target molecules, such as toxins, to a specific tissue in vivo (Gebauer, M. and A. Skerra (2009). Curr Opin Chem Biol 13(3): 245-55). Short peptides may also be used to bind a target protein. Phylomers are natural structured peptides derived from bacterial genomes. Such peptides represent a diverse array of protein structural folds and can be used to inhibit/disrupt protein-protein interactions in vivo (Watt, P. M. (2006). Nat Biotechnol 24(2): 177-83)].

In a further aspect, the present invention provides a peptide of the first aspect and/or a nucleic acid comprising a sequence that encodes such a peptide and/or a binding moiety of the invention, for use in medicine.

The invention also provides a peptide of the first aspect and/or a nucleic acid comprising a sequence that encodes such a peptide and/or a binding moiety of the invention, for use in a method for treating cancer, as well as the use of such a peptide and/or nucleic acid and/or binding moiety, in the manufacture of a medicament for the treatment of cancer. The invention also provides a method of treating cancer, comprising administering a peptide of the first aspect and/or a nucleic acid comprising a sequence that encodes such a peptide and/or binding moiety of the invention to a subject in need of such treatment. The cancer may be breast cancer including oestrogen receptor negative breast cancer, colorectal cancer, gastric cancer, non-small cell lung cancer, ovarian cancer including endometrial carcinoma, pancreatic cancer including pancreatic ductal adenocarcinoma, leukaemia, melanoma, head and neck cancer or lung cancer.

The peptide may be a T or B cell epitope. Peptides in accordance with the present invention may be used alone or in combination. In addition, they may be used in combination with other therapeutic agents, such as anti-cancer agents including but not limited to checkpoint blockade drugs such as ipilimumab.

Peptides in accordance with the invention may be delivered in vivo as a peptide, optionally in the form of a peptide as disclosed in WO02/058728. The inventors have surprisingly found that peptides of the invention give rise to strong immune responses when administered as a peptide. Such peptides may be administered as just the sequence of the peptide, or as a polypeptide containing the peptide, or even as the full length protein. Alternatively, peptide in accordance with the invention may be administered in vivo as a nucleic acid encoding the peptide, encoding a polypeptide containing the peptide or even encoding the full length protein. Such nucleic acids may be in the form of a mini gene, i.e. encoding a leader sequence and the peptide or a leader sequence and full length protein. Nucleic acids encoding epitopes useful in the present invention may be targeted to antigen presenting cells and other cells that express PAD enzymes, preferably PAD4 enzymes. Nucleic acids of the present invention may be targeted by including a nucleic acid encoding a targeting agent, such as Fc or a monoclonal antibody targeting a different antigen on APCs, e.g. anti-DEC205 mAb or by means of intradermal injection as skin has a large number of APCs.

As used herein, the term "treatment" includes any regime that can benefit a human or non-human animal. The polypeptide and/or nucleic acid and/or binding moiety may be employed in combination with a pharmaceutically acceptable carrier or carriers to form a pharmaceutical composition. Such carriers may include, but are not limited to, saline, buffered saline, dextrose, liposomes, water, glycerol, ethanol and combinations thereof.

It is envisaged that injections will be the primary route for therapeutic administration of the compositions of the invention although delivery through a catheter or other surgical tubing may also be used. Some suitable routes of administration include intravenous, subcutaneous, intradermal, intraperitoneal and intramuscular administration. Liquid formulations may be utilised after reconstitution from powder formulations.

For intravenous injection, or injection at the site of affliction, the active ingredient will be in the form of a parentally acceptable aqueous solution which is pyrogen-free, has suitable pH, is isotonic and maintains stability. Those of relevant skill in the art are well able to prepare suitable solutions using, for example, isotonic vehicles such as sodium chloride injection, Ringer's Injection or Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of cancer, and in the prevention of the recurrence of such conditions after initial treatment or surgery. Examples of the techniques and protocols mentioned above can be found in Remington's Pharmaceutical Sciences (Remington, 1980). A composition may be administered alone or in combination with other treatments, either simultaneously or sequentially dependent upon the condition to be treated. Other cancer treatments include other monoclonal antibodies, other chemotherapeutic agents, other radiotherapy techniques or other immunotherapy known in the art. One particular application of the compositions of the invention is as an adjunct to surgery, i.e. to help to reduce the risk of cancer reoccurring after a tumour is removed. The compositions of the present invention may be generated wholly or partly by chemical synthesis. The composition can be readily prepared according to well-established, standard liquid or, preferably, solid-phase peptide synthesis methods, general descriptions of which are broadly available (see, for example, in Solid Phase Peptide Synthesis, $2^{nd}$ edition (Stewart, 1984), in The Practice of Peptide Synthesis (Bodanzsky, 1984) and Applied Biosystems 430A User's Manual, ABI Inc., or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

The polypeptides, complexes, nucleic acid molecules, vectors, cells and binding moieties of the invention may be non-naturally occurring and/or purified and/or engineered and/or recombinant and/or isolated and/or synthetic.

It is preferred of the peptide of the invention does not comprise, consist essentially of or consist of a sequence selected from:

VAASEFFRSGKYDLDFKSPD (SEQ ID NO: 11)

VAASEFYRSGKYDLDFKSPD (SEQ ID NO: 12)

TSKGLFcitAAVPSGASTGIYE (SEQ ID NO: 13)

TAKGLcitAAVPSGASTGIYE (SEQ ID NO: 14)

AGAVEKGVPLYcitHIADLAGN (SEQ ID NO: 15)

TVTNPKcitIAKAVNEKSCNCL (SEQ ID NO: 16)

or

TVTNPKcitIAKAASEKSCNCL. (SEQ ID NO: 17)

Preferred features of each aspect of the invention are as for each of the other aspects mutatis mutandis. The prior art documents mentioned herein are incorporated to the fullest extent permitted by law.

EXAMPLES

The present invention will now be described further with reference to the following examples and the accompanying drawings.

Figure 1:
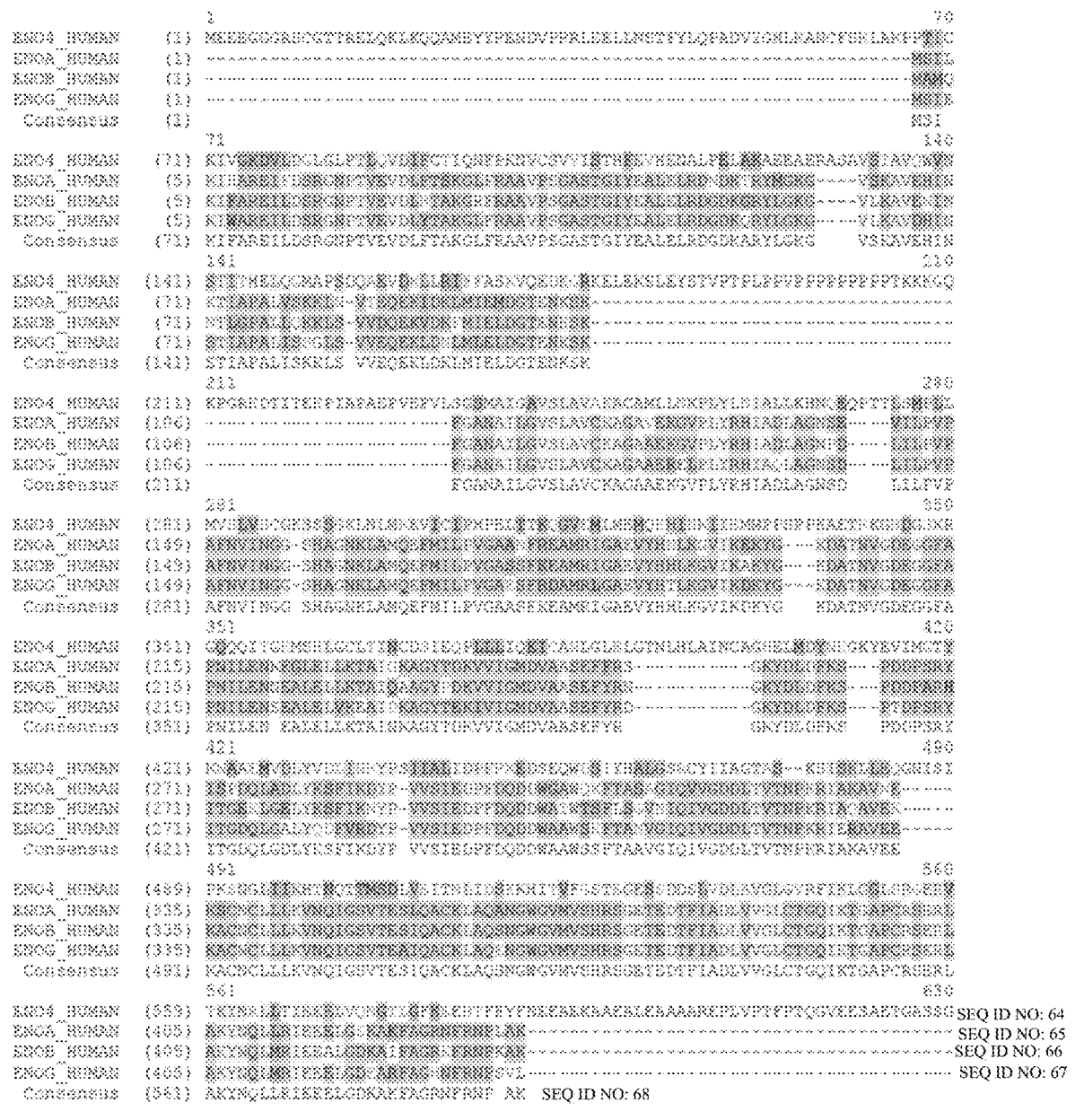

FIG. 1: Sequence alignments of Human Enolase.

Alignment of Human Enolase Subunits ENOA (ENO1, α), ENOB (ENO3, β), ENOG (ENO2, γ) and ENO4 depicting homology. Light grey homologous regions, dark grey not homologous with ENO4.

FIG. 2. Screening IFNγ responses to peptide pools

Transgenic mouse strains with human DR4 (A) or DR1/HHD (B) and parental C57BL/6 (C) mice were used to screen IFNγ responses to peptide. Mice were immunised with pools of 4-6 non-overlapping Human citrullinated Enolase peptides. 14 days after immunisation, mice were sacrificed and splenocytes were harvests. Ex vivo responses to stimulation with Human and mouse equivalent peptides were assessed by IFNγ Elispot. Media only responses were used as a negative control. For each pool n=3. Statistical significance of peptide responses compared to media responses for each pool was determined by ANOVA with Dunnett's post-hoc test * $p<0.5$,  $p<0.01$, * $p<0.001$.

Figure 3:
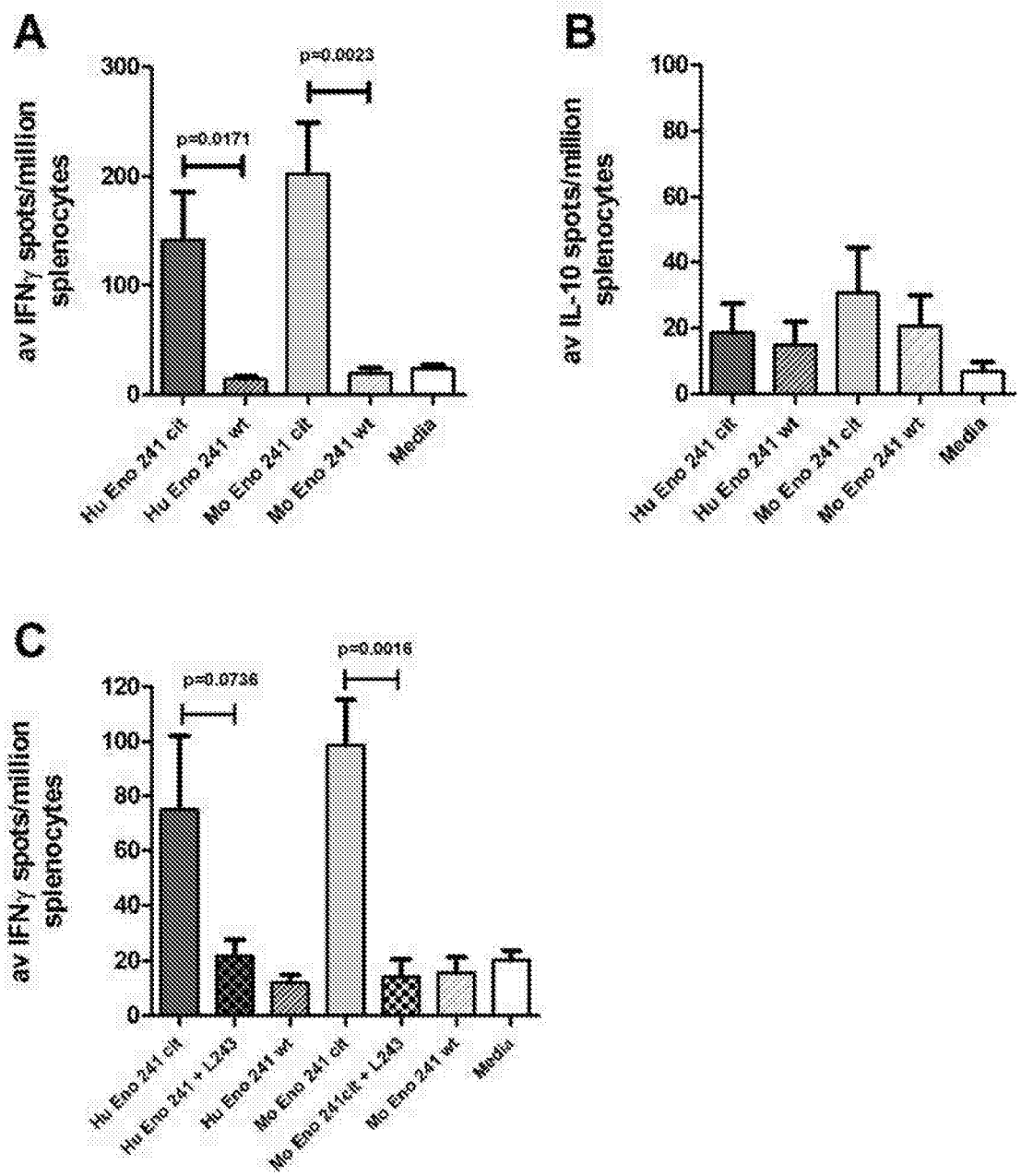

FIG. 3. Human Enolase 241-260 citrullinated peptide induces strong IFNγ responses A single immunisation of human 241cit peptide was given to transgenic DR4 mice. Ex vivo Elispot was used to determine the IFNγ (A) and IL-10 (B) responses generated to the human and mouse equivalent citrullinated (cit) peptides and the wild type (wt) sequences. IFNγ responses to citrullinated peptides in the presence of MHC class II blocking antibody (L243) were also assessed by Elispot (C). For all assays media only responses were used as a negative control. For each experiment n=3. p values are shown.

Figure 4:
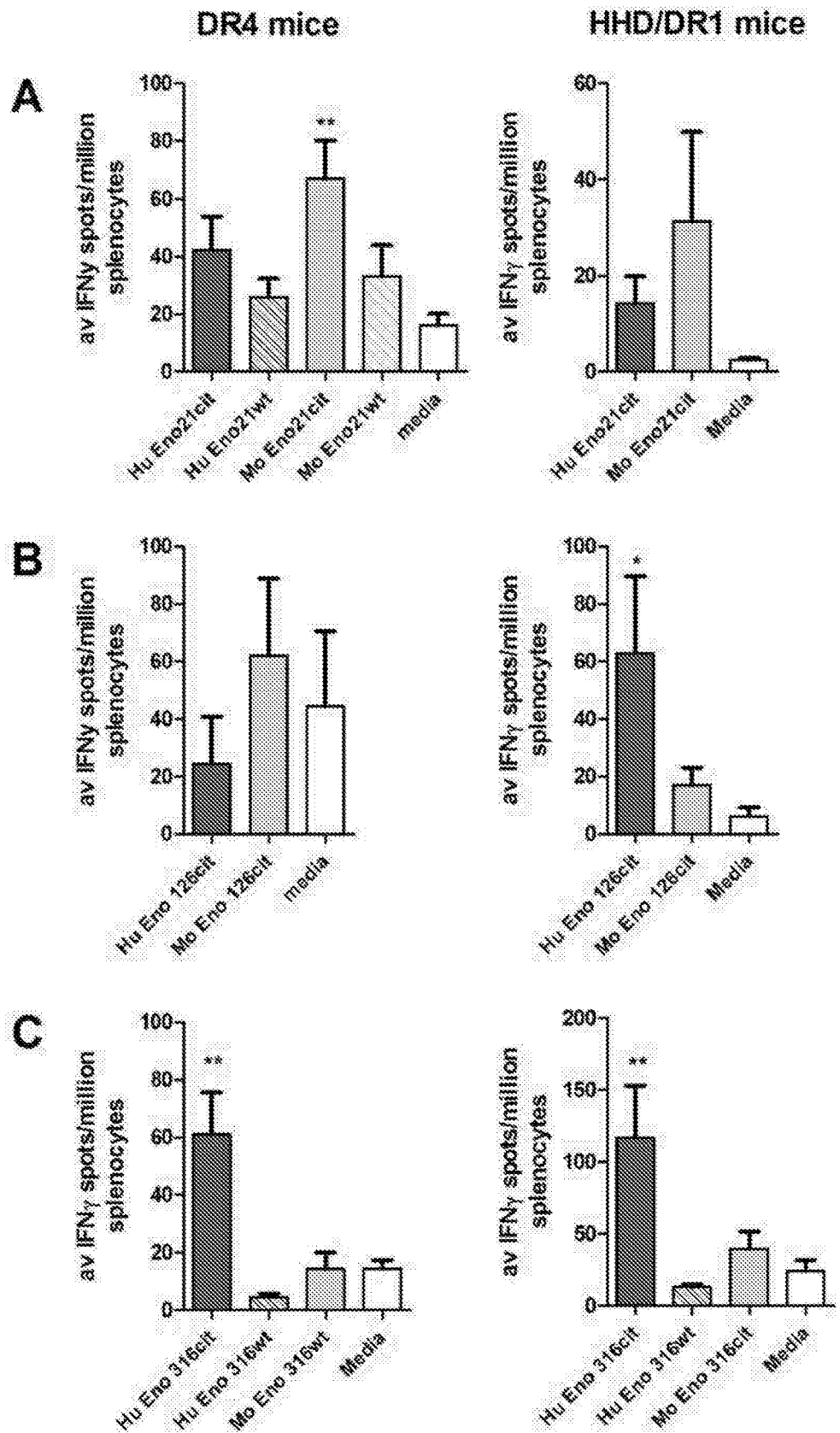

FIG. 4. Multiple citrullinated Enolase peptides induce low level IFNγ responses Mice were given a single immunisation of citrullinated human Enolase peptides corresponding to positions 21-40 (A), 126-145 (B) and 316-335 (C). Ex vivo Elispot was used to determine IFNγ responses in DR4 and DR1/HHD mice. Responses are shown to human and mouse citrullinated peptides and their wild type equivalents when available. Media only responses were used as a negative control. For each peptide n=3. Statistical significance of responses compared to media control were determined by ANOVA with Dunnett's post-hoc test * $p<0.5$,  $p<0.01$, * $p<0.001$.

Figure 5:
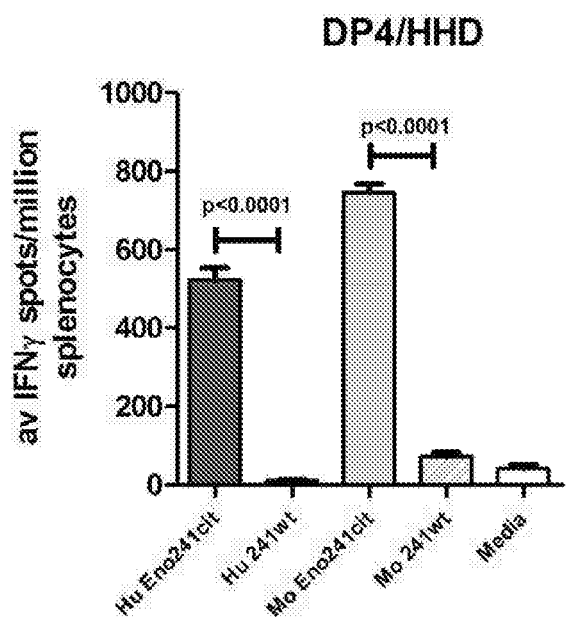

FIG. 5. Enolase 241cit peptide induces responses in DP4 mice.

Transgenic DP4 mice were immunised with three doses of Enolase 241cit peptide over three weeks. Splenocytes were collected 21 days after the initial dose was administered. Ex vivo IFNγ Elispot were used to determine the response to Enolase 241 peptides.

Figure 6:
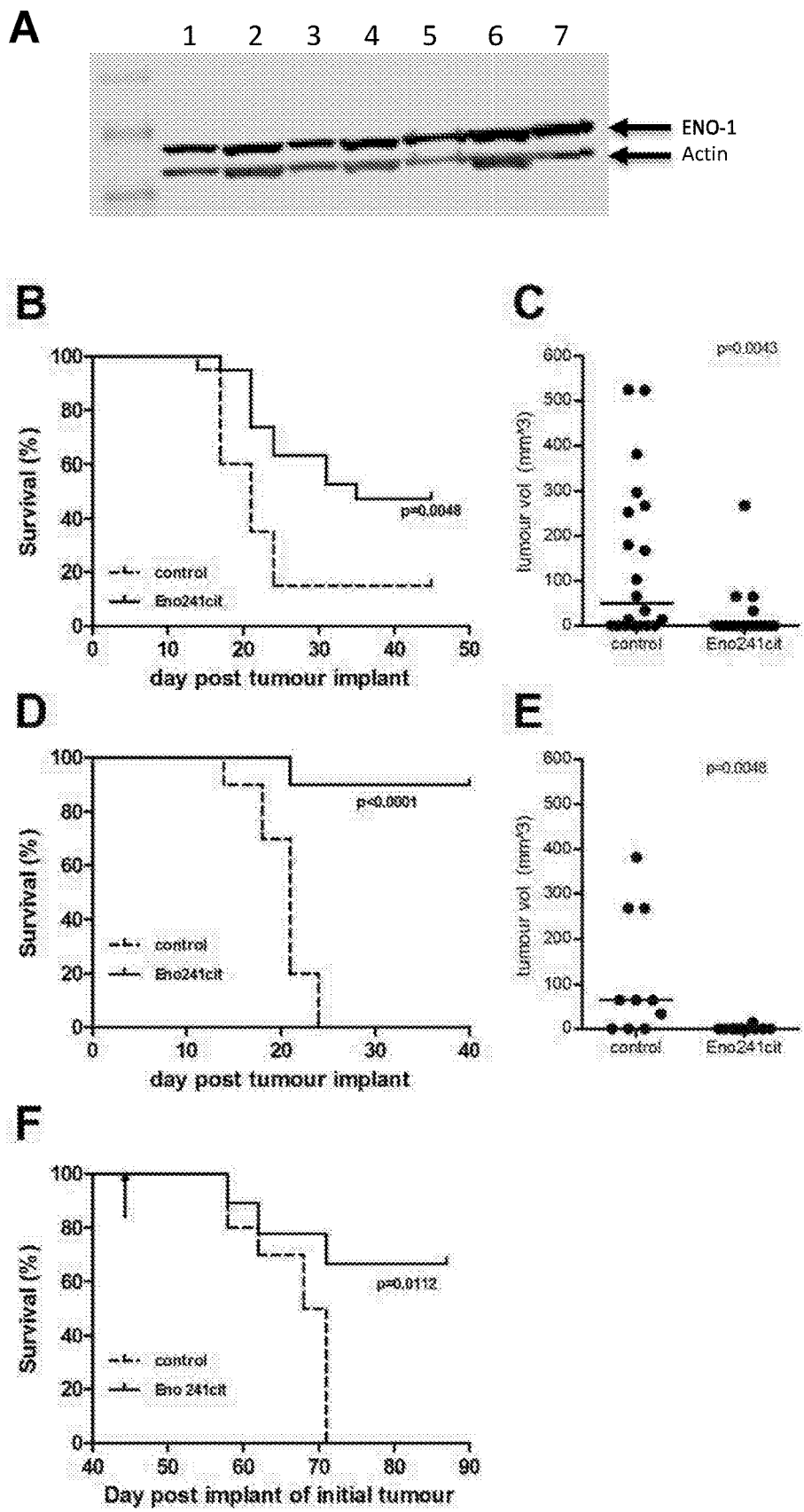

FIG. 6. Human Enolase 241cit peptide provides an in vivo survival advantage in anti-tumour studies Immunoblot (A) of lysates from B16F1 (Lane 1), ID8 (Lane 2), TrampC1 (Lane 3), Pan02 (Lane 4), LLC/2 (Lane 5), RTLCL (Lane 6), HeLa (Lane 7) cell lines against ladder probed for a Enolase (ENO1) and β actin. The bands correspond to the expected size for ENO-1 (47 kDa) and β-actin (42 kDa).

DR4 mice were challenged with B16DR4 tumour. Survival (B) and tumour size at day 17 post tumour implant (C) are shown for unimmunised control animals and animals immunised with Enolase 241cit peptide four days after tumour implant. n=10, results shown are from two independent experiments.

DR4 mice were challenged with B16 tumour expressing IFNγ inducible DR4. Survival (D) and tumour size at day 17 post tumour implant (E) are shown for unimmunised control animals and animals immunised with Enolase 241cit peptide four days after tumour implant. n=10. Surviving mice from the immunised group were rechallenged with the same tumour cell line at day 42 post initial tumour implant (indicated by arrow). Survival data for rechallenged mice and a previous unchallenged control group are shown (F). Significant p values are shown. For tumour volume medians and p values are shown as determined by Mann Whitney U test.

Figure 7:
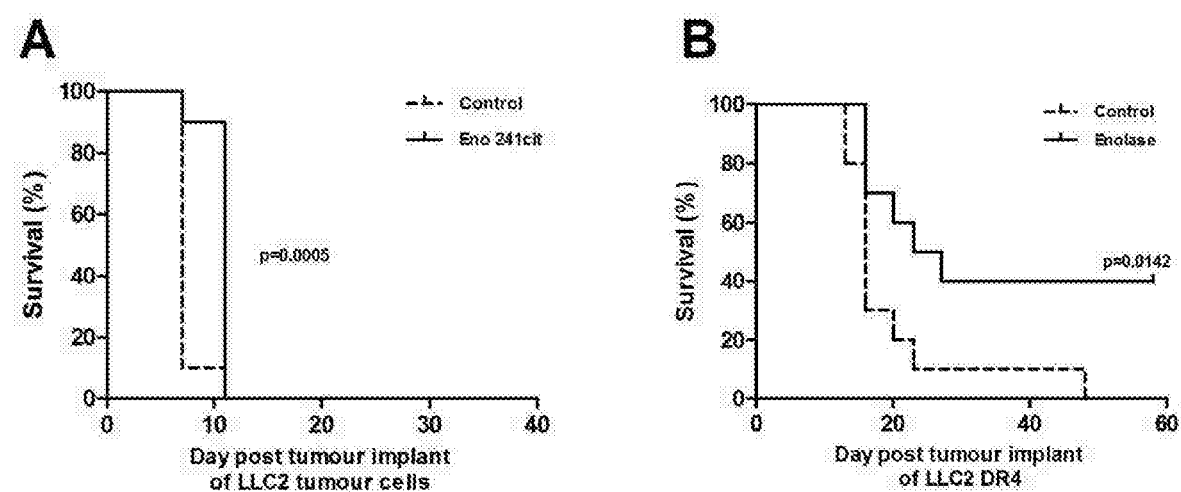

FIG. 7. Enolase 241cit peptide provides a survival advantage in an LLC2 tumour model DR4 mice were challenged with the Lewis lung carcinoma cell line LLC2. Four days after tumour challenge mice were immunised with human Enolase 241cit peptide. Survival data for mice challenged with wild type LLC2 (A) or LLC2 transfected with constitutive chimeric DR4 (B) are shown. Statistical differences between immunised and unimmunised control mice were determined by Mantel-Cox test, p values are shown, n=10.

Figure 8:
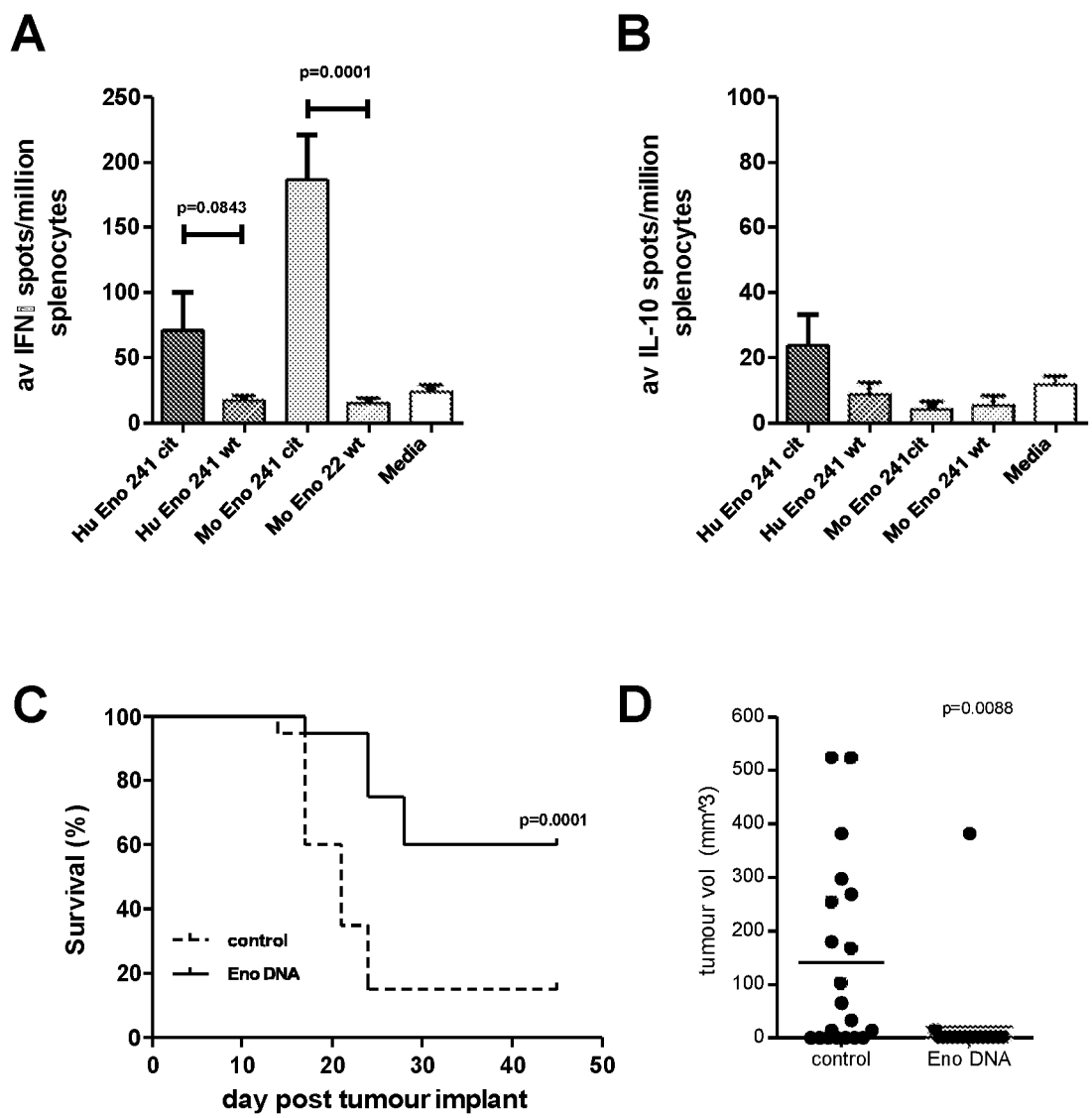

FIG. 8. ENO1 DNA vaccination induces a similar response to Enolase241cit peptide DR4 mice were given two immunisations of ENO1 DNA bullets using a gene gun. After 14 days after the second immunisation mice were sacrificed and splenocytes were harvested. Ex vivo Elispots were performed to determine IFNγ (A) and IL-10 (B) responses to stimulation with Enolase 241peptides. Mice were challenged with B16DR4 tumour cell line which constitutively expressed DR4 and after 4 days were immunised with ENO1 DNA, survival data (C) and tumour volume at day 11 (D) are shown.

Figure 9:
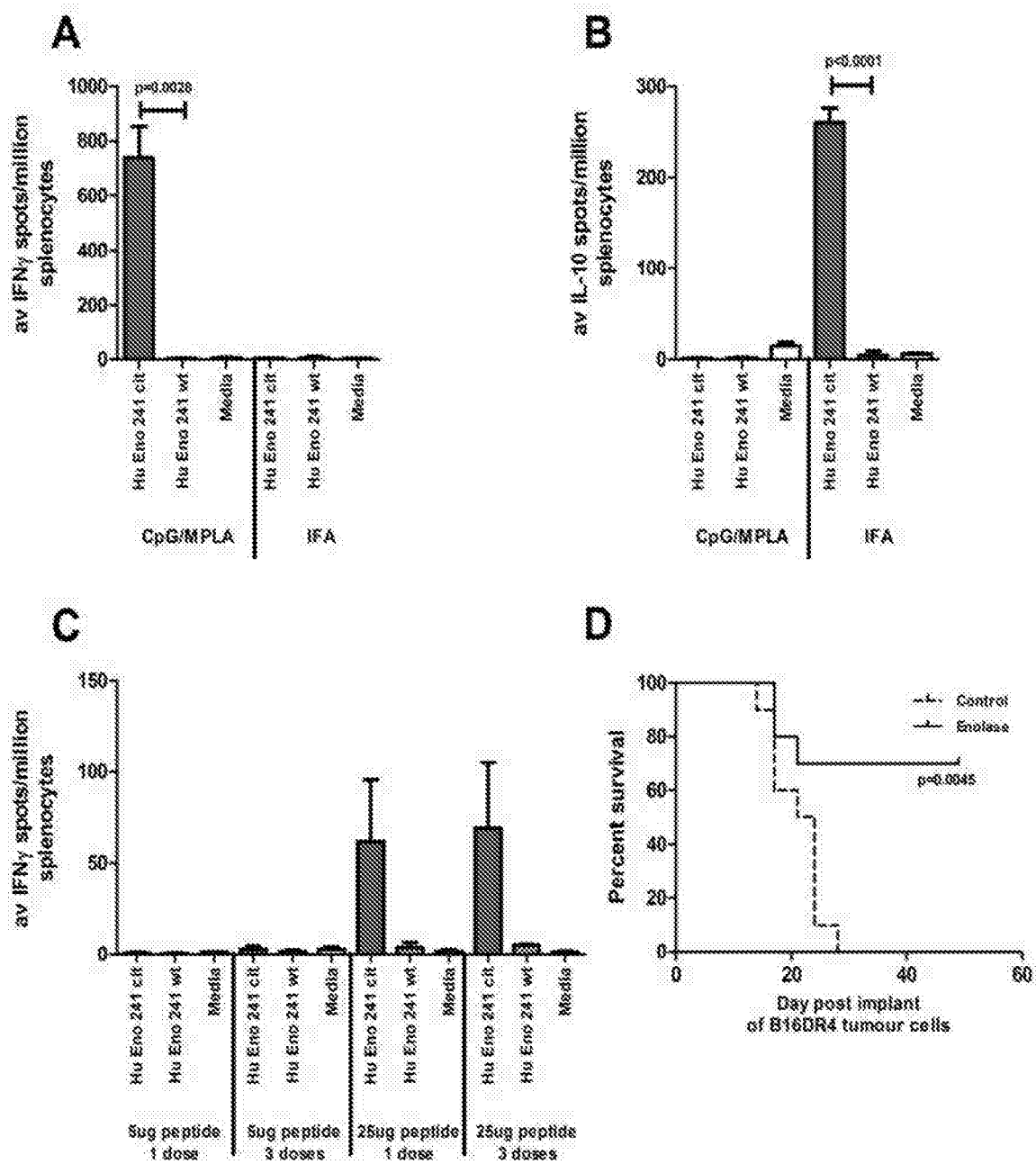

FIG. 9. Adjuvant effects the response induced to Enolase 241cit peptide.

DR4 mice were given a single immunisation of human Enolase 241cit in the presence of adjuvant CpG/MPLA or IFA. IFNγ (A) and IL-10 (B) responses were determined by ex vivo Elispot. For these studies n=3. IFNγ responses in mice given a single or three immunisation of 5 μg or 25 μg of Enolase 241cit peptide in the presence of GM-CSF were determined (C). For these studies n=3. DR4 mice were also challenge with B16DR4 tumour and survival (D) of unimmunised control animals or animals immunised with 3 doses of 5 μg of Enolase 241cit peptide with GM-CSF beginning four days after tumour implant were determined. n=10.

Figure 10:
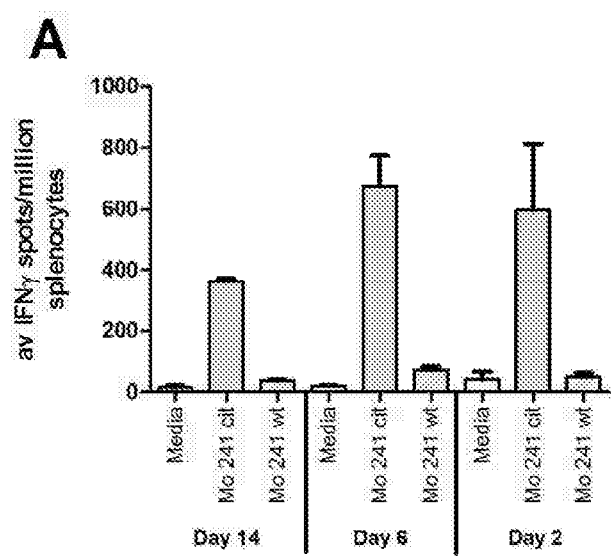

FIG. 10. Responses develop rapidly suggesting a pre-existing Enolase 241cit response.

DR4 mice were immunised with a single dose of Enolase 241cit peptide in CpG/MPLA 2, 6 or 14 days before mice were sacrificed and ex vivo Elispots were used to determine the IFNγ responses. n=3, p values represent significant difference compared to peptide responses at day 2.

Figure 11:
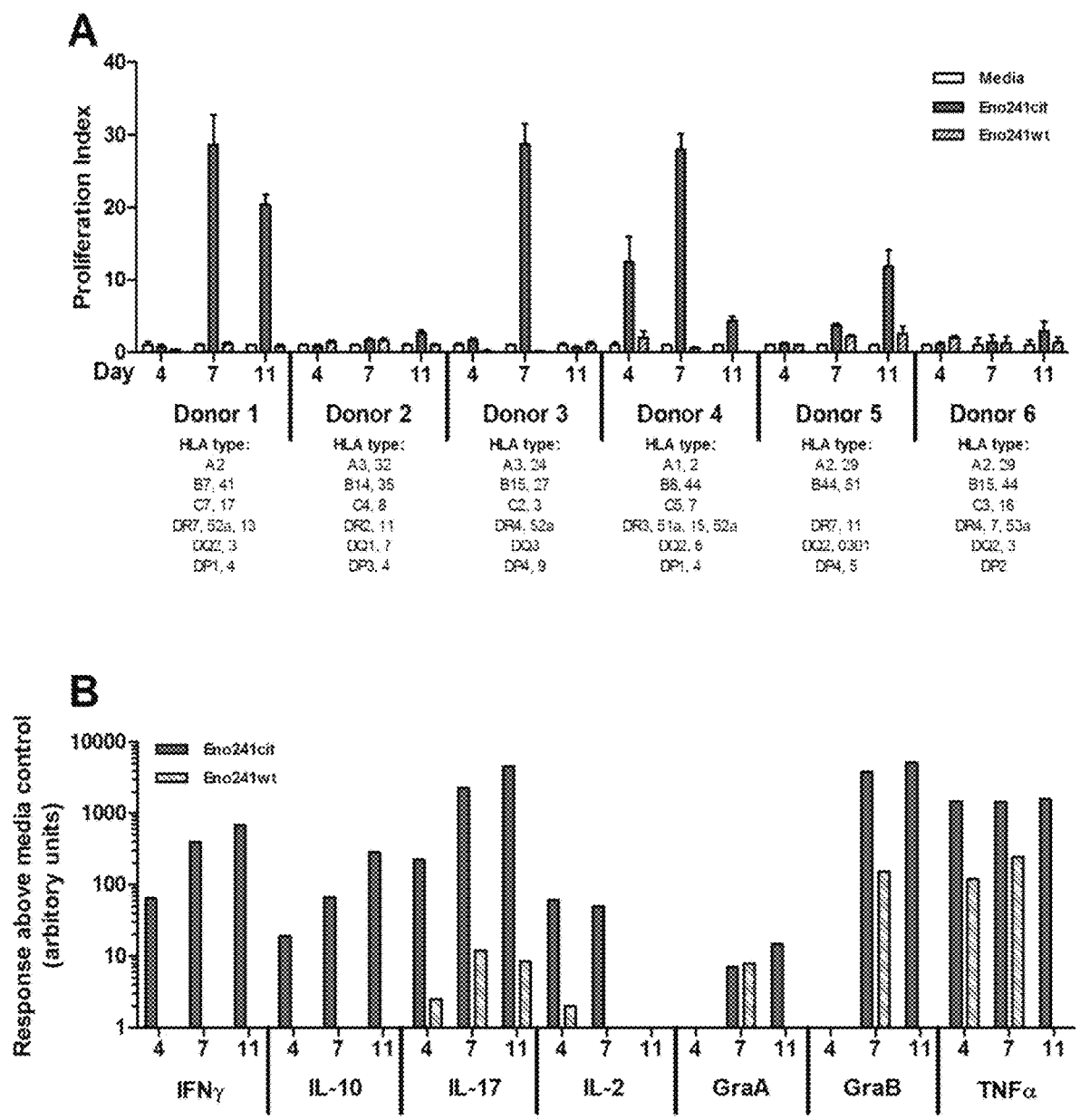
Figure 11:
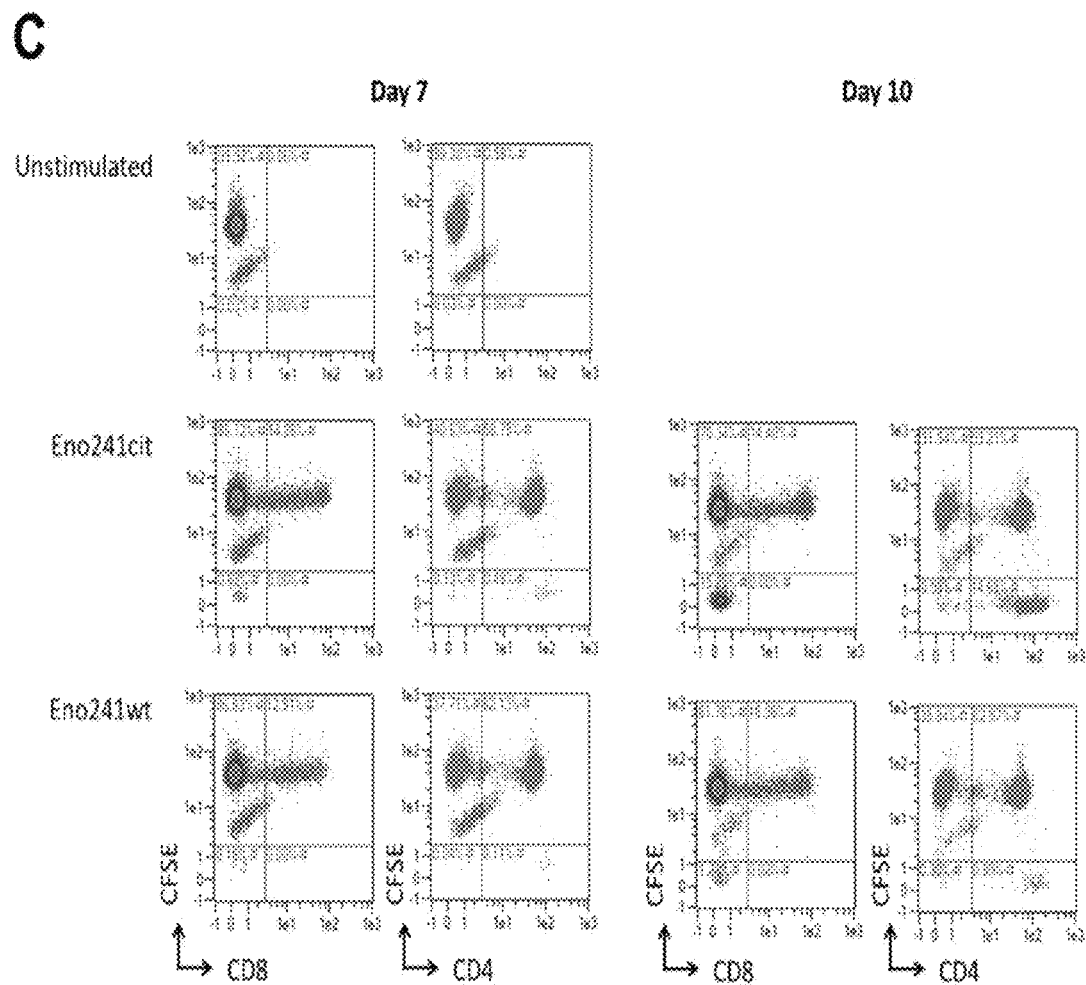

FIG. 11. Enolase 241cit peptide induces responses in Human PBMCs.

PBMCs were isolated from 6 healthy donors and cultured with media, human Enolase 241cit or Enolase 241 wt peptide. Thymidine assays were performed to determine proliferation after 4, 7 and 11 days (A). HLA typing was performed on each donor. Supernants from donor 4 on day 11 were collected and analysed for cytokine levels using luminex (B). Data shown represents response above media control background for each cytokine. PBMCs from donor 4 were labelled with CFSE prior to stimulation with wild type and citrullinated peptides. The CD4 and CD8 populations within the CFSE labelled cell population was assessed for the peptide stimulated samples by flow cytometry at day 7 and day 10 (C).

Figure 12:
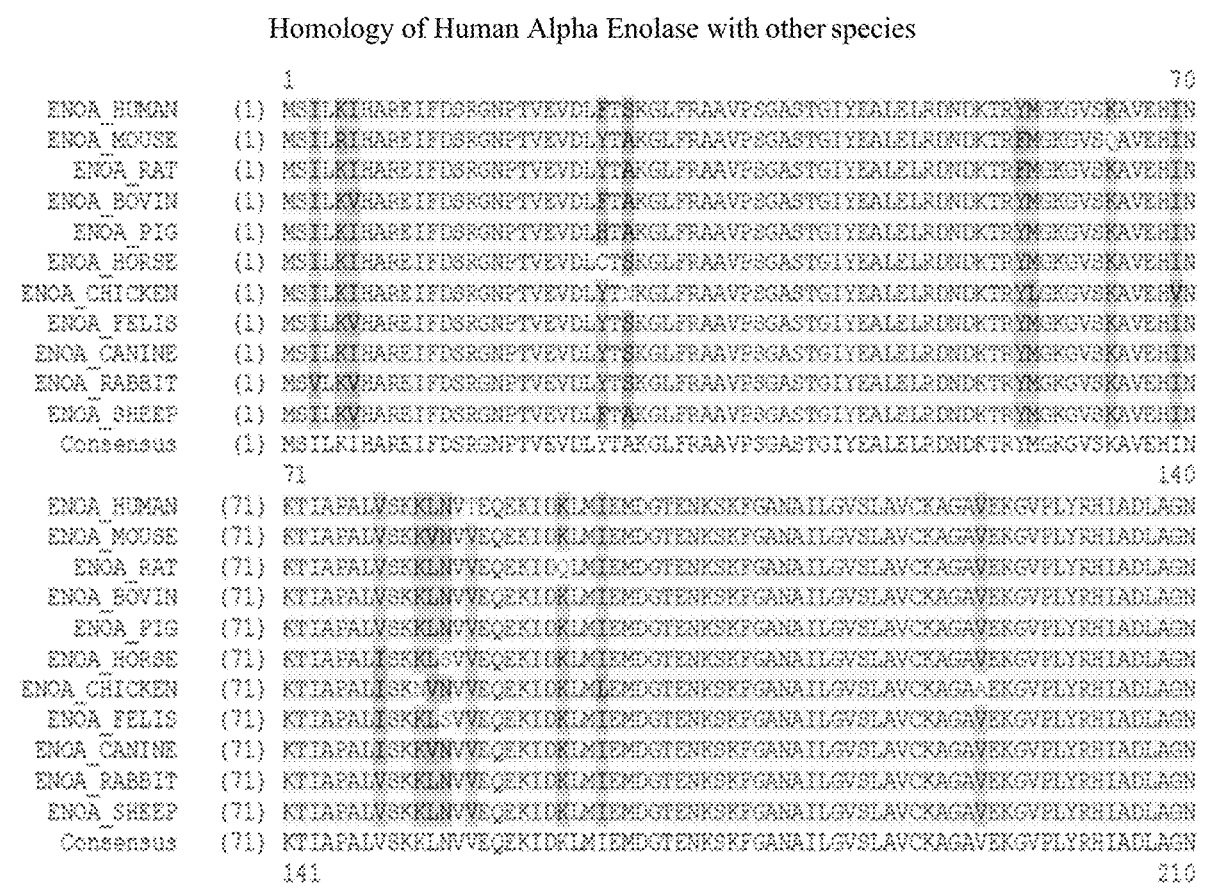

FIG. 12. Alignment of Human Enolase a (ENOA) subunit with equivalent sequences from other species (Mouse, Rat, Cow, Pig, Horse, Chicken, Cat, Dog, Rabbit and Sheep) depicting homology.

FIG. 13. Alignment of) Human Enolase (3 (ENOB) subunit with equivalent sequences from other species (Mouse, Rat, Cow, Pig, Horse, Chicken, Cat, Dog, Rabbit and Sheep) depicting homology.

FIG. 14. Alignment of Human Enolase γ (ENOG) subunit with equivalent sequences from other species (Mouse, Rat, Cow, Pig, Horse, Chicken, Cat, Dog, Rabbit and Sheep) depicting homology.

FIG. 15. Human Enolase 241-260 citrullinated peptide induces CD4 responses.

DR4 transgenic mice were immunized with human 241cit peptide. Ex vivo Elispot was used to determine the IFNγ responses generated to the human and mouse equivalent citrullinated (cit) peptides and the wild type (wt) sequences. IFNγ responses to citrullinated peptides in the presence of MHC class II blocking antibody (L243), CD4 blocking antibody or CD8 blocking antibody (A) or in CD4 depleted or enriched cell fractions (B) were assessed. IFNγ responses to shorter peptide sequences were also tested (C). For all assays media only responses were used as a negative control. For each experiment n=3. p values are shown.

Figure 16:
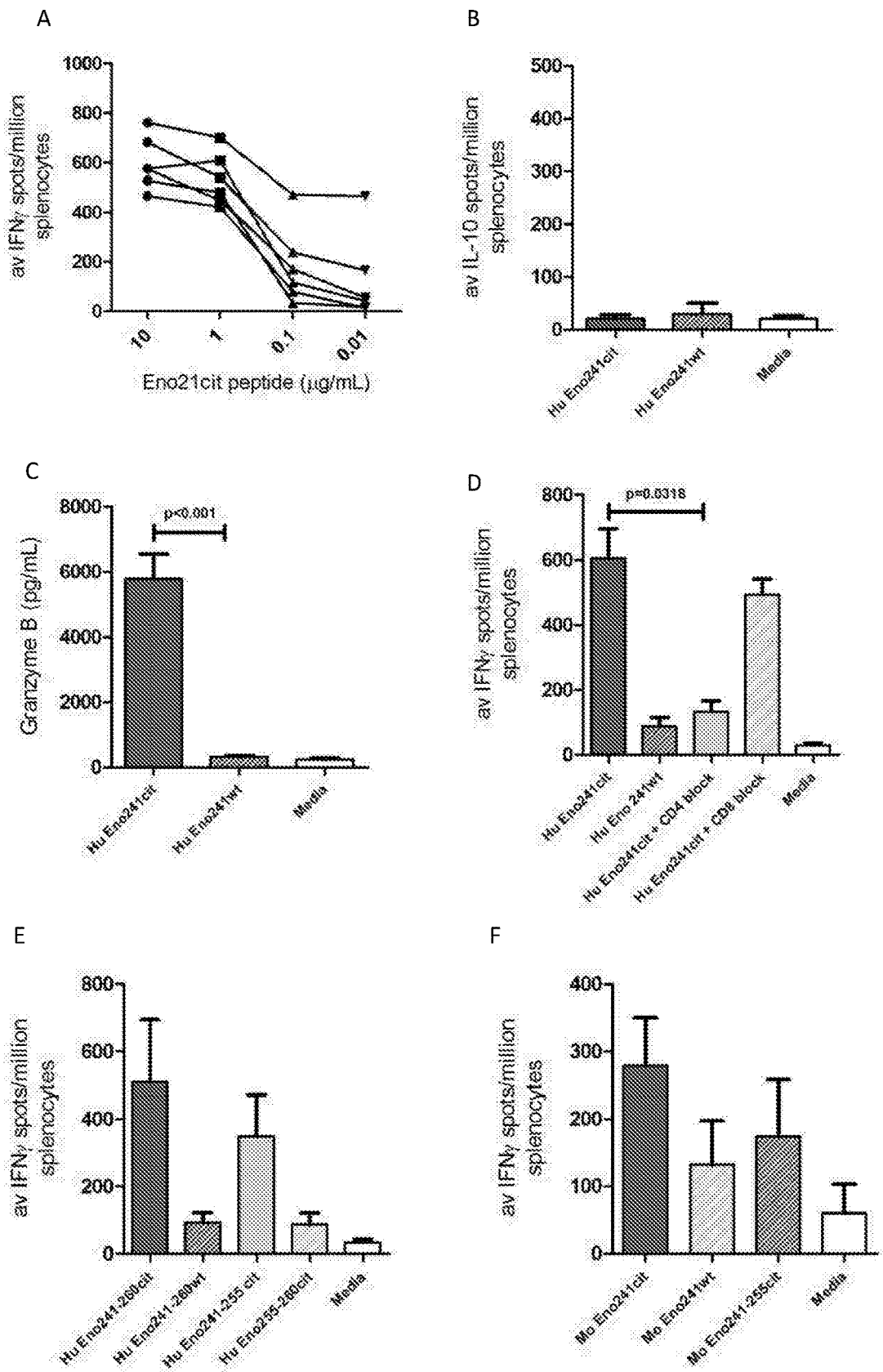

FIG. 16. Characterisation of responses in HHDII/DP4 mice.

Transgenic DP4 mice were immunised with three doses of human (A-E) or mouse (F) Enolase 241cit peptide over three weeks. Splenocytes were collected 21 days after the initial dose was administered. Ex vivo IFNγ Elispot were used to determine the response to Enolase 241 peptides. Responses to the human peptide were tested for avidity by peptide titration (A), IL-10 secretion (B) and Granzyme B secretion (C). IFNγ responses in the presence of CD4 blocking antibody (D) and to shorter peptide sequences were also tested (E). For all assays media only responses were used as a negative control. For each experiment n=3. p values are shown.

Figure 17:
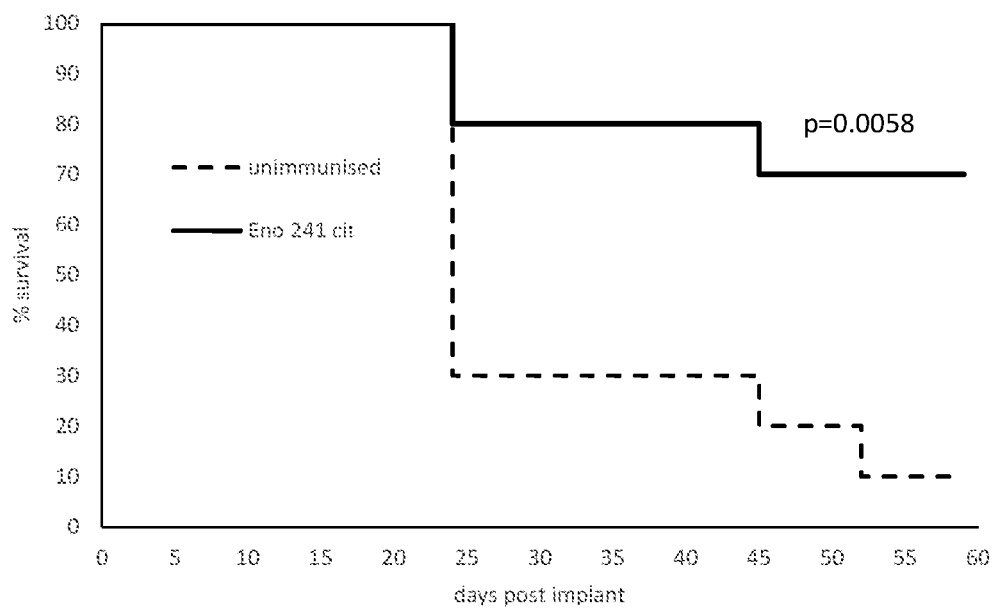

FIG. 17. Human Enolase 241cit peptide provides an in vivo survival advantage in B16 melanoma anti-tumour studies in HHDII/DP4 transgenic mice.

DP4 transgenic mice were challenged with B16DP4 tumour. Survival is shown for unimmunised control animals and animals immunised with Enolase 241cit peptide four days after tumour implant. n=10. Statistical differences between immunised and unimmunised control mice were determined by Mantel-Cox test, p values are shown, n=10.

Figure 18:
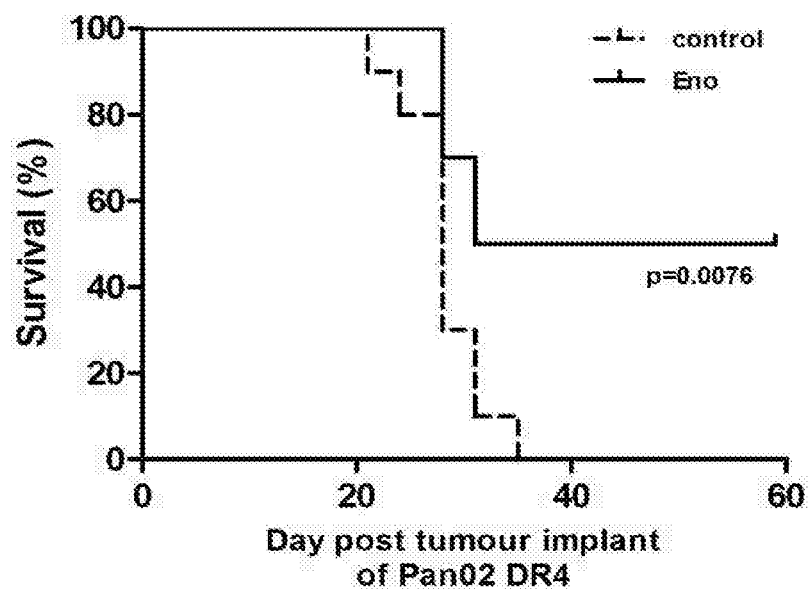

FIG. 18. Enolase 241cit peptide provides a survival advantage Pan02 (pancreatic) tumour model.

DR4 transgenic mice were challenged with the Pan02 pancreatic carcinoma line expressing constitutive DR4. Four days after tumour challenge mice were immunised with human Enolase 241cit peptide and survival monitored. Statistical differences between immunised and unimmunised control mice were determined by Mantel-Cox test, p values are shown, n=10.

Figure 19:
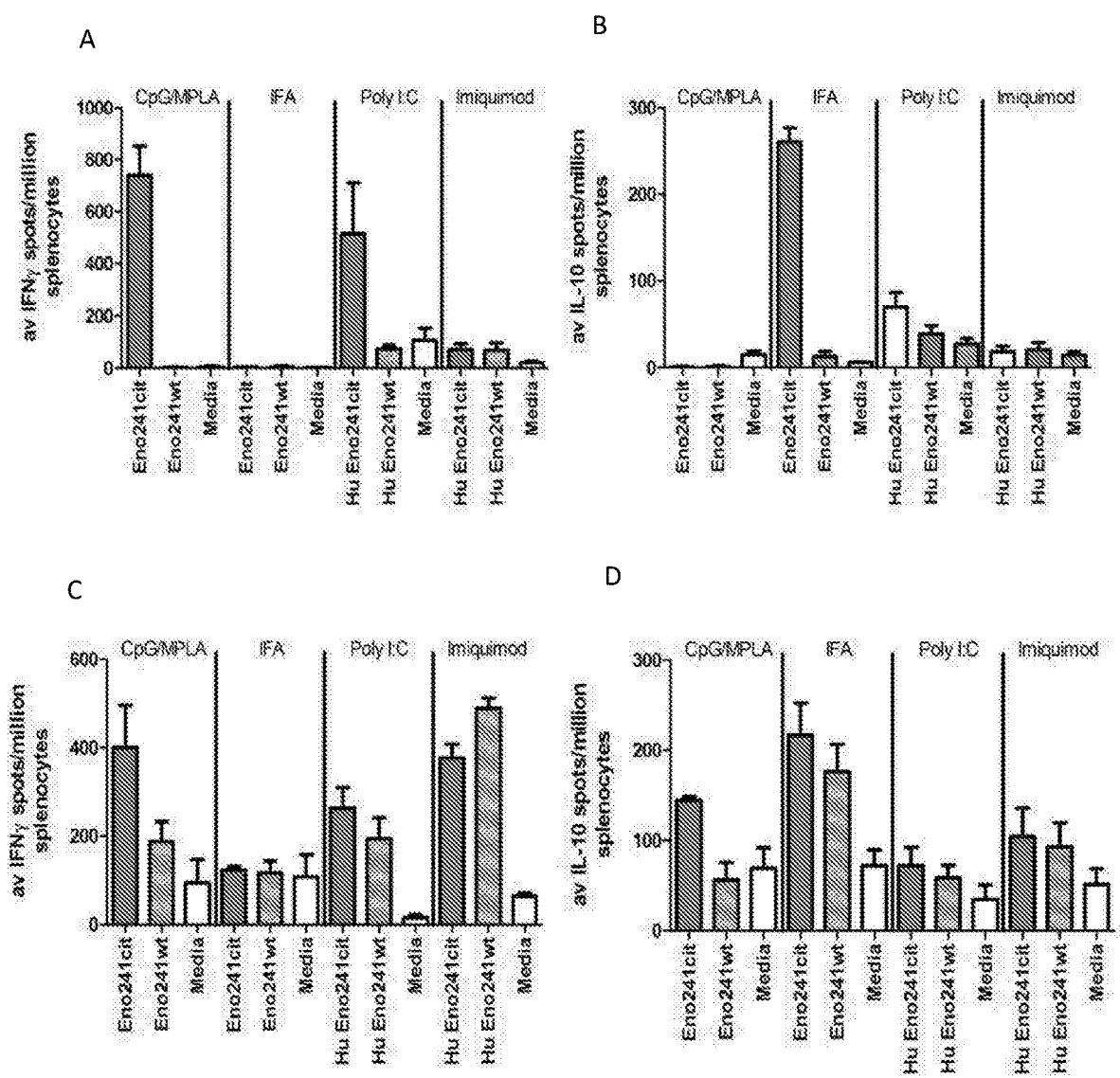

FIG. 19. Response can be induced to Enolase 241cit peptide in combination with a variety of adjuvants.

DR4 (A& B) or HHDII/DP4 (C & D) transgenic mice were immunised with human Enolase 241cit in the presence of adjuvant CpG/MPLA (6 µg each), IFA, Poly I:C (10 µg) or Imiquimod (25 µg). IFNγ (A & C) and IL-10 (B & D) responses were determined by ex vivo Elispot. For these studies n=3.

FIG. 20. Enolase 241cit specific responses reactivated from normal donors produce predominantly Th1 cytokines and are CD4 mediated.

PBMCs from donors 1 and 4 were cultured with human enolase 241cit or wt peptide and IFNg release measured in IFNγ elispot at day 13 (A). IFNγ responses were analysed by intracellular cytokine staining in combination with CD4 and CD8 markers (B). Supernatant from PBMC cultures of donors 1, 4 and 7 were analysed for cytokine levels at days 2, 5 and 12 by luminex assay (C).

FIG. 21. Eno 21cit peptide induces CD4 responses in mice.

C57Bl/6 mice were immunized with human enolase 21cit peptide. Ex vivo Elispot was used to determine the IFNγ responses generated to the human citrullinated (cit) peptide and the wild type (wt) sequences (A). IFNγ responses to citrullinated peptides in the presence of CD4 blocking antibody or CD8 blocking antibody (B) were assessed. For all assays media only responses were used as a negative control. For each experiment n=3. p values are shown.

FIG. 22. Eno 11cit peptide induces CD4 responses in mice.

C57Bl/6 mice were immunized with human enolase 11cit peptide. Ex vivo Elispot was used to determine the IFNγ responses generated to the human and mouse citrullinated (cit) peptides and the human wild type (wt) sequences (A). IL-10 responses to the human cit peptide were assessed (B). IFNγ responses to human citrullinated peptide in the presence of CD4 blocking antibody or CD8 blocking antibody (C) were assessed. For all assays media only responses were used as a negative control. For each experiment n=3. p values are shown.

Methods 2.1. Commercial mAbs

Anti-HLA-DR antibody (clone L243) was purified from HB-55 hybridoma cells (ATCC, USA) culture supernatant by sepharose protein G affinity chromatography. The antibody Rabbit monoclonal [EPR10864 (B)] to ENO1 was used. Anti-mouse CD4 (clone GK1.5) and anti-mouse CD8 (clone 2.43) were purchased from BioXcell, USA.

2.2. Cell Lines

The murine melanoma B16F1 and murine Lewis lung carcinoma LLC/2 cell lines were obtained from the ATCC. The murine Pan02 cell line was obtained from the National Cancer Institute tumour repository. The B16F1 cell line is cultured in RPMI medium 1640 (GIBCO/BRL) and LLC/2 and Pan02 in DMEM. Both are supplemented with 10% FCS, L-glutamine (2 mM) and sodium bicarbonate buffered unless otherwise stated.

2.3. Immunogens 2.3.1. Peptides

Peptides >90% purity were synthesized by Genscript (New Jersey, USA). Stored lyophilized in 0.2 mg aliquots at −80° C. On day of use they were reconstituted to the appropriate concentration in PBS.

2.4. Plasmids

The mammalian expression vector pCMVSPORT6 encoding murine alpha Enolase (ENO-1) full length cDNA (IMAGE ID 5376359) was obtained from Source Bioscience.

To construct the plasmid pVITRO2 Human HLA-DP4, the nucleotide sequence encoding the full length human HLA-DPA*0103 alpha chain flanked by FsprEcoRI and the HLA-DPB*0401 beta chain flanked by BamHI/SalI restriction sites were synthesized. Following sequence confirmation, the HLA-DPA*0103 chain was cloned into the FsprEcoRI mcs2 of the vector pVITRO2-hygro-mcs (Invivogen). The HLA-DPB*0401 chain was subsequently inserted into the BamHI/SalI mcslof the mammalian expression vector alongside the alpha HLA-DPA*0103 chain present within mcs2.

To generate the HHDII plasmid, cDNA was synthesized from total RNA isolated from EL4-HHD cells. This was used as a template to amplify HHD using the forward and reverse primers and sub cloned into pCR2.1. The HHD chain, comprising of a human HLA-A2 leader sequence, the human β2-microglobulin (β2M) molecule covalently linked via a glycine serine linker to the α 1 and 2 domains of human HLA-0201 MHC class 1 molecule and the a3, transmembrane and cytoplasmic domains of the murine H-2Db class 1 molecule, was then inserted into the EcoRV/HindIII sites of the mammalian expression vector pCDNA3.1 obtained from Invitrogen.

To generate the plasmid pVitro 2 Chimeric HLA-DR401 cDNA was generated from mRNA isolated from the splenocytes of transgenic HLA-DR4 mice. This was used as a template to amplify the chimeric alpha and beta chains separately using forward and reverse primers that incorporated a FsprEcoRI and BamHI/SalI sites respectively. On sequence confirmation full length chimeric alpha chain comprising of murine H2-Ea with human HLA-DRA alpha 1 domain was ligated into the FspI/EcoRI mcs2 of the vector pVITRO2-hygro-mcs (Invivogen). The beta chain comprising of murine H2-Eb with human DRB1*0401 Beta 1 domain was then inserted into the BamHI/SalI mcsl of the vector alongside the chimeric alpha chain.

To construct the IFNγ inducible plasmid pDCGAS chimeric HLA-DR401, the chimeric alpha and beta chains, were cloned into the pDCOrig vector described elsewhere (Metheringham et al., 2009) in replacement of the heavy and light chain. The IFNγ inducible promoter consisting of a TATA box and the GAS (IFNγ activated sequence) direct repeat enhancer element was amplified by PCR utilizing the vector pGAS-Luc (Agilent) as a template. The CMV promoter within each cassette was excised and replaced with the IFNγ inducible promoter driving expression of the HLA-DR401 chains within the pDCOrig vector backbone. Endotoxin free plasmid DNA was generated using the endofree Qiagen maxiprep kit (Qiagen, Crawley)

2.5. Transfection

LLC2 cells were transfected using the Lipofectamine transfection reagent (Invitrogen) with 4 µg of the plasmid pVitro 2 Chimeric HLA-DR401 that encodes both full length chimeric alpha and beta chains according to the manufacturer's instructions. The B16F1 cell line previously knocked out for murine MHC class II by Zinc finger Technology (Sigma Aldrich) was transfected with either the pDC GAS chimeric HLA-DR401 or the pVitro 2 chimeric HLA-DR401 plasmids where chimeric HLA-DR401 is under expression of the IFNγ inducible promoter or the constitutive promoter that drive high level expression respectively. Transfected cells were selected by growth in the presence of Hygromycin B (300 µg/ml) or zeocin (300

μg/ml). Lines were cloned by limiting dilution and expression was confirmed by flow cytometry using the anti-human HLA-DR PE-Cy7 conjugated antibody (clone L243) from eBioscience. Cells transfected with the IFNγ inducible plasmid where incubated overnight in the absence or presence of murine IFNγ (30 ng/ml, Gibco life technologies) prior to staining with the antibody.

The B16F1 cell line previously knocked out for murine MHC class I and II by Zinc finger Technology (Sigma Aldrich) was transfected using the Lipofectamine transfection reagent (Invitrogen) with 4 μg of each of the plasmids pCDNA3 HHDII and pVITRO2 Human HLA-DP4 plasmids. Transfected cells were selected by growth in the presence of G418 (500 μg/ml) and Hygromycin B (300 μg/ml). Lines were cloned by limiting dilution and expression was confirmed by flow cytometry using the anti-human beta 2 microglobulin FITC and anti-human HLA-DR/DP/DQ (clone WR18) PE antibodies from Serotec and Abcam respectively.

2.6 Western Blotting

Cell lysates were prepared in RIPA buffer containing protease inhibitor cocktail (Sigma) and proteins separated on a 4-12% NuPAGE Bis-Tris gel (Invitrogen) followed by transfer onto PVDF membrane. The membrane was blocked for 1 hour with 3% BSA then probed with antibodies to human/mouse ENO-1 (clone EPR10863(B), Abcam) 1 in 1000 and β actin (clone AC-15, Sigma) 1 in 15000. Proteins were visualised using the fluorescent secondary antibody IRDye 800RD against rabbit (for ENO-1) and IRDye 680RD secondary anti mouse (for β actin). Membranes were imaged using a Licor Odyssey scanner.

2.7. Immunisations 2.7.1. Immunisation Protocol

C57BL/6 mice (Charles River, UK), HLA-DR4 mice (Taconic, USA), HHDII/DR1 mice (Pasteur institute, France) and the HHD/HLA-DP4 transgenic strain of mouse as described in patent WO2013/017545 A1 (EMMA repository, France) were used, aged between 8 and 12 weeks, and cared for by the staff at Nottingham Trent University. All work was carried out under a Home Office project licence. Peptides were dissolved in PBS to 1 mg/ml and then emulsified (a series of dilutions) with different adjuvants: CpG and MPLA 6 μg/mouse of each (Invivogen, UK), Incomplete Freund's SOW/mouse (Sigma, UK), poly I:C 10 μg/mouse (Invivogen, UK), Imiquimod 25 μg/mouse (Invivogen, UK) and GMCSF 10 μg/mouse (Peprotech, UK). Peptides (25 μg/mouse) were injected subcutaneously at the base of the tail. DNA (1 μg/mouse) was coated onto 1.0 μm gold particles (BioRad, Hemel Hempstead, UK) using the manufacturer's instructions and administered intradermally by genegun (BioRad). Homspera (10 nM/mouse) (PeptideSynthetics, UK) was injected intradermally with genegun immunisation. Mice were immunized at either day 0 for peptide immunisation or days, 0 and 7 for genegun immunisation, unless otherwise stated. Spleens were removed for analysis at day 14 for peptide and day 20 for peptide or genegun immunisation unless stated otherwise.

For tumour challenge experiments mice were challenged with $2.5 \times 10^4$ B16 DR4 cells or $1 \times 10^6$ LLC2/LLC2 DR4 cells, $2.5 \times 10^5$ Pan02 DR4 cells in matrigel or $4 \times 10^5$ B16 HHDII DP4 cells subcutaneously on the right flank 3 days prior to primary immunisation and then were immunised as above. Tumour growth was monitored at 3-4 days intervals and mice were humanely euthanized once tumour reached >10 mm in diameter.

2.8. Analysis of Immune Response 2.8.1. Ex Vivo Elispot Assay

Elispot assays were performed using murine IFNγ, IL-17 and IL-10 capture and detection reagents according to the manufacturer's instructions (Mabtech, Sweden). In brief, anti-IFNγ, IL-17 and IL-10 antibodies were coated onto wells of 96-well Immobilin-P plate. Synthetic peptides (at a variety of concentrations) and $5 \times 10^5$ per well splenocytes were added to the wells of the plate in triplicate. Tumour target cells were added where relevant at $5 \times 10^4$/well in triplicate and plates incubated for 40 hrs at 3TC. After incubation, captured IFNγ and IL-10 were detected by biotinylated anti-IFNγ and IL-10 antibodies and developed with a streptavidin alkaline phosphatase and chromogenic substrate. Spots were analysed and counted using an automated plate reader (Cellular Technologies Ltd).

2.8.2 Luminex Multiplexed Assay

A three-step indirect procedure was used for the multiplexed Luminex assay (Invitrogen) for IgG antibodies to IL-10, IL-17, TNFα, IL-2 & IL-4. Standard, control, and unknown sera were diluted 1:2 in 50% assay diluent buffer (Invitrogen) & 50% serum free RPMI. Serial standard dilutions were included in each assay. Each dilution of standard, control, and unknown sera was mixed with a set of coupled Luminex microspheres in 96-well filtration plates (Millipore Multiscreen; Millipore Corporation, Bedford, Mass.) and incubated for 2 hours at room temperature with shaking. Microspheres were collected by vacuum filtration and washed with PBST. Biotinylated detector antibody was added to each well for 1 hour at room temperature with shaking. Microspheres were collected by vacuum filtration and washed with PBST. Streptavidin conjugated R-phycoerythrin—was added to each well. Following a 30 minute incubation and a wash step, microspheres were resuspended in PBST, and read in a Biorad BioPlex Luminex analyzer equipped with an XY platform. Data acquisition and analysis performed with Luminex software (BioPlex Systems)

2.8.3 Proliferation Assay (Thymidine)

PBMC were isolated from freshly drawn heparinised blood bye Ficol-Hypaque (Sigma) gradient centrifugation. PBMC ($1.5 \times 10^6$ cells/well) were stimulated with single peptides (final concentration 10 μg/ml) in RPMI containing 5% pooled autologous human serum, 2 mM glutamine, 20 mM HEPES and Penicillin-streptomycin (1%) in a final volume of 2 ml. Stimulation with purified protein derivative, PPD (final concentration 10 μg/ml) served as a positive control for the proliferative capacity of PBMC. As a negative control PBMC were incubated with medium alone. The PBMC were cultured at 37° C. in an atmosphere of 5% $CO_2$ for 4, 7 and 11 days. To assess proliferation at these times points 100 μl in triplicate from each culture was aliquoted into a round bottom well of a 96 well plate and $^3$H-thymidine added (0.0185 MBq/well) and incubated at 37° C. for a further 8 hours. The cultures were harvested onto unifilter plates and incorporation of $^3$H-thymidine was determined by β-scintillation counting. The results were assessed by calculating the stimulation index (SI) as the ratio of the mean of counts per minute (cpm) of epitope-stimulated to the mean of unstimulated cultures. The proliferative assay was considered positive when SI>2.5.

2.8.4 Proliferation Assay (CFSE)

PBMC were isolated from freshly drawn heparinised blood by Ficol-Hypaque (Sigma) gradient centrifugation. PBMC ($1.5 \times 10^6$ cells/well) were stimulated with single peptides (final concentration 10 μg/ml) in RPMI containing 5% pooled autologous human serum, 2 mM glutamine, 20 mM HEPES and Penicillin-streptomycin (1%) in a final volume of 2 ml. As a negative control PBMC were incubated with medium alone. The PBMC were cultured at 37° C. in an atmosphere of 5% $CO_2$ for 7 and 10 days. To assess proliferation at these times points cells were sampled and stained with surface marker CD4 and CD8 antibodies labelled with PE-Cy5 and efluor 450 respectively. After staining cells were fixed and analysed on a Milteny MAC-SQuant flow cytometer.

2.8.5 PBMC Culture and IFNγ Elispot

PBMC were isolated from freshly drawn heparinised blood by Ficol-Hypaque (Sigma) gradient centrifugation. PBMC ($1.5 \times 10^6$ cells/well) were stimulated with single peptides (final concentration 10 μg/ml) in RPMI containing 5% pooled autologous human serum, 2 mM glutamine, 20 mM HEPES, Penicillin-streptomycin (1%), 10 ng/ml recombinant human IL-15 and 5 ng/ml recombinant human IL-7 in a final volume of 2 ml. Recombinant human IL-2 was added on day 3 at 20 IU/ml. On day 13 cells were washed and added to human IFNγ elispot assay. Elispot assays were performed using human IFNγ capture and detection reagents according to the manufacturer's instructions (Mabtech, Sweden). In brief, anti-IFNγ antibody was coated onto wells of 96-well Immobilin-P plate. Synthetic peptides (at 10 μg/ml) and $1 \times 10^5$ per well PBMCs were added to the wells of the plate in quadruplicate and plates incubated for 20 hrs at 3TC. After incubation, captured IFNγ was detected by biotinylated anti-IFNγ antibody and developed with a streptavidin alkaline phosphatase and chromogenic substrate. Spots were analysed and counted using an automated plate reader (Cellular Technologies Ltd).

2.8.6 Intracellular Cytokine Analysis

PBMC cultures were set up as detailed above. On day 14 PBMCs were washed and cultured with synthetic peptide (10 μg/ml) in the presence of brefeldin A for 20 hrs at 37° C. Cells were stained with cell surface markers CD4 and CD8 using PE-Cy5 and efluor450 labelled antibodies respectively. Cells were subsequently fixed and permeabilised and stained with IFNγ PE-Cy7 labelled antibody. After staining cells were fixed and analysed on Miltenyi MAC-SQuant flow cytometer.

2.9 Immunohistochemical Analysis

Normal and tumour tissue binding was by immunohistochemistry (IHC) as described previously (Durrant et al., 2006). Immunohistochemical staining was performed on 4 μm sections using Novolink polymer detection system (Leica Biosystems, RE7150-K). Briefly, slides were deparaffinised with xylene and rehydrated through three changes of alcohol, the antigen-retrieval was performed in citrate buffer (pH 6.0) for 20 min using a microwave oven. Endogenous peroxidase activity was blocked by Peroxidase Block for 5 min. Slides were washed with TBS (pH 7.6), followed by the application of Protein Block for 5 min. Following another TBS wash, primary antibody, optimally diluted in Leica antibody diluent (RE7133), was applied and incubated for 60 min. The anti-ENO1 rabbit monoclonal EPR10864 (B) was used at 1/200. Slides were washed with TBS followed by incubation with Post-Primary Block for 30 min followed by a TBS wash. Novolink polymer was applied for 30 min. DAB working solution was made up of 1:20 DAB chromogen in DAB substrate buffer was prepared and applied for 5 min. Slides were counterstained with Novolink haematoxylin for 6 min, and dehydrated.

The TMA slides were initially assessed by light microscope assessment of staining quality and specificity. Slides were then scanned into high-resolution digital images (0.45 μm/pixel) using a NanoZoomer slide scanner (Hamamtsu Photonics, Welwyn Garden City, UK) and accessed using a web-based interface NDP viewer (Nanozoomer Digital Pathology). They were scored at 920 magnification using a minimum of 2400 high-resolution screen (91920 1080). Cases were scored without knowledge of the ENO1 status and patient outcome and were scored by two people (MG and MM). Assessment of staining was based on a semi-quantitative approach using a modified histochemical score (H-score) taking the intensity of staining and the percentage of stained cells into account. For the intensity, a score index of 0, 1, 2, and 3 corresponding to negative, weak, moderate, and strong staining intensity was used, and the percentage of positive cells at each intensity was estimated subjectively. Statistical analysis was performed using SPSS 13.0 (SPSS Inc, Chicago). Stratification cut-points for the survival analysis were determined using X-Tile software (Camp et al., 2004) and P values of <0.05 were considered significant.

Patient Cohorts

The study populations include cohorts of consecutive series of 462 archived colorectal cancer (Simpson et al., 2010) specimens (1994-2000; median follow up 42 months; censored December 2003; patients with lymph node positive disease routinely received adjuvant chemotherapy with 5-flurouracil/folinic acid), 350 ovarian cancer (Duncan et al., 2007) samples (1982-1997; median follow up 192 months: censored November 2005:patients with stage II to IV disease received standard adjuvant chemotherapy which in later years was platinum based), 142 gastric cancer (Abdel-Fatah et al., 2013) samples (2001-2006; median follow up 66 months; censored January 2009; no chemotherapy) 68 pancreatic and 120 billary/ampullary cancer (Storr et al., 2012) samples (1993-2010:median 45 months; censored 2012; 25-46% of patients received adjuvant chemotherapy with 5-flurouracil/folinic acid and gemcitabine) 220 non-small cell lung cancers (01/1996-07/2006: median follow up 36 months censored May 2013; none of the patients received chemotherapy prior to surgery but 11 patients received radiotherapy and 9 patients received at least 1 cycle of adjuvant chemotherapy post-surgery) obtained from patients undergoing elective surgical resection of a histologically proven cancer at Nottingham or Derby University Hospitals. No cases were excluded unless the relevant clinico-pathological material/data were unavailable. This retrospective study was based on a consecutive series of 902 patients with primary invasive breast carcinomas who were diagnosed from 1987 to 1998 and entered onto the Nottingham Tenovus Primary Breast Carcinoma series. This is a well characterised series of patients under the age of 71 years (median 55 years) with long term follow up. All patients were treated in a uniform way in a single institution and have been investigated for a wide range of protein expression.

All patients received standard surgical treatment of either mastectomy or wide local excision with radiotherapy. Before 1988, patients did not receive systemic adjuvant therapy. From 1988 onwards, patients were selected for systemic adjuvant treatment on the basis of NPI score and hormone receptor status. Patents with a NPI<3.4 received no adjuvant therapy; those with an adjuvant score higher than 3.4 received tamoxifen if they were estrogen receptor positive (±goserelin if premenopausal) or classical cyclophosphamide, methotrexate and fluorouracil if they were ER negative and fit enough to tolerate chemotherapy. Survival data was maintained prospectively. Breast cancer specific survival (BCSS) was defined as the time (in years) from the date of the primary surgical treatment to the time of death from breast cancer. Survival was censored if the patient was still alive, lost to follow up (n=73) or died from other causes.

EXAMPLE 1. SEQUENCE ALIGNMENT And HOMOLOGY Of ENOLASES

In mammals there are four isoforms of the enolase enzyme, ENO1 (A); ENO2 (B), ENO3 (G) and ENO4 which are encoded by four distinct genes. They are highly conserved and have a high degree of amino acid homology (FIG. 1).

EXAMPLE 2. CD4 RESPONSES TO CITRULLINATED ENOLASE

The human alpha-Enolase peptide sequence was broken down into overlapping 20-mers. Any 20-mer containing an arginine was selected and the arginine residues were replaced with citrulline (cit). The selected 20mer peptides are summarised in Table 1.

TABLE 1

Enolase peptides utilised.
- indicates mouse and human sequences are homologous
aa that alter in the mouse sequence are highlighted in bold

| Enolase peptide (aa co-ordinates) | Peptide sequences | |
|---|---|---|
| | Human peptide | Mouse homologue |
| 1-20 | MSILKIHA-CIT-EIFDSRGNPTV (SEQ ID NO: 18) | MSILRIHA-CIT-EIFDSRGNPTV (SEQ ID NO: 19) |
| 6-25 | IHA-CIT-EIFDS-CIT-GNPTVEVDLF (SEQ ID NO: 20) | IHA-CIT-EIFDS-CIT-GNPTVEVDLY (SEQ ID NO: 21) |
| 21-40 | EVDLFTSKGLF-CIT-AAVPSGAS (SEQ ID NO: 22) | EVDLYTAKGLF-CIT-AAVPSGAS (SEQ ID NO: 23) |
| 26-45 | TSKGLF-CIT-AAVPSGASTGIYE (SEQ ID NO: 24) | TAKGLF-CIT-AAVPSGASTGIYE (SEQ ID NO: 25) |
| 36-55 | PSGASTGIYEALEL-CIT-DNDKT (SEQ ID NO: 26) | — |
| 46-65 | ALEL-CIT-DNDKT-CIT-YMGKGVSKA (SEQ ID NO: 27) | ALEL-CIT-DNDKT-CIT-FMGKGVSQA (SEQ ID NO: 28) |
| 56-75 | -CIT-YMGKGVSKAVEHINKTIAP (SEQ ID NO: 29) | -CIT-FMGKGVSQAVEHINKTIAP (SEQ ID NO: 30) |
| 121-140 | AGAVEKGVPLY-CIT-HIADLAGN (SEQ ID NO: 31) | — |
| 126-145 | KGVPLY-CIT-HIADLAGNSEVIL (SEQ ID NO: 32) | KGVPLY-CIT-HIADLAGNPEVIL (SEQ ID NO: 33) |
| 171-190 | LPVGAANF-CIT-EAM-CIT-IGAEVYH (SEQ ID NO: 34) | LPVGASSF-CIT-EAM-CIT-IGAEVYH (SEQ ID NO: 35) |
| 176-195 | ANF-CIT-EAM-CIT-IGAEVYHNLKNV (SEQ ID NO: 36) | SSF-CIT-EAM-CIT-IGAEVYHNLKNV (SEQ ID NO: 37) |
| 241-260 | VIGMDVAASEFF-CIT-SGKYDLD (SEQ ID NO: 38) | VIGMDVAASEFY-CIT-SGKYDLD (SEQ ID NO: 39) |
| 246-265 | VAASEFF-CIT-SGKYDLDFKSPD (SEQ ID NO: 40) | VAASEFY-CIT-SGKYDLDFKSPD (SEQ ID NO: 41) |
| 256-275 | KYDLDFKSPDDPS-CIT-YISPDQ (SEQ ID NO: 42) | KYDLDFKSPDDPS-CIT-YITPDQ (SEQ ID NO: 43) |
| 261-280 | FKSPDDPS-CIT-YISPDQLADLY (SEQ ID NO: 44) | FKSPDDPS-CIT-YITPDQLADLY (SEQ ID NO: 45) |
| 316-335 | VGDDLTVTNPK-CIT-IAKAVNEK (SEQ ID NO: 46) | VGDDLTVTNPK-CIT-IAKAASEK (SEQ ID NO: 47) |
| 321-340 | TVTNPK-CIT-IAKAVNEKSCNCL (SEQ ID NO: 48) | TVTNPK-CIT-IAKAASEKSCNCL (SEQ ID NO: 49) |
| 326-345 | K-CIT-IAKAVNEKSCNCLLLKVN (SEQ ID NO: 50) | K-CIT-IAKAASEKSCNCLLLKVN (SEQ ID NO: 51) |
| 361-380 | QANGWGVMVSH-CIT-SGETEDTF (SEQ ID NO: 52) | QSNGWGVMVSH-CIT-SGETEDTF (SEQ ID NO: 53) |
| 366-385 | GVMVSH-CIT-SGETEDTFIADLV (SEQ ID NO: 54) | — |

TABLE 1-continued

Enolase peptides utilised.
-indicates mouse and human sequences are homologous
aa that alter in the mouse sequence are highlighted in bold

| Enolase peptide (aa co-ordinates) | Peptide sequences | |
|---|---|---|
| | Human peptide | Mouse homologue |
| 391-410 | GQIKTGAPC-CIT-SE-CIT-LAKYNQL (SEQ ID NO: 55) | — |
| 396-415 | GAPC-CIT-SE-CIT-LAKYNQLL-CIT-IEE (SEQ ID NO: 56) | GAPC-CIT-SE-CIT-LAKYNQIL-CIT-IEE (SEQ ID NO: 57) |
| 401-420 | SE-CIT-LAKYNQLL-CIT-IEEELGSK (SEQ ID NO: 58) | SE-CIT-LAKYNQIL-CIT-IEEELGSK (SEQ ID NO: 59) |
| 406-425 | KYNQLL-CIT-IEEELGSKAKFAG (SEQ ID NO: 60) | KYNQIL-CIT-IEEELGSKAKFAG (SEQ ID NO: 61) |
| 416-434 | ELGSKAKFAG-CIT-NF-CIT-NPLAK (SEQ ID NO: 62) | ELGSKAKFAG-CIT-SF-CIT-NPLAK (SEQ ID NO: 63) |

Screening of Enolase Peptide Responses

Screening was performed to identify potential citrullinated Enolase epitopes in mice. Mice were immunised with pools of 4-6 human citrullinated peptides. To reduce the effect of possible cross reactivity the peptides within each pool were chosen so that they did not contain any overlapping amino acid sequences. Each pool was administered as a single immunisation containing 20 μg of each peptide and CpG/MPLA as an adjuvant. After 14 days the mice were culled and the immune responses to each peptide within the immunising pool were assessed by ex vivo Elispot (FIG. 2). In addition, the splenocytes were screened against the murine equivalent sequences. We have previously shown that citrullinated peptides can induce responses in the transgenic DR4 mouse strain. Given that different mouse strains have different MHC repertoires a number of strains were used for screening. Peptide responses were assessed in C57BL/6 mice as well as transgenic strains expressing human DR4 or HHD/DR1 in a C57BL/6 background (see materials and methods).

Significant IFNγ responses were detected to a number of different peptides. In the DR4 mice the pool containing the Enolase 241-260 citrullinated peptide induced a significant response to human 241cit (p<0.05) and mouse 241cit (p<0.0001). No other peptides showed significant IFNγ responses in DR4 mice. In the HHD/DR1 mice, the pool with Enolase peptide 126-145 induced a significant response to human 126cit (p<0.05) but not mouse 126cit. The pool with Enolase peptide 316-335 induced a significant response to human 316cit (p<0.05) but not mouse 316cit. The pool containing the peptide Enolase 1-20 did not induced a significant response to human peptide but did induce a response to mouse 1cit (p<0.05). In the C57BL/6 mice, the pool containing the peptide Enolase 21-40 induced a significant response to human 21cit (p<0.05) but not mouse 21cit. The pool with Enolase peptide 126-145 induced a significant response to mouse 126cit (p<0.05) but not human 126cit. The pool with Enolase peptide 261-280 induced a significant response to human 261cit (p<0.05) but not mouse 261cit. This suggests that peptides 21-40, 126-145, 241-260 and 316-335 justified further investigation.

From the initial screen Enolase 241cit immunisation in DR4 mice induced the strongest immune response. Therefore, this peptide was investigated further. DR4 mice were given a single immunisation with 25 μg of the human 241cit peptide and CpG/MPLA. Ex vivo elispot on splenocytes showed a significant IFNγ response to citrullinated peptides compared to media controls for both the mouse (p=0.0008) and human (p=0.0124) sequence (FIG. 3A). The mouse sequence is actually the same sequence as aa241-260 from ENO2 and ENO3 so is still a self-antigen. Interestingly, neither the human or mouse wild type (wt) sequence, where the arginine residue at position 253 has not been replaced with a citrulline, produced an immune response. This confirmed that Enolase 241cit induced a citrulline specific IFNγ response in DR4 mice.

To determine the type of cytokine response generated by Enolase 241cit peptide ex vivo IL-10 was also assayed. No significant increase in IL-10 production was observed in ELISpot assays in response to peptide stimulation (FIG. 3B).

Previously citrullinated peptide specific responses have been shown to be CD4 mediated. To determine whether the response to 241cit is CD4 dependent an Elispot assay was performed with a human MHC class II blocking antibody (clone L243) (FIG. 3C). IFNγ response were significantly reduced by L243 in response to both human Enolase 241cit (p=0.0171) and mouse 241cit (p=0.0023). To further confirm that 241cit specific responses were CD4 mediated Elispot assay was performed including a murine CD4 or CD8 blocking antibody (clone GK1.5 or clone 2.43 respectively) or using CD4 enriched or depleted cell fractions. Responses to human enolase 241cit were significantly reduced in the presence of the CD4 blocking antibody but not the CD8 blocking antibody (FIG. 15A). Responses were also present in the CD4 enriched fraction but not in the CD4 depleted fraction (FIG. 15B).

Since Enolase 241-260 is a long peptide we sought to determine the optimal 15mer sequence that the responses recognize. Two 15mer peptides spanning the 241-260 sequence were tested for responses with aa241-255 stimulating specific responses but no response to aa246-260 (FIG. 15C).

To confirm lower frequency responses seen in initial screens, DR4, C57Bl/6 and HHD/DR1 mice were given a single immunisation of the human citrullinated Enolase peptides corresponding to the sequences at positions 21-40, 126-145 and 316-335 (FIG. 4). Enolase 21cit induced a low level but significant response in DR4 mice to the mouse (p<0.01) but not to the human sequence. In C57Bl/6 mice strong IFNγ responses were observed that respond to the citrullinated but not the wt peptide (FIG. 21a). These appear to be CD4 mediated as they are efficiently blocked by CD4 blocking antibody but not a CD8 blocking antibody (FIG. 21b). Enolase 126cit induced a low level significant response to the human peptide in DR4 mice (p<0.05) but not in DR1/HHD mice. Enolase 316cit induced a moderate response to the human but not the mouse sequence in both DR4 (p<0.01) and DR1/HHD (p<0.01) mice.

Enolase sequences were also subject to in silico analysis for peptide sequences with high binding affinity to human and murine MHC class II using the online IEDB prediction program. This suggested the aall-25 sequence to be strong for murine MHC class II (I-Ab) therefore the citrullinated aall-25 peptide was tested for responses in C57Bl/6 mice. Mice showed IFNγ responses to this citrullinated peptide that cross reacted with the equivalent sequence from the murine sequence with minimal reactivity to the wt peptide (FIG. 22a). No IL-10 responses were seen to the citrullinated eno11 peptide (FIG. 22b). The enolase 11cit specific IFNγ response was mediated by CD4 cells as blocking these with a CD4 blocking antibody abrogated the response whereas use of a CD8 blocking antibody had no effect on the response (FIG. 22c).

To determine whether HLA-DP4 might also be able to present the Enolase 241cit peptide transgenic DP4 mice were utilised. DP4 mice were immunised with three doses of either human or mouse Enolase 241cit peptide. IFNγ responses were determined by Elispot (FIG. 5). Mice immunized with human Enolase 241cit peptides showed responses to both Human Enolase 241cit (p<0.0001) and mouse 241cit (p<0.0001) showed increased IFNγ responses when compared to the wild type peptides (FIG. 5A). These responses show an avidity of between 1 and 0.1 ug/ml peptide (FIG. 16A). Cells from mice immunized with the human 241-260cit peptide show granzyme B release but no IL-10 in response to the cit peptide but not the wt peptide (FIGS. 16B and C). Responses specific for the human 241-260 cit peptide in the DP4 mice are also blocked by a CD4 blocking antibody but not CD8 blocking antibody and show cross reactivity to a shorter peptide spanning aa241-255 (FIGS. 16D and E). Immunisation of DP4 transgenic mice with the murine Enolase 241-260 peptide also induces responses specific to the citrullinated peptide but not the wildtype (FIG. 16F).

EXAMPLE 3: CIT ENOLASE PEPTIDE PRESENTED ON TUMOUR CELLS CAN BE TARGETED FOR TUMOUR THERAPY

We had already established by Western blotting that the melanoma B16F1 and Lewis lung Carcinoma cell lines constitutively express Alpha Enolase (FIG. 6A). Next, the anti-tumour effect of Enolase 241cit peptide immunisation was assessed in vivo. The effect of Enolase immunisation on the growth of the mouse B16 melanoma cell line transfected with constitutive human DR4 (B16DR4) was assessed. Mice were challenged with B16DR4, 3 days prior to immunisation with Enolase 241cit peptide. Enolase 241cit peptide immunised mice showed a significant survival advantaged over control mice (FIG. 6B). Unimmunised mice showed 15% survival after 45 days whereas Enolase 241cit immunised mice showed 50% survival (p=0.0001). The tumour volume (FIG. 6C) was also significantly lower in the Enolase 241cit immunised mice (median 0 mm$^3$) compared to the control group (median 49 mm$^3$) at day 17 post tumour implant (p=0.0043).

Since responses to the 241-260cit epitope have also been demonstrated in DP4 mice, DP4 transgenic mice were challenged with the mouse B16 melanoma line expressing constitutive human DP4 (B16DP4) and subsequently immunized with Enolase 241cit peptide. Enolase 241cit peptide immunized mice showed a significant survival advantage (p=0.0058) over unimmunized mice with survival rates after 60 days of 70% and 10% respectively (FIG. 17).

To determine whether survival is effected by the constitutive expression of MHC class II in this tumour cell line, the anti-tumour effect was assessed in B16 cells where the HLA-DR4 expression is IFNγ inducible (iDR4). Mice were challenged with B16iDR4 4 days prior to immunisation with Enolase 241cit peptide (FIG. 6D). Survival was significantly increased in the Enolase 241cit immunised group (90%) compared to the unimmunised control animals (survival 0%) at day 42 (p<0.0001). The tumour volume at day 17 post tumour implant (FIG. 6E) was also significantly lower in the Enolase 241cit (median 0 mm$^3$) compared to unimmunised control mice (median 65 mm$^3$, p=0.0048). Given the high survival percentage in the immunised group these mice were rechallenged with B16iDR4 at day 42 to see if memory had been established. New untreated mice were also challenged with tumour as a control group. Enolase immunised survivors showed a significant survival advantage on rechallenge compared to previously untreated control mice (FIG. 6F). 39 days after the rechallenge survival in the Enolase 241cit immunised group was 67% while all of the control group were dead by day 29 (p=0.0112).

To determine whether this anti-tumour effect is specific to the B16DR4 model, mice were next challenged with the Lewis lung carcinoma cell line LLC2 (FIG. 7A). Preliminary studies suggested that a higher implant cell number was required to obtain consistent growth of the LLC2 cells compared to B16 cells (data not shown). For this reason, in our hands the LLC2 model is more aggressive than the B16 model. Mice were challenged with parental LLC2 or LLC2 transfected to constitutively express DR4 (LLCDR4) four days before immunisation with Enolase 241cit peptide. Survival data shows that Enolase 241cit immunisation provided a survival advantage against the LLCDR4 tumour (p=0.0142) with 40% of mice surviving today 58 compared to the control where all mice died by day 48. However, in mice challenged with the parental LLC2 tumour while Enolase 241cit immunised mice showed a small but significant increase in survival time (p=0.0005). These results suggest that human DR4 expression on tumour cells is important for tumour rejection in this model.

Enolase is also expressed by the pancreatic tumour line Pan02 (FIG. 6A). This line was engineered to constitutively express HLA-DR4 and DR4 transgenic mice were challenged with tumour followed 4 days later by immunization with Enolase 241cit peptide. Enolase 241cit peptide immunized mice show significantly enhanced survival (p=0.0076) in the Pan02 DR4 model compared to unimmunized control DR4 mice. 50% of mice show survival at day 60 compared to none of the unimmunized mice (FIG. 18).

EXAMPLE 4. DNA IMMUNISATION RESULTS IN RESPONSES TO CITRULLINATED ENOLASE

As APCs can constitutively citrullinate epitopes it was possible that a DNA construct encoding Enolase may be citrullinated and stimulate a response. HLA-DR4 transgenic mice were therefore immunised with a DNA construct encoding mouse enolase. Stimulated T cells from these mice were screened in vitro for IFNγ, responses to both citrullinated and uncitrullinated enolase 241 peptide. FIG. 8A shows that mice only responded to the citrullinated mouse peptide (mean: IFNγ 180/million splenocytes; p=0.0001). No I1-10 response was observed (FIG. 8B).

Next, the anti-tumour effect of Enolase DNA immunisation was assessed in vivo. Mice were challenged with B16DR4 four days prior to immunisation with Enolase DNA. Enolase DNA immunised mice showed a significant survival advantaged over control mice (FIG. 8C). Unimmunised showed 15% survival after 45 days whereas Enolase DNA immunised mice showed 60% survival (p=0.0001). The tumour volume (FIG. 8D) was also significantly lower in the Enolase DNA immunised mice (median 20 $mm^3$) compared to the control group (median 150 $mm^3$) at day 17 post tumour implant (p=0.0088).

EXAMPLE 5. DETERMINATION OF WHETHER CD4 RESPONSES TO ENOLASE PEPTIDES VARY WHEN COMBINED WITH DIFFERENT ADJUVANTS AND AT DIFFERENT DOSES

Enolase 241cit peptide induces a strong IFNγ response when administered as a single 25 ug dose with the adjuvant CpG/MPLA. The effect of adjuvant and dose regime on the response generated was investigated. Mice were immunised with a single dose of Enolase 241cit peptide with either CpG/MPLA or incomplete Freund's adjuvant (IFA) as the adjuvant. IFNγ responses to Enolase 241cit peptides were detected by Elispot when CpG/MPLA (p=0.0028) was the adjuvant but no IFNγ response was seen when IFA was used as an adjuvant (FIG. 9A). IL-10 responses were detected by Elispot when Enolase 241cit peptide was administered with IFA (p<0.0001) but not CpG/MPLA (FIG. 9B). In addition to these adjuvants responses in combination with other TLR agonists Poly I:C (TLR3) and imiquimod (TLR7) were assessed in both DR4 and DP4 transgenic mice. The combination with poly I:C induces IFNγ responses in both mouse strains but no IL-10 (FIG. 19). Enolase 241cit peptide combined with imiquimod induces IFNγ responses in DP4 transgenic mice but not in DR4 transgenic mice (FIG. 19). This suggests that the type of cytokine response generated by immunisation with Enolase 241cit peptide can be strongly affected by the adjuvant selected.

Next, dose responses to immunisation with GM-CSF were assessed. Mice were given a single or three immunisations with either 25 μg or 5 μg of Enolase 241cit peptide. IFNγ responses were assessed by Elispot (FIG. 9C). Detectable responses could be observed after 1 or 3 doses with 25 μg of peptide. Next mice were challenged with B16DR4 and then given three doses of 5 μg of Enolase in GM-CSF over three weeks, to determine whether this is sufficient to induce an anti-tumour response (FIG. 9D). Enolase 241cit immunised mice had a significant survival advantage over control mice (p=0.0045) with 70% of animals surviving at day 45 compared to 0% in the control group by day 28.

EXAMPLE 6. ENOLASE 241CIT MEMORY RESPONSES

The ability of different adjuvants to polarise the responses to immunisation with Enolase 241cit peptide may suggest plasticity of the T-cell population involved. This may indicate a pre-existing or memory response. Therefore, next the speed with which an Enolase cit response developed was determined. Mice were immunised with a single dose of Enolase 241cit peptide in CpG/MPLA 2, 6 or 14 days before being sacrificed. Ex vivo Elispots were used to determine the IFNγ responses (FIG. 10). Immunisation with the mouse version of the peptide induced an IFNγ response which could be detected 2 days later. There was no significant difference between the responses seen after 2, 6 or 14 days. Immunisation with the human Enolase 241cit peptide led to an IFNγ response which was detectable after 6 days. Responses were significantly increased after 6 (p=0.0009) and 14 (p=0.0092) days when compared to responses after 2 days. These results suggest that there may be a pre-existing response to Enolase 241cit peptide which is specific to the endogenous murine peptide.

EXAMPLE 7. RESPONSES IN HEALTHY HUMAN DONORS

Mouse response to Enolase 241cit peptide can also be detected as early as 2 days after immunisation. This raised the question of whether humans have a pre-existing response to Enolase 241cit peptides which can be detected. To investigate this PBMCs were isolated from 6 healthy donors and cultured in the presence of Human Enolase peptides. Thymidine proliferation assays were performed on the cells after 4, 7 and 11 days and the proliferation index for each was calculated (FIG. 11A). 5/6 of the donors showed proliferation to Enolase 241cit peptide on at least one of the samples days. For example, Donor 1 showed a proliferative response to Enolase 241cit at day 11 (mean 20.4) and day 7 (mean 28.6) but not at day 4 (mean 0.8). Responses to Enolase 241 wt were consistently low at day 11 (mean 0.9), 7 (mean 1.2) and 4 (mean 0.3). In contrast Donor 2 showed only a low level response at day 11 (mean 2.7) and Donor 6 was a non-responder. For each donor HLA types were determined and are shown on the figure.

Donor 4 gave a high proliferation index at day 4 (mean 12.5) and day 7 (mean 28) and day 11 (4.4). This donor was chosen for further analysis. Supernatants were taken from cells at each time point and cytokine levels were analysed by Luminex. The response above the background level of the media only control was calculated for each cytokine (FIG. 11B). IFNγ and IL-10 gave citrullinated peptide specific responses which increased over time. Some increase in IL-17, Granzyme B and TNFα levels were seen in wild type stimulated cells however these responses were higher in the citrullinated peptide stimulated samples.

Next, PBMCs from donor 4 were labelled with Carboxyfluorescein succinimidyl ester (CFSE) prior to ex vivo culture in the presence of peptides. On day 7 and 10 cells were removed and stained with anti-CD8 and anti-CD4 fluorochome conjugated antibodies and analysed by flow cytometry (FIG. 11C). Of the proliferating $CFSE^{low}$ population between 73-96% of cells were CD4+ and 0-2% were CD8+. Enolase 241cit peptide showed increased proportions of $CFSE^{low}CD4^+$ cells compared to Enolase 241 wt peptide. At day 10, 15% of the Enolase 241cit lymphocytes are $CFSE^{low}CD4^+$ whereas 1% of the Enolase 241 wt peptides are $CFSE^{low}CD4^+$.

IFNγ responses have also been shown by IFNγ elispot assay in which PBMCs cultured for 13 days in Enolase 241 cit or wt peptides were restimulated with citrullinated or wt Enolase 241 peptide and cytokine release measured. FIG. 20A shows results of the IFNγ elispot assay on donors 1 and 4. Cells from both donors show responses to the citrullinated peptide but not the wt peptide. Further analysis of these responses by intracellular cytokine staining reveals IFNγ responses to be CD4 mediated. FIG. 20B shows intracellular cytokine staining on PBMCs from donor 4 cultured for 13 days in Enolase 241cit peptide and restimulated with either citrullinated or wt peptide. IFNγ positive CD4 cells are observed upon stimulation with the citrullinated peptide (0.44%) but not the wt peptide.

Luminex data from cultures on 3 donors shows IFNγ responses to the citrullinated Enolase 241 peptide with minimal response to the wt peptide and low level IL-10, TNFα or IL-17 responses (FIG. 20C).

These results suggest that healthy humans are able to develop a CD4 proliferative response to Enolase 241cit peptide which is citrulline specific and capable of producing Th1 cytokines.

EXAMPLE 8. IMMUNOHISTOCHEMISTRY

Citrullination is carried out by PAD enzymes and in particular the PAD2 and PAD4 enzymes. These require high levels of calcium and are usually activated in dead or dying cells or cells undergoing autophagy. Healthy cells should not express citrullinated proteins but tumours due to either hypoxia or nutritional stress will activate autophagy and citrullinated enolase. Colorectal, gastric, lung, breast and ovarian tumours were therefore stained for expression of enolase.

Colorectal Tumours:

232 colorectal tumours were stained with an ENO-1 specific monoclonal antibody (Table 2). 28% of tumours failed to stain, 56% showed weak staining (Hscore 1-100), 13% moderate staining (Hscore 101-200) and 3% showed strong staining (Hscore 201-300) were most cells stained intensely.

TABLE 2

Immunohistochemical staining of Colorectal tumour array for Eno-1

|  | Negative | Low | Moderate | High | Total |
|---|---|---|---|---|---|
| H-SCORE | 0 | 1-100 | 101-200 | 201-300 |  |
| cores | 655 | 129 | 30 | 8 | 232 |
|  | 28% | 56% | 13% | 3% |  |

Gastric Tumours:

70 gastric tumours were stained with an ENO-1 specific monoclonal antibody (Table 3). 16% of tumours failed to stain, 62% showed weak staining (Hscore 1-100), 19% moderate staining (Hscore 101-200) and 3% showed strong staining (Hscore 201-300) were most cells stained intensely.

TABLE 3

Immunohistochemical staining of gastric tumour array for Eno-1

|  | Negative | Low | Moderate | High | Total |
|---|---|---|---|---|---|
| H-SCORE | 0 | 1-100 | 101-200 | 201-300 |  |
| cores | 11 | 44 | 13 | 2 | 70 |
|  | 16% | 62% | 19% | 3% |  |

Non-Small Cell Lung Tumours:

223 non-small cell lung tumours were stained with an ENO-1 specific monoclonal antibody (Table 4). 20% of tumours failed to stain, 59% showed weak staining (Hscore 1-100), 17% moderate staining (Hscore 101-200) and 4% showed strong staining (Hscore 201-300) were most cells stained intensely.

TABLE 4

Immunohistochemical staining of non-small cell lung tumours tumour array for Eno-1

|  | Negative | Low | Moderate | High | Total |
|---|---|---|---|---|---|
| H-SCORE | 0 | 1-100 | 101-200 | 201-300 |  |
| cores | 45 | 132 | 37 | 9 | 223 |
| % | 20 | 59 | 17 | 4 |  |

Ovarian Tumours:

223 ovarian tumours were stained with an ENO-1 specific monoclonal antibody (Table 5). 42% of tumours failed to stain, 51% showed weak staining (Hscore 1-100), 2% moderate staining (Hscore 101-200) and 5% showed strong staining (Hscore 201-300) were most cells stained intensely.

TABLE 5

Immunohistochemical staining of Ovarian tumour array for Eno-1

|  | Negative | Low | Moderate | High | Total |
|---|---|---|---|---|---|
| H-SCORE | 0 | 1-100 | 101-200 | 201-300 |  |
| cores | 93 | 115 | 5 | 10 | 223 |
| % | 42 | 51 | 2 | 5 |  |

Breast Tumours:

858 breast tumours were stained with an ENO-1 specific monoclonal antibody (Table 6). 28% of tumours failed to stain, 19% showed weak staining (Hscore 1-100), 36% moderate staining (Hscore 101-200) and 17% showed strong staining (Hscore 201-300) were most cells stained intensely.

TABLE 6

Immunohistochemical staining of Breast tumour array for Eno-1

|  | Negative | Low | Moderate | High | Total |
|---|---|---|---|---|---|
| H-SCORE | 0 | 1-100 | 101-200 | 201-300 |  |
| cores | 239 | 165 | 310 | 144 | 858 |
| % | 28% | 19% | 36% | 17% |  |

Oestrogen Receptor Negative Breast Tumours:

249 oestrogen receptor negative breast tumours were stained with an ENO-1 specific monoclonal antibody (Table 7). 8% of tumours failed to stain, 14% showed weak staining (Hscore 1-100), 55% moderate staining (Hscore 101-200) and 23% showed strong staining (Hscore 201-300) were most cells stained intensely.

TABLE 7

Immunohistochemical staining of Oestrogen receptor negative breast tumour array for Eno-1

|  | Negative | Low | Moderate | High | Total |
|---|---|---|---|---|---|
| H-SCORE | 0 | 1-100 | 101-200 | 201-300 |  |
| cores | 19 | 36 | 136 | 58 | 249 |
| % | 8% | 14% | 55% | 23% |  |

EXAMPLE 9 HOMOLOGY OF ENOLASE BETWEEN DIFFERENT SPECIES

Enolases are highly conserved between, mouse, dog sheep, cows, horse, pig and humans (FIGS. 12-14). As the vaccine induces T cell responses in humans and mice and anti-tumour responses in mice, it can be assumed similar responses will be seen in other species.

REFERENCES

ABDEL-FATAH, T., ARORA, A., GORGUC, I., ABBOTTS, R., BEEBEEJAUN, S., STORR, S., MOHAN, V., HAWKES, C., SOOMRO, I., LOBO, D. N., PARSONS, S. L. & MADHUSUDAN, S. (2013) Are DNA repair factors promising biomarkers for personalized therapy in gastric cancer? *Antioxid Redox Signal,* 18, 2392-8.

ALTSCHUL, S. F., GISH, W., MILLER, W., MYERS, E. W. & LIPMAN, D. J. (1990) Basic local alignment search tool. *J Mol Biol,* 215, 403-10.

ALTSCHUL, S. F., MADDEN, T. L., SCHAFFER, A. A., ZHANG, J., ZHANG, Z., MILLER, W. & LIPMAN, D. J. (1997) Gapped BLAST and PSI-BLAST: a new generation of protein database search programs. *Nucleic Acids Res,* 25, 3389-402.

ANDREASEN, P. A., EGELUND, R. & PETERSEN, H. H. (2000) The plasminogen activation system in tumor growth, invasion, and metastasis. *Cell Mol Life Sci,* 57, 25-40.

AUSUBEL, J. (1992) *Short protocols in molecular biology,* John Wiley & Sons

BODANZSKY, B. (1984) *The practice of peptide synthesis,* New York, Springer Verlag.

CAMP, R. L., DOLLED-FILHART, M. & RIMM, D. L. (2004) X-tile: a new bio-informatics tool for biomarker assessment and outcome-based cut-point optimization. *Clin Cancer Res,* 10, 7252-9.

CAPELLO, M., FERRI-BORGOGNO, S., CAPPELLO, P. & NOVELLI, F. (2011) alpha-Enolase: a promising therapeutic and diagnostic tumor target. *FEBS J,* 278, 1064-74.

CAPPELLO, P., ROLLA, S., CHIARLE, R., PRINCIPE, M., CAVALLO, F., PERCONTI, G., FEO, S., GIOVARELLI, M. & NOVELLI, F. (2013) Vaccination with ENO1 DNA prolongs survival of genetically engineered mice with pancreatic cancer. *Gastroenterology,* 144, 1098-106.

CAPPELLO, P., TOMAINO, B., CHIARLE, R., CERUTI, P., NOVARINO, A., CASTAGNOLI, C., MIGLIORINI, P., PERCONTI, G., GIALLONGO, A., MILELLA, M., MONSURRO, V., BARBI, S., SCARPA, A., NISTICO, P., GIOVARELLI, M. & NOVELLI, F. (2009) An integrated humoral and cellular response is elicited in pancreatic cancer by alpha-enolase, a novel pancreatic ductal adenocarcinoma-associated antigen. *Int J Cancer,* 125, 639-48.

CHANG, G. C., LIU, K. J., HSIEH, C. L., HU, T. S., CHAROENFUPRASERT, S., LIU, H. K., LUH, K. T., HSU, L. H., WU, C. W., TING, C. C., CHEN, C. Y, CHEN, K. C., YANG, T. Y, CHOU, T. Y, WANG, W. H., WHANG-PENG, J. & SHIH, N. Y. (2006) Identification of alpha-enolase as an autoantigen in lung cancer: its overexpression is associated with clinical outcomes. *Clin Cancer Res,* 12, 5746-54.

CHOY, E. (2012) Understanding the dynamics: pathways involved in the pathogenesis of rheumatoid arthritis. *Rheumatology (Oxford),* 51 Suppl 5, v3-11.

COIMBRA, S., FIGUEIREDO, A., CASTRO, E., ROCHA-PEREIRA, P. & SANTOS-SILVA, A. (2012) The roles of cells and cytokines in the pathogenesis of psoriasis. *Int J Dermatol,* 51, 389-95; quiz 395-8.

DIAZ-RAMOS, A., ROIG-BORRELLAS, A., GARCIA-MELERO, A. & LOPEZ-ALEMANY, R. (2012) alpha-Enolase, a multifunctional protein: its role on pathophysiological situations. *J Biomed Biotechnol,* 2012, 156795.

DUNCAN, T. J., ROLLAND, P., DEEN, S., SCOTT, I. V., LIU, D. T., SPENDLOVE, I. & DURRANT, L. G. (2007) Loss of IFN gamma receptor is an independent prognostic factor in ovarian cancer. *Clin Cancer Res,* 13, 4139-45.

DURRANT, L. G., HARDING, S. J., GREEN, N. H., BUCKBERRY, L. D. & PARSONS, T.
(2006) A new anticancer glycolipid monoclonal antibody, SC104, which directly induces tumor cell apoptosis. *Cancer Res,* 66, 5901-9.

FU, Q. F., LIU, Y., FAN, Y, HUA, S. N., QU, H. Y, DONG, S. W., LI, R. L., ZHAO, M. Y, ZHEN, Y, YU, X. L., CHEN, Y. Y, LUO, R. C., LI, R., LI, L. B., DENG, X. J., FANG, W. Y, LIU, Z. & SONG, X. (2015) Alpha-enolase promotes cell glycolysis, growth, migration, and invasion in non-small cell lung cancer through FAK-mediated PI3K/AKT pathway. *J Hematol Oncol,* 8, 22.

GREEN, D. R. & LEVINE, B. (2014) To be or not to be? How selective autophagy and cell death govern cell fate. *Cell,* 157, 65-75.

GRUNEWALD, J. & EKLUND, A. (2007) Role of CD4+ T cells in sarcoidosis. *Proc Am Thorac Soc,* 4, 461-4.

HOLMDAHL, R., KLARESKOG, L., RUBIN, K., LARSSON, E. & WIGZELL, H. (1985) T lymphocytes in collagen II-induced arthritis in mice. Characterization of arthritogenic collagen II-specific T-cell lines and clones. *Scand J Immunol,* 22, 295-306.

JANG, B., JEON, Y. C., CHOI, J. K., PARK, M., KIM, J. I., ISHIGAMI, A., MARUYAMA, N., CARP, R. I., KIM, Y. S. & CHOI, E. K. (2012) Peptidylarginine deiminase modulates the physiological roles of enolase via citrullination: links between altered multifunction of enolase and neurodegenerative diseases. *Biochem J,* 445, 183-92.

JANG, B., MN, J. K., JEON, Y. C., CHO, H. J., ISHIGAMI, A., CHOI, K. C., CARP, R. I., MARUYAMA, N., KIM, Y. S. & CHOI, E. K. (2010) Involvement of peptidylarginine deiminase-mediated post-translational citrullination in pathogenesis of sporadic Creutzfeldt-Jakob disease. *Acta Neuropathol,* 119, 199-210.

JANG, B., KIM, E., CHOI, J. K., JIN, J. K., KIM, J. I., ISHIGAMI, A., MARUYAMA, N., CARP, R. I., KIM, Y. S. & CHOI, E. K. (2008) Accumulation of citrullinated proteins by up-regulated peptidylarginine deiminase 2 in brains of scrapie-infected mice: a possible role in pathogenesis. *Am J Pathol,* 173, 1129-42.

KARLIN, S. & ALTSCHUL, S. F. (1993) Applications and statistics for multiple high-scoring segments in molecular sequences. *Proc Natl Acad Sci USA,* 90, 5873-7.

KINLOCH, A., LUNDBERG, K., WAIT, R., WEGNER, N., LIM, N. H., ZENDMAN, A. J., SAXNE, T., MALMSTROM, V. & VENABLES, P. J. (2008) Synovial fluid is a site of citrullination of autoantigens in inflammatory arthritis. *Arthritis Rheum*, 58, 2287-95.

KINLOCH, A., TATZER, V., WAIT, R., PESTON, D., LUNDBERG, K., DONATIEN, P., MOYES, D., TAYLOR, P. C. & VENABLES, P. J. (2005) Identification of citrullinated alpha-enolase as a candidate autoantigen in rheumatoid arthritis. *Arthritis Res Ther*, 7, R1421-9.

KONDO, H., SAHARA, H., MIYAZAKI, A., NABETA, Y., HIROHASHI, Y, KANASEKI, T., YAMAGUCHI, A., YAMADA, N., HIRAYAMA, K., SUZUKI, M., HAMURO, J., TORIGOE, T., TAKAHASHI, N., KOHAMA, G. I., IKEDA, H. & SATO, N. (2002) Natural antigenic peptides from squamous cell carcinoma recognized by autologous HLA-DRB-restricted CD4+ T cells. *Jpn J Cancer Res*, 93, 917-24.

LUNDBERG, K., KINLOCH, A., FISHER, B. A., WEGNER, N., WAIT, R., CHARLES, P., MIKULS, T. R. & VENABLES, P. J. (2008) Antibodies to citrullinated alpha-enolase peptide 1 are specific for rheumatoid arthritis and cross-react with bacterial enolase. *Arthritis Rheum*, 58, 3009-19.

MAHDI, H., FISHER, B. A., KALLBERG, H., PLANT, D., MALMSTROM, V., RONNELID, J., CHARLES, P., DING, B., ALFREDSSON, L., PADYUKOV, L., SYMMONS, D. P., VENABLES, P. J., KLARESKOG, L. & LUNDBERG, K. (2009) Specific interaction between genotype, smoking and autoimmunity to citrullinated alpha-enolase in the etiology of rheumatoid arthritis. *Nat Genet*, 41, 1319-24.

MARANGOS, P. J., ZIS, A. P., CLARK, R. L. & GOODWIN, F. K. (1978) Neuronal, non-neuronal and hybrid forms of enolase in brain: structural, immunological and functional comparisons. *Brain Res*, 150, 117-33.

METHERINGHAM, R. L., PUDNEY, V. A., GUNN, B., TOWEY, M., SPENDLOVE, I. & DURRANT, L. G. (2009) Antibodies designed as effective cancer vaccines. *MAbs*, 1, 71-85.

MILES, L. A., DAHLBERG, C. M., PLESCIA, J., FELEZ, J., KATO, K. & PLOW, E. F. (1991) Role of cell-surface lysines in plasminogen binding to cells: identification of alpha-enolase as a candidate plasminogen receptor. *Biochemistry*, 30, 1682-91.

MUNZ, C. (2012) Antigen Processing for MHC Class II Presentation via Autophagy. *Front Immunol*, 3, 9.

MYERS, E. W. & MILLER, W. (1989) Approximate matching of regular expressions. *Bull Math Biol*, 51, 5-37.

NAKAMURA, N., DAI, Q., WILLIAMS, J., GOULDING, E. H., WILLIS, W. D., BROWN, P. R. & EDDY, E. M. (2013) Disruption of a spermatogenic cell-specific mouse enolase 4 (eno4) gene causes sperm structural defects and male infertility. *Biol Reprod*, 88, 90.

PANCHOLI, V. (2001) Multifunctional alpha-enolase: its role in diseases. *Cell Mol Life Sci*, 58, 902-20.

PEARSON, W. R. & LIPMAN, D. J. (1988) Improved tools for biological sequence comparison. *Proc Natl Acad Sci USA*, 85, 2444-8.

PLUCKTHUN, A. (1991) Antibody engineering: advances from the use of *Escherichia coli* expression systems. *Biotechnology (N Y)*, 9, 545-51.

PRINCIPE, M., CERUTI, P., SHIH, N. Y, CHATTARAGADA, M. S., ROLLA, S., CONTI, L., BESTAGNO, M., ZENTILIN, L., YANG, S. H., MIGLIORINI, P., CAPPELLO, P., BURRONE, O. & NOVELLI, F. (2015) Targeting of surface alpha-enolase inhibits the invasiveness of pancreatic cancer cells. *Oncotarget*.

REFF, M. E. (1993) High-level production of recombinant immunoglobulins in mammalian cells. *Curr Opin Biotechnol*, 4, 573-6.

REMINGTON, R. (1980) *Remington's pharmaceutical sciences*, Mack Pub. Co.

SAMBROOK, J., FRITSCH AND MANIATIS (1989) *Molecular cloning: A laboratory manual*, Cold Spring Harbor Laboratory Press.

SCHMID, D., PYPAERT, M. & MUNZ, C. (2007) Antigen-loading compartments for major histocompatibility complex class II molecules continuously receive input from autophagosomes. *Immunity*, 26, 79-92.

SEMENZA, G. L., JIANG, B. H., LEUNG, S. W., PASSANTINO, R., CONCORDET, J. P., MAIRE, P. & GIALLONGO, A. (1996) Hypoxia response elements in the aldolase A, enolase 1, and lactate dehydrogenase A gene promoters contain essential binding sites for hypoxia-inducible factor 1. *J Biol Chem*, 271, 32529-37.

SIMPSON, J. A., AL-ATTAR, A., WATSON, N. F., SCHOLEFIELD, J. H., ILYAS, M. & DURRANT, L. G. (2010) Intratumoral T cell infiltration, MHC class I and STAT1 as biomarkers of good prognosis in colorectal cancer. *Gut*, 59, 926-33.

STEWART (1984) *Solid phase peptide synthesis*, Rockford, Ill. Pierce Chemical Company.

STORR, S. J., ZAITOUN, A. M., ARORA, A., DURRANT, L. G., LOBO, D. N., MADHUSUDAN, S. & MARTIN, S. G. (2012) Calpain system protein expression in carcinomas of the pancreas, bile duct and ampulla. *BMC Cancer*, 12, 511.

TORELLI, A. & ROBOTTI, C. A. (1994) ADVANCE and ADAM: two algorithms for the analysis of global similarity between homologous informational sequences. *Comput Appl Biosci*, 10, 3-5.

TRILL, J. J., SHATZMAN, A. R. & GANGULY, S. (1995) Production of monoclonal antibodies in COS and CHO cells. *Curr Opin Biotechnol*, 6, 553-60.

ZHAO, M., FANG, W., WANG, Y, GUO, S., SHU, L., WANG, L., CHEN, Y, FU, Q., LIU, Y, HUA, S., FAN, Y, LIU, Y, DENG, X., LUO, R., MEI, Z., JIANG, Q. & LIU, Z. (2015) Enolase-1 is a therapeutic target in endometrial carcinoma. *Oncotarget*.

ZHOU, W., CAPELLO, M., FREDOLINI, C., PIEMONTI, L., LIOTTA, L. A., NOVELLI, F. & PETRICOIN, E. F. (2010) Mass spectrometry analysis of the post-translational modifications of alpha-enolase from pancreatic ductal adenocarcinoma cells. *J Proteome Res*, 9, 2929-36.

The invention claimed is:

1. A method for the treatment of cancer in a subject in need thereof comprising administering to the subject a citrullinated peptide comprising, consisting essentially of, or consisting of:
 i) an amino acid sequence selected from the group consisting of:

```
VIGMDVAASEFFcitSGKYDLD,         (SEQ ID NO: 1)

VIGMDVAASEFYcitSGKYDLD,         (SEQ ID NO: 2)

EVDLFTSKGLFcitAAVPSGAS,         (SEQ ID NO: 3)

EVDLYTAKGLFcitAAVPSGAS,         (SEQ ID NO: 4)

KGVPLYcitHIADLAGNSEVIL,         (SEQ ID NO: 5)

KGVPLYcitHIADLAGNPEVIL,         (SEQ ID NO: 6)

VGDDLTVTNPKcitIAKAVNEK,         (SEQ ID NO: 7)

VGDDLTVTNPKcitIAKAASEK,         (SEQ ID NO: 8)

IFDScitGNPTVEVDLF,              (SEQ ID NO: 9)
or
IFDScitGNPTVEVDLY.              (SEQ ID NO: 10)
```
wherein "cit" represents citrulline, or
 ii) the amino acid sequence of i), with the exception of 1, 2 or 3 amino acid substitutions, and/or 1, 2 or 3 amino acid insertions, and/or 1, 2 or 3 amino acid deletions in a non-citrulline position.

2. The method of claim 1, wherein the cancer is breast cancer, colorectal cancer, gastric cancer, non-small cell lung cancer, ovarian cancer, endometrial carcinoma, pancreatic cancer, leukaemia, melanoma, head and neck cancer or lung cancer.

3. The method claim 1, wherein the subject is a human or non-human animal.

4. The method of claim 1, wherein the citrullinated peptide is administered as a pharmaceutical composition comprising the peptide in combination with a pharmaceutically acceptable carrier.

5. The method of claim 3, wherein the subject is a human.

6. The method of claim 5, wherein the subject expresses HLA-DP4.

7. The method of claim 2, wherein the cancer is breast cancer.

8. The method of claim 7, wherein the cancer is estrogen receptor negative breast cancer.

9. The method of claim 2, wherein the cancer is ovarian cancer.

10. The method of claim 2, wherein the cancer is pancreatic cancer.

11. The method of claim 10, wherein pancreatic cancer is pancreatic ductal adenocarcinoma.

12. The method of claim 1, wherein the citrullinated peptide comprises the amino acid sequence VIGMDVAASEFFcitSGKYDLD (SEQ ID NO: 1), wherein "cit" represents citrulline.

13. The method of claim 1, wherein the citrullinated peptide consists essentially of the amino acid sequence VIGMDVAASEFFcitSGKYDLD (SEQ ID NO: 1), wherein "cit" represents citrulline.

14. The method of claim 1, wherein the citrullinated peptide consists of the amino acid sequence VIGMDVAASEFFcitSGKYDLD (SEQ ID NO: 1), wherein "cit" represents citrulline.

* * * * *